United States Patent
Lee et al.

(10) Patent No.: US 11,587,643 B2
(45) Date of Patent: Feb. 21, 2023

(54) METHODS AND APPARATUSES FOR A UNIFIED ARTIFICIAL INTELLIGENCE PLATFORM TO SYNTHESIZE DIVERSE SETS OF PEPTIDES AND PEPTIDOMIMETICS

(71) Applicant: Peptilogics, Inc., Pittsburgh, PA (US)

(72) Inventors: Francis Lee, Cambridge, MA (US); Jonathan D. Steckbeck, Seven Fields, PA (US); Hannes Holste, Los Angeles, CA (US)

(73) Assignee: Peptilogics, Inc., Pittsburgh, PA (US)

( * ) Notice: Subject to any disclaimer, the term of this patent is extended or adjusted under 35 U.S.C. 154(b) by 0 days.

(21) Appl. No.: 17/401,715

(22) Filed: Aug. 13, 2021

(65) Prior Publication Data

US 2022/0359041 A1 Nov. 10, 2022

Related U.S. Application Data

(60) Provisional application No. 63/185,841, filed on May 7, 2021, provisional application No. 63/185,770, filed on May 7, 2021.

(51) Int. Cl.
*G16B 40/00* (2019.01)
*G16B 30/20* (2019.01)
*G06N 20/00* (2019.01)
*G06N 5/04* (2006.01)

(52) U.S. Cl.
CPC .............. *G16B 40/00* (2019.02); *G06N 5/04* (2013.01); *G06N 20/00* (2019.01); *G16B 30/20* (2019.02)

(58) Field of Classification Search
None
See application file for complete search history.

(56) References Cited

U.S. PATENT DOCUMENTS

| | | | |
|---|---|---|---|
| 9,169,287 B2 | 10/2015 | Simon et al. | |
| 9,695,214 B2 | 7/2017 | Simon et al. | |
| 9,868,759 B2 | 1/2018 | Simon et al. | |
| 10,683,325 B2 | 6/2020 | Thomas, III et al. | |
| 10,889,613 B2 | 1/2021 | Simon et al. | |
| 10,988,504 B2 | 4/2021 | Simon et al. | |
| 2011/0035155 A1 | 2/2011 | Vendruscolo et al. | |
| 2017/0081359 A1 | 3/2017 | Thomas, III et al. | |
| 2019/0065677 A1 | 2/2019 | Gifford | |
| 2020/0316552 A1 | 10/2020 | Lim et al. | |
| 2021/0047365 A1 | 2/2021 | Thomas et al. | |
| 2021/0188901 A1 | 6/2021 | Thomas, III et al. | |
| 2021/0215691 A1 | 7/2021 | Valle et al. | |

OTHER PUBLICATIONS

Granda, Jaroslaw M., et al. "Controlling an organic synthesis robot with machine learning to search for new reactivity." Nature 559. 7714 (2018): 377-381.*

Atherton et al., A physically supported gel polymer for low pressure, continuous flow solid phase reactions. Application to solid phase peptide synthesis., J. Chem. Soc., Chem. Commun., 1981, pp. 1151-1152.
Atherton et al., Internal association in solid phase peptide synthesis. Synthesis of cytochrome C residues 66-104 an polyamide supports, J. Chem. Soc., Chem. Commun., 1980, pp. 970-971.
Badowski et al., Synergy Between Expert and Machine-Learning Approaches Allows for Improved Retrosynthetic Planning, Angewandte Chemie International Edition, 2020, vol. 59, pp. 725-730.
Baker, 1,500 scientists lift the lid on reproducibility, Nature News, 2016, vol. 533, p. 452.
Bédard et al., Reconfigurable system for automated optimization of diverse chemical reactions, Science, 2018, vol. 361, p. 1220.
Bedford et al., Amino acid structure and difficult sequences in solid phase peptide synthesis, International Journal of Peptide and Protein Research, 1992, vol. 40, pp. 300-307.
Bondalapati et al., Expanding the chemical toolbox for the synthesis of large and uniquely modified proteins, Nature Chemistry, 2016, vol. 8, pp. 407-418.
Brown et al., Analysis of Past and Present Synthetic Methodologies on Medicinal Chemistry: Where Have All the New Reactions Gone?, J. Med. Chem., 2016, vol. 59, pp. 4443-4458.
Cameron et al., Peptide synthesis. Part 13. Feedback control in solid phase synthesis. Use of fluorenylmethoxycarbonyl amino acid 3,4-dihydro-4-oxo-1,2,3-benzotriazin-3-yl esters in a fully automated system., J. Chem. Soc., Perkin Trans., 1988, vol. 1, pp. 2895-2901.
Coley et al., A robotic platform for flow synthesis of organic compounds informed by AI planning, Science, 2019, vol. 365, p. eaax1566.
Coley et al., Autonomous discovery in the chemical sciences part II: Outlook. Angewandte Chemie International, 2019, Edition 0, doi:10.1002/anie.201909989.
Coley et al., Machine Learning in Computer-Aided Synthesis Planning, Acc. Chem. Res., 2018, vol. 51, pp. 1281-1289.
Coley et al., Prediction of Organic Reaction Outcomes Using Machine Learning, ACS Cent. Sci., 2017, vol. 3, pp. 434-443.
Dryland et al., Peptide synthesis. Part 8. A system for solid-phase synthesis under low pressure continuous flow conditions., J. Chem. Soc., Perkin Trans., 1986, vol. 1, pp. 125-137.
Gao et al., Using Machine Learning To Predict Suitable Conditions for Organic Reactions, ACS Cent. Sci., 2018, vol. 4, pp. 1465-1476.
Hartrampf et al., Synthesis of proteins by automated flow chemistry, Science, 2020, vol. 368, p. 980.

(Continued)

*Primary Examiner* — G Steven Vanni
(74) *Attorney, Agent, or Firm* — Dickinson Wright PLLC; Stephen A. Mason; Jonathan H. Harder

(57) ABSTRACT

In one aspect, a method is disclosed wherein an artificial intelligence (AI) enabled automated flow synthesis platform is configured to generate optimized synthesizing recipes which enable a sequence to be synthesized using an automated flow process. The method includes receiving a synthesizing recipe including parameters used during the automated flow process to synthesize the sequence, receiving spectral data from detectors monitoring the automated flow process in a reaction chamber, where the spectral data corresponds to a reaction point in the automated flow process, and determining, based on indicators associated with the spectral data, characteristics of a chemical reaction at the reaction point in the automated flow process. An artificial intelligence engine determines the chemical reaction. The method includes associating, based on the spectral data, the synthesizing recipe with the chemical reaction.

30 Claims, 47 Drawing Sheets

(56) References Cited

OTHER PUBLICATIONS

Häse et al., Phoenics: A Bayesian Optimizer for Chemistry, ACS Cent. Sci., 2018, vol. 4, pp. 1134 1145.
Kent, Total chemical synthesis of proteins, Chem. Soc. Rev., 2009, vol. 38, pp. 338-351.
Li et al., Synthesis of many different types of organic small molecules using one automated process, Science, 2015, vol. 347, p. 1221.
Lukas et al., Solid-phase peptide synthesis under continuous-flow conditions, Proc Natl Acad Sci USA, 1981, vol. 78, p. 2791.
Macleod et al., Self-driving laboratory for accelerated discovery of thin-film materials, Sci Adv., 2020, vol. 6, p. eaaz8867.
Merrifield, Solid phase peptide synthesis. I. The synthesis of a tetrapeptide, Journal of the American Chemical Society, 1963, vol. 85, pp. 2149-2154.
Mijalis et al., A fully automated flow-based approach for accelerated peptide synthesis, Nature Chemical Biology, 2017, vol. 13, p. 464.
Milton et al., Prediction of difficult sequences in solidphase peptidesynthesis, J. Am. Chem. Soc., 1990, vol. 112, pp. 6039-6046.
Mohapatra et al., Deep Learning for Prediction and Optimization of Fast-Flow Peptide Synthesis, ACS Cent. Sci., 2020, vol. 6, pp. 2277-2286.
Reizman et al., Feedback in Flow for Accelerated Reaction Development, Acc. Chem. Res., 2016, vol. 49, pp. 1786-1796.
Roch et al., ChemOS: Orchestrating autonomous experimentation, Sci. Robotics, 2018, vol. 3, p. eaat5559.
Sarin et al., Properties of swollen polymer networks. Solvation and swelling of peptide-containing resins in solid-phase peptide synthesis, J. Am. Chem. Soc., 1980, vol. 102, pp. 5463-5470.
Segler et al., Planning chemical syntheses with deep neural networks and symbolic AI, Nature, 2018, vol. 555, pp. 604-610.
Steiner et al., Organic synthesis in a modular robotic system driven by a chemical programming language, Science, 2019, vol. 363, p. eaav2211.
Trobe et al., The Molecular Industrial Revolution: Automated Synthesis of Small Molecules, Angewandte Chemie International Edition, 2018, vol. 57, pp. 4192-4214.
Waltz et al., Automating Science, Science, 2009, vol. 324, p. 43.
Wei et al., Neural Networks for the Prediction of Organic Chemistry Reactions, ACS Cent. Sci., 2016, vol. 2, pp. 725-732.a.
Woerkom et al., Difficult couplings in stepwise solid phase peptide synthesis: predictable or just a guess?, International Journal of Peptide and Protein Research, 1991, vol. 38, pp. 103-113.
Woerly et al., Synthesis of most polyene natural product motifs using just 12 building blocks and one coupling reaction, Nature Chemistry, 2014, vol. 6, pp. 484-491.
Zhou et al., Optimizing Chemical Reactions with Deep Reinforcement Learning, ACS Cent. Sci., 2017, vol. 3, pp. 1337-1344.
Zompra et al., Manufacturing peptides as active pharmaceutical ingredients, Future Medicinal Chemistry, 2009, vol. 1, pp. 361-377.
Biswas, "Principles of Machine Learning-Guided Protein Engineering" Dissertation, Harvard University, 2020, pp. 1-195.
International Search Report and Written Opinion for PCT Application No. PCT/US2022/028174, dated Aug. 12, 2022, 15 pages.
Gromski et al., "Universal Chemical Synthesis and Discovery with 'The Chemputer'," Trends in Chemistry, Jan. 2020, pp. 1-9, vol. 2, No. 1.
Sans Victor et al., "Towards dial-a-molecule by integrating continuous flow, analytics and self-optimisation," Chemical Society Reviews, Jan. 2016, pp. 2032-2043, vol. 45, No. 8.

* cited by examiner

| Encoding | Compressed? | Information |
|---|---|---|
| SMILES | No | Structure |
| Morgan Fingerprints | Yes | Structure |
| InChI | No | Structure |
| QSAR | No | Physiochemical Properties |
| One-Hot | No | Structure |
| N-gram | No | Structure |
| Z-descriptors | No | Physiochemical Properties |
| GGNN | Yes | Structure |
| GRN | Yes | Structure |
| MPNN | Yes | Structure |
| Knowledge Graph (Structural/Semantic) | No | Structure and Physiochemical Properties |

METHODS AND APPARATUSES FOR A UNIFIED ARTIFICIAL INTELLIGENCE PLATFORM TO SYNTHESIZE DIVERSE SETS OF PEPTIDES AND PEPTIDOMIMETICS

CROSS-REFERENCE TO RELATED APPLICATIONS

The present application claims priority to and the benefit of U.S. Prov. Pat. App. 63/185,841, filed May 7, 2021, titled "Methods and Apparatuses for a Unified Artificial Intelligence Platform to Synthesize Diverse Sets of Peptides and Peptidomimetics," and U.S. Prov. Pat. App. 63/185,770, filed May 7, 2021, titled "Methods and Apparatuses for Generating Peptides by Synthesizing a Portion of a Design Space to Identify Peptides Having Non-Canonical Amino Acids." The contents of the above-referenced applications are incorporated herein by reference in their entireties for all purposes.

TECHNICAL FIELD

This disclosure relates generally to drug discovery. More specifically, this disclosure relates to methods and apparatuses for a unified artificial intelligence platform to synthesize diverse sets of peptides and peptidomimetics.

BACKGROUND

Therapeutics may refer to a branch of medicine concerned with the treatment of disease and the action of remedial agents (e.g., drugs). Therapeutics includes, but is not limited to, the field of ethical pharmaceuticals. Entities in the therapeutics industry may discover, develop, produce, and market drugs for use as medications to be administered or self-administered to patients. Goals of administering or self-administering the drugs may include curing the patient of a disease, causing an active disease to enter a state of remission, vaccinating the patient by stimulating the immune system to better protect against the disease, or alleviating, mitigating or ameliorating a symptom. Existing drug discoveries may be based on any combination of human design, high-throughput screening, synthetic products and natural substances.

SUMMARY

In one aspect, a method is disclosed wherein an artificial intelligence (AI)-enabled automated flow synthesis platform is configured to generate optimized synthesizing recipes which, using an automated flow process, enable a sequence (e.g., sequence of amino acids, such as a peptide) to be synthesized. The method includes receiving a synthesizing recipe, wherein the synthesizing recipe includes attributes of parameters used during the automated flow process to synthesize the sequence, receiving spectral data from detectors monitoring the automated flow process in a reaction chamber, wherein the spectral data corresponds to a reaction point in the automated flow process, and determining, based on indicators associated with the spectral data, characteristics of a chemical reaction at the reaction point in the automated flow process. An artificial intelligence engine may determine the chemical reaction. The method includes associating, based on the spectral data, the synthesizing recipe with the chemical reaction.

A computer-implemented automated flow synthesis platform (AFSP) configured to use an artificial intelligence (AI) engine is disclosed. The AFSP may include a reaction chamber configured to synthesize a sequence, one or more detectors configured to monitor the synthesis of the sequence in the reaction chamber, wherein the synthesis uses an automated flow process, and a computing device communicatively coupled to the one or more detectors. The computing device may be configured to receive one or more measurements from the one or more detectors, where the one or more measurements may include a spectral profile at each coupling of each amino acid in the sequence. The computing device may train, using training data including the one or more measurements, one or more machine learning models to determine a synthesizing recipe that enables the sequence to be synthesized, wherein the synthesizing recipe includes one or more attributes of parameters used to synthesize the sequence during the automated flow process. The computing device controls, using the synthesizing recipe, the synthesis of the sequence in the reaction chamber.

In another aspect, a system may include a memory device storing instructions and a processing device communicatively coupled to the memory device. The processing device may execute the instructions to perform one or more operations of any method disclosed herein.

In another aspect, a tangible, non-transitory computer-readable medium may store instructions and a processing device may execute the instructions to perform one or more operations of any method disclosed herein.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, independent of whether those elements are in physical contact with one another. The terms "transmit," "receive," and "communicate," as well as derivatives thereof, encompass both direct and indirect communication. The terms "transmit," "receive," and "communicate," as well as derivatives thereof, encompass both communication with remote systems and communication within a system, including reading and writing to different portions of a memory device. The terms "include" and "comprise," as well as derivatives thereof, mean inclusion without limitation. The term "or" is inclusive, meaning or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "translate" may refer to any operation performed wherein data is input in one format, representation, language (computer, purpose-specific, such as drug design or integrated circuit design), structure, appearance or other written, oral or representable instantiation and data is output in a different format, representation, language (computer, purpose-specific, such as drug design or integrated circuit design), structure, appearance or other written, oral or representable instantiation, wherein the data output has a similar or identical meaning, semantically or otherwise, to the data input. Translation as a process includes but is not limited to substitution (including macro substitution), encryption, hashing, encoding, decoding or other mathematical or other operations performed on the input data. The same means of translation performed on the same input data will consistently yield the same output data, while a different means of translation performed on the same input data may yield different output data which nevertheless preserves all or part of the meaning or function of the input data, for a given purpose. Notwithstanding the foregoing, in a mathematically degenerate case, a translation can output data identical to the input data. The term "controller" means any device, system or part thereof that controls at least one operation. Such a controller may be implemented in hardware or a combination of hardware and software or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable storage medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer readable storage medium includes media where data can be permanently stored and media where data can be stored and later overwritten, such as a rewritable optical disc or an erasable memory device.

The terms "candidate drugs" and "candidate drug compounds" may be used interchangeably herein.

The term "peptidomimetic sequence" or "peptidomimetic" may refer to a small protein-like chain designed to mimic a peptide. Peptidomimetic sequences may be created by modifying an existing peptide sequence or by designing similar systems that mimic peptides. One class of peptidomimetic includes peptoids (poly-N-substituted glycines). A peptoid has side chains appended to the nitrogen atom of the peptide backbone (rather than the α-carbons, as they are in α-amino acids). The chemical structure of a peptide may be altered to create the peptidomimetic such that the selected or relevant molecular properties (e.g., stability or biological activity) are advantageously adjusted.

The term "amino acid" may refer to an organic compound that contains amine and carboxyl functional groups, along with a side chain (R group) specific to each amino acid. Amino acids which have the amine group attached to the α-carbon atom next to the carboxyl group are known as the α-amino acids.

The term "universal genetic code" may refer to the set of DNA and RNA sequences that determine the amino acid sequences used in the synthesis of an organism's proteins. That is, the universal genetic code is a set of 64 codons (DNA or mRNA sequences of nucleotide triplets) corresponding to the 20 amino acids used for protein synthesis and used as signals for starting and stopping protein synthesis.

The term "canonical amino acids" (also referred to as "standard amino acids") may refer to the 20 amino acids encoded directly by the codons of the universal genetic code. Specifically, the 20 amino acids, when grouped by side chains are those with aliphatic side chains, namely: alanine, glycine, isoleucine, leucine, proline, and valine; those with aromatic side chains, namely: phenylalanine, tryptophan, and tyrosine; those with acidic side chains, namely: aspartic acid and glutamic acid; those with basic side chains, namely: arginine, histidine, and lysine; those with hydroxylic side chains, namely: serine and threonine; those with sulphur-containing side chains, namely: cysteine and methionine; and those with amidic side chains, namely: asparagine and glutamine.

The term "non-canonical amino acids" (also referred to as "non-standard amino acids") may refer to amino acids encoded by variant codons not present in the universal genetic code or by a transfer ribonucleic acid (tRNA). Most of the non-canonical amino acids are also non-proteinogenic (i.e., they cannot be incorporated into proteins during translation), but two of them are proteinogenic (as they can be incorporated translationally into proteins by exploiting information not encoded in the universal genetic code). The two non-canonical proteinogenic amino acids are selenocysteine and pyrrolysine.

The term "modified amino acids" may refer to amino acids included in a polypeptide chain having a fully formed backbone chemically modified (e.g., the R group) to alter the polypeptide's chemistry.

The term "synthesizing recipe" may refer to one or more values of attributes of parameters that indicate or specify how to control an automated flow synthesis process. The attributes of the parameters may include values, names, quantifiers, identifiers, codes, properties, etc.

The term "linker" may refer to a bifunctional molecule anchoring a growing peptide to an insoluble carrier (e.g., resin). Typically, linkers are short peptide sequences that occur between protein domains. Linkers are often composed of flexible residues like glycine and serine so that the adjacent protein domains are free to move relative to one another.

The term "cancer" may refer to a disease caused by or correlated with an uncontrolled division of abnormal cells in a part of the body.

The term "calculate" may be used interchangeably with any of the following terms: simulate, emulate, determine, generate, formulate, execute, or obtain.

The term "solvent" may refer to a class of chemical compounds described by function, wherein the chemical compounds may, for example, be in a liquid, solid, or gas state. Solvents are used to dissolve, suspend or extract materials, without chemically changing either the solvents or other materials. Types of solvents may include hydrocarbon solvents, oxygenated solvents, halogenated solvents, and the like.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings, in which:

FIG. 1G illustrates types of encodings to represent certain types of drug information according to certain embodiments of this disclosure;

FIG. 8A-8C provide illustrations of views of a selected candidate drug compound according to certain embodiments of this disclosure;

FIG. 16 illustrates an example user interface for tracking information pertaining to trials according to certain embodiments of this disclosure;

DETAILED DESCRIPTION

Figure 1A:
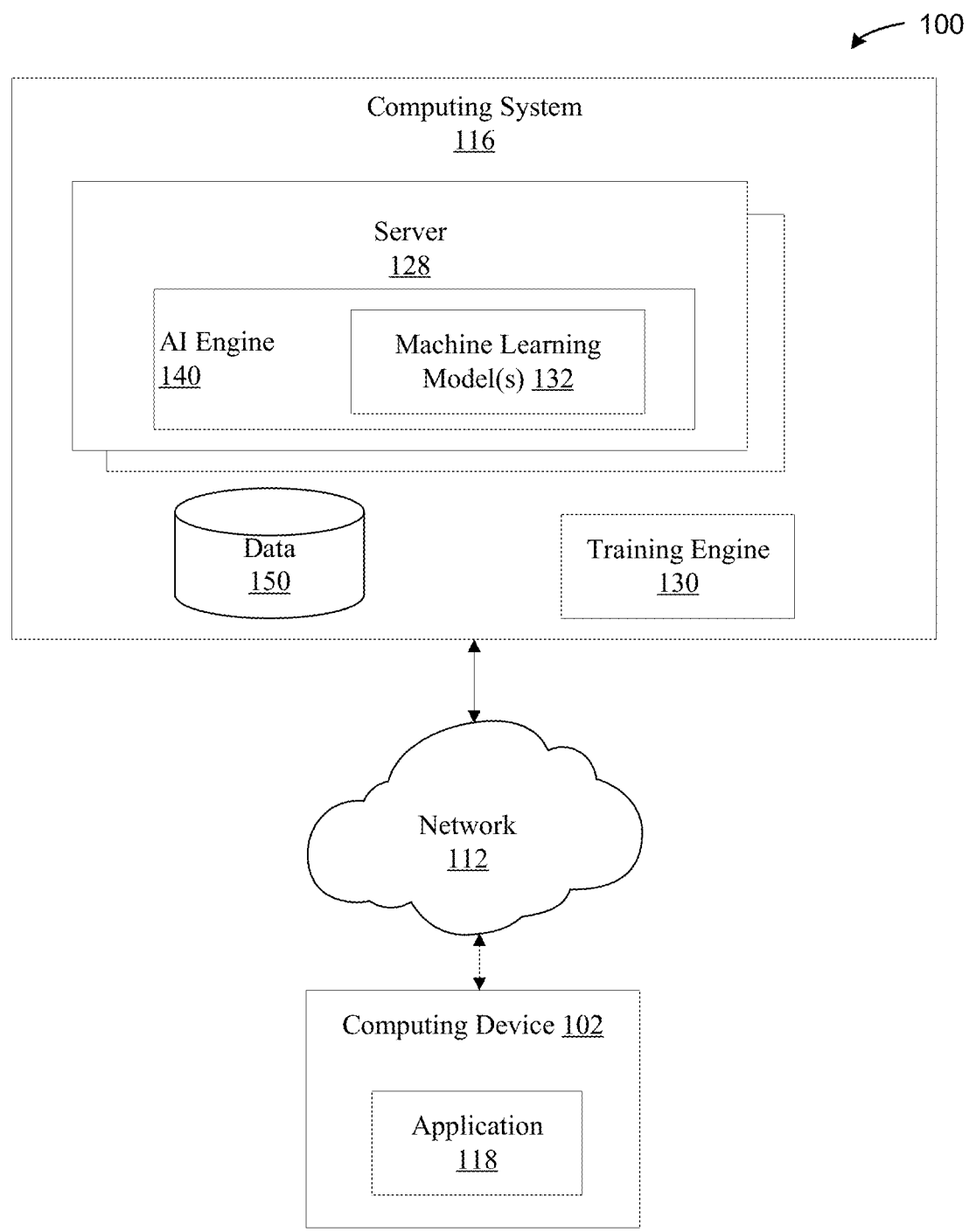
FIG. 1A illustrates a high-level component diagram of an illustrative system architecture according to certain embodiments of this disclosure.

Conventional drug discoveries based on human design, high-throughput screening, or natural substances may be inefficient, riven with noise, limited in application, not efficacious, dangerous or poisonous, or not defensible. Further, in some instances, there are instances of certain diseases (e.g., instances of prosthetic joint infections) that do not have a corresponding existing therapeutic to treat the certain diseases or which provide temporary results against which the disease is refractory. One reason for the lack of an existing therapeutic may be the conventional drug discovery techniques are incapable of discovering the therapeutic needed to treat the certain diseases. By "treat" is meant that the disease at hand is cured inter alia, that it is not refractory to treatment. The amount of knowledge, data, assumptions, and queries used to discover a therapeutic to treat the certain disease may be unattainable, overwhelming, or inefficiently determined, such that conventional drug discovery techniques cannot overcome these obstacles. Improvements are desired in the field of therapeutics.

Further, conventional techniques for searching for candidate drugs use limited design spaces. For example, some conventional techniques focus on a fact about drugs, where such facts constrain the design space that is searched. The design space may refer to parameterization of limits and constraints in a drug space where candidate drug compounds may be designed. A design space may also refer to a multidimensional combination and interaction of input variables (e.g., material attributes) and process parameters that have been demonstrated to provide assurance of quality. An example of such a fact may include a certain biomedical activity known to be linked to an alpha-helix physical structure of a peptide, where conventional techniques may search for other activities that may result from a peptide having the alpha-helix physical structure. Such a limited design space may limit the results obtained. Thus, it is desirable to enlarge the design space to account for other information such as drug sequence information, drug activity information, drug semantic information, drug chemical information, drug physical information, and so forth. However, enlarging the design space may increase the complexity of searching the design space.

Accordingly, aspects of the present disclosure generally relate to an artificial intelligence engine for generating candidate drugs. By using various encoding types that enable performing searches in the design space in an efficient manner, the artificial intelligence engine (AI) may enlarge the design space to include the combination of drug information (e.g., structural, physical, semantic, activity, sequence, chemical, etc.). The architecture of the AI engine may include various computational techniques that reduce the computational complexity of using a large design space, thereby saving computing resources (e.g., reducing computing time, reducing processing resources, reducing memory resources, etc.). At the same time, the disclosed architecture may generate superior candidate drugs that include desirable features (e.g., structure, semantics, activity, sequence, clinical outcomes, etc.) found in the larger design space as compared to conventional techniques using the smaller design space.

The artificial intelligence (AI) engine may use a combination of rational algorithmic discovery and machine learning models (e.g., generative deep learning methods) to produce enhanced therapeutics that may treat any suitable target disease or medical condition. The AI engine may discover, translate, design, generate, create, develop, formulate, classify, or test candidate drug compounds that exhibit desired activity (e.g., antimicrobial, immunomodulatory, cytotoxic, neuromodulatory, etc.) in design spaces for target diseases or medical conditions. Such candidate drug compounds that exhibit desired activity in a design space may effectively treat the disease or medical condition associated with that design space. In some embodiments, a selected candidate drug compound that effectively treats the disease or medical condition may be formulated into an actual drug for administration and may be tested in a lab or at a clinical stage.

In general, the disclosed embodiments may enable rationally discovery of drug compounds for a larger design space at a larger scale, higher accuracy, or higher efficiency than conventional techniques. The AI engine may use various machine learning models to discover, translate, design, generate, create, develop, formulate, classify, or test candidate drug compounds. Each of the various machine learning models may perform certain specific operations. The types of machine learning models may include various neural networks that perform deep learning, computational biology, or algorithmic discovery. Examples of such neural networks may include generative adversarial networks, recurrent neural networks, convolutional neural networks, fully connected neural networks, etc., as described further below; and such networks may also additionally employ methods of or incorporating causal inference, including counterfactuals, in the process of discovery.

In some embodiments, a biological context representation of a set of drug compounds may be generated. The biological context representation may be a continuous representation of a biological setting that is updated as knowledge is acquired or data is updated. The biological context representation may be stored in a first data structure having a format (e.g., a knowledge graph) that includes both various nodes pertaining to health artifacts and various relationships connecting the nodes. The nodes and relationships may form logical structures having subjects and predicates. For example, one logical structure between two nodes having a relation may be "Genes are associated with Diseases" where "Genes" and "Diseases" are the subjects of the logical structure and "are associated with" is the relation. In such a way, the knowledge graph may encompass actual knowledge, rather than simply statistical inferences, pertaining to a biological setting.

The information in the knowledge graph may be continuously or periodically updated and the information may be received from various sources curated by the AI engine. The knowledge in the biological context representation goes well beyond "dumb" data that just includes quantities of a value because the knowledge represents the relationships between or among numerous different types of data, as well as any or all of direct, indirect, causal, counterfactual or inferred relationships. In some embodiments, the biological context representation may not be stored, and instead, based on the stream of knowledge included in the biological context representation, may be streamed from data sources into the AI engine that generates the machine learning models.

The biological context representation may be used to generate candidate drug compounds by translating the first data format to a second data structure having a second format (e.g., a vector). The second format may be more computationally efficient or suitable for generating candidate drug compounds that include sequences of ingredients that provide desired activity in a design space. "Ingredients" as used herein may refer, without limitation, to substances, compounds, elements, activities (such as the application or removal of electrical charge or a magnetic field for a specific maximum, minimum or discrete amount of time), and mixtures. Further, the second format may enable generating views of the levels of activity provided by the sequence of ingredients in a certain design space, as described further below.

At a high level, the AI engine may include at least one machine learning model that is trained to use causal inference to generate candidate drug compounds. One of the challenges with discovering new therapeutics may include determining whether certain ingredients may be causal agents with respect to certain activity in a design space. The sheer number of possible sequences of ingredients may be extraordinarily large due to mathematical combinatorics, such that identifying a cause-and-effect relationship between ingredients and activity may be impossible or, at best, extremely unlikely, to identify without the disclosed embodiments. (For example, in public-key encryption, it is theoretically possible to discover and unlock a private key, but doing this would presently require all the computing power in the world to work longer than the age of the universe: this is an example of what is mathematically possible, but impossible within human time frames and computing power. Identifying a cause-and-effect relationship between ingredients and activity, while a different problem, may be similarly mathematically possible, but impossible within human time frames and computer power.) Based on advances in computing hardware (e.g., graphic processing unit processing cores) and the AI techniques using causal inference described herein, the disclosed embodiments may enable the efficient solving of the task of generating candidate drug compounds at scale.

Causal inference may refer to a process, based on conditions of an occurrence of an effect, of drawing a conclusion about a causal connection. Causal inference may analyze a response of an effect variable when a cause is changed. Causation may be defined thusly: a variable X is a cause of Y if Y "listens" to X and determines its response based on what it "hears." The process of causal inference in the field of AI may be particularly beneficial for generating and testing candidate drug compounds for certain diseases or medical conditions because of the use of what are termed counterfactuals. A counterfactual posits and examines conditions contrary to what has actually occurred in reality. For example, if someone takes aspirin for a headache, the headache may go away. The counterfactual asks what would have happened if the person had not taken aspirin, i.e., would the headache still have gone away, or would it have remained or even gotten worse? Accordingly, counterfactuals may refer to calculating alternative scenarios based on past actions, occurrences, results, regressions, regression analyses, correlations, or some combination thereof. A counterfactual may enable determining whether a response should stay the same or instead change if something in a sequence does not occur. For example, one counterfactual may include asking: "Would a certain level of activity be the same if a certain ingredient is not included in a sequence of a candidate drug compound?"

By simulating numerous alternative scenarios to further optimize and hone the accuracy of a sequence of ingredients in the candidate drug compounds, such techniques may enable reducing the number of viable candidate drug compounds. As a result, the embodiments may provide technical benefits, such as reducing resources consumed (e.g., time, processing, memory, network bandwidth) by reducing a number of candidate drug compounds that may be considered for classification as a selected candidate drug compound by another machine learning model.

In some embodiments, one application for the AI engine to design, discover, develop, formulate, create, or test candidate drug compounds may pertain to peptide therapeutics. A peptide may refer to a compound consisting of two or more amino acids linked in a chain. Example peptides may include dipeptides, tripeptides, tetrapeptides, etc. A polypeptide may refer to a long, continuous, and unbranched peptide chain. Peptides may have various structures such as linear, branched, cyclic, peptidomimetic, or nanoparticle. A cyclic peptide may refer to a polypeptide which contains a circular sequence of bonded amino acids. A modified peptide may refer to a synthesized peptide that undergoes a modification to a side chain, C-terminus, or N-terminus. Peptides may be simple to manufacture at discovery scale, include drug-like characteristics of small molecules, include safety and high specificity of biologics, or provide greater administration flexibility than some other biologics.

The disclosed techniques provide numerous benefits over conventional techniques for designing, developing, or testing candidate drug compounds. For example, the AI engine may efficiently use a biological context representation of a set of drug compounds and one or more machine learning models to generate a set of candidate drug compounds and classify one of the set of candidate drug compounds as a selected candidate drug compound. Some embodiments may use causal inference to remove one or more potential candidate drug compounds from classification, thereby reducing the computational complexity and processing burden of classifying a selected candidate drug compound.

In addition, benchmark analysis may be performed for each type of machine learning model that generates candidate drugs. The benchmark analysis may score various parameters of the machine learning models that generate the candidate drugs. The various parameters may refer to candidate drug novelty, candidate drug uniqueness, candidate drug similarity, candidate drug validity, etc. The scores may be used to recursively tune the machine learning models over time to cause one or more of the parameters to increase for the machine learning models. In some embodiments, some of the machine learning models may vary in their effectiveness as it pertains to some of the parameters. In addition, to generate subsequent candidate drug candidates, the benchmark analysis may score the candidate drug candidates generated by the machine learning models, rank the machine learning models that generate the highest scoring candidate drug candidates, or select the machine learning models producing the highest scoring candidate drug candidates.

Solid phase peptide synthesis (SPPS) may refer to a process in which molecules (e.g., amino acids) are covalently bound on a solid support material and synthesized step-by-step in a single reaction vessel. SPPS may include a batch process where one or more steps may be performed in a defined order. In SPPS, multiple iterations of amino acid couplings and deprotections on a solid support enable elongation of a polypeptide chain. SPPS may provide for incorporation of certain combinations of amino acids and may provide therapeutic uses. However, SPPS synthesized peptides and/or proteins may experience secondary events during synthesis, such as aggregation, aspartimide formation, etc. and these secondary events may limit the peptides and/or proteins synthesized using SPPS.

An automated flow synthesis process may refer to automated processes that may improve reaction outcomes relative to batch methods, where the improved reaction outcomes are due to increased heat and/or mass transfer, among other things, in the automated flow synthesis process. Conventionally, it is difficult to determine how synthesis will occur for a sequence of amino acids in a batch or for a flow synthesis process that uses certain parameters (e.g., temperature specification, types of solvents, types of protection groups, types of resin anchors, etc.). Conventional methods for organic reaction development are labor-intensive and require numerous rounds of trial-and-error experimentation, which wastes expensive resources (e.g., amino acids, reagents, solvents, resin anchors, etc.) and/or expensive computing and/or hardware resources (e.g., wear and tear on a processing device, pump, reaction chamber, etc.).

Accordingly, some embodiments of the present disclosure provide a technical solution by fully automating the candidate drug compound generation and the flow process used to synthesize the candidate drug compounds. For example, the artificial intelligence engine may generate optimized synthesizing recipes which enable a sequence to be synthesized by using the automated flow process. The optimized synthesizing recipes may include various attributes of parameters (e.g., temperatures, solvents, resin anchors, etc.) used during synthesis of the candidate drug compounds to optimize the occurrence of desired chemical reactions. Enabling desired chemical reactions to occur during synthesis of a particular sequence of amino acids may result in conserving various resources used during the automated flow process and in generating an enhanced therapeutic compound (e.g., peptide, protein, peptidomemtic, etc.) that provides desired biomedical activity.

Sequences of amino acids, reagents, and/or solvents may be pumped into a reaction chamber at a particular rate and under various conditions (e.g., temperature, pressure) to synthesize the sequence on a solid support material, such as a resin anchor. Some embodiments of the present disclosure enable monitoring each reaction point where a chemical reaction occurs between two amino acids as they couple. Each reaction point may be monitored by a detector that obtains measurement data (e.g., spectral data) including indicators that specify the particular chemical reaction. The measurement data may be obtained in real-time and/or near real-time and transmitted to the artificial intelligence engine. The measurement data may be processed by one or more machine learning models to associate the spectral data with the chemical reaction. In this way, the artificial intelligence engine may learn an association between candidate drug compounds and synthesizing recipes wherein the association as used in practice results in particular chemical reactions. Further, in some embodiments, if the artificial intelligence engine determines a particular chemical reaction occurred during the automated flow process, the artificial intelligence engine may change one or more parameters of a synthesizing recipe in real-time or near real-time. For example, based on a detected chemical reaction, the artificial intelligence engine may change an amount of solvent to be immediately pumped into the reaction chamber to attempt to cause a desired subsequent chemical reaction to occur. Such a technique may enable continuously or continually guiding how a sequence is synthesized such that the desired therapeutic is generated, thereby reducing waste of resources used during the automated flow process.

In some embodiments, a computer-implemented automated flow synthesis platform (also referred to as AF SP herein) that uses the artificial intelligence engine and flow chemistry is disclosed. The sequences included in the candidate drug compounds may be synthesized using the AFSP. The sequences may be proteins such as peptides or peptidomimetics. In some embodiments, the sequences may include canonical amino acids coupled together via amide bonds. An amide bond may refer to a chemical bond included in a main chain of a protein, such as a polypeptide. In some embodiments, the sequences may include non-canonical amino acids coupled together via amide bonds. Amide bonds may occur between an amino-terminus (N-terminus) of a first amino acid where an amino group is free or exposed, and a carboxyl-terminus (C-terminus) of a second amino acid where the carboxyl group is free. The terms "amide bond" and "amide coupling" may be used interchangeably herein. The primary structure of a protein is the linear sequence of amino acids joined together by peptide bonds. Amino acids consist of a common backbone, which allows them to join together in any order, and a variable R group. The variable R group may affect both the structure of the final protein and its function.

The N-terminus and side chain, and the side chain protecting groups, are used during peptide synthesis to avoid undesirable side reactions, such as self-coupling of an activated amino acid leading to polymerization (process of reacting monomer molecules together in a chemical reaction to form polymer chains or three-dimensional networks). Polymerization may prevent the intended peptide coupling reaction, which results in low yield or failure to synthesize the peptide. There are various protecting group schemes that exist for use in peptide synthesis: tert-butyloxycarbonyl protecting group (Boc/Bzl) and fluorenylmethyloxycarbonyl protecting group (Fmoc/tBu). The Boc/Bzl approach utilizes trifluoroacetic acid (TFA)-labile N-terminal tert-butyloxycarbonyl (Boc) protection alongside side chain protection, wherein the trifluoroacetic acid (TFA)-labile N-terminal tert-butyloxycarbonyl (Boc) protection and side chain protection are removed using anhydrous hydrogen fluoride during a final cleavage step (with simultaneous cleavage of the peptide from the solid support). Fmoc/tBu uses base-labile Fmoc N-terminal protection, with side chain protection and a resin linkage that are acid-labile (final acidic cleavage is carried out via TFA treatment). Once the final sequence has been synthesized, a deprotection step may be performed using one or more solvents to remove or cleave the Fmoc protecting group from the sequence. Various side reactions may occur during the deprotection step, and as described herein, one or more detectors may be used to monitor the amide couplings or the deprotection as they occur in real-time or near real-time.

In some embodiments, an enhanced resin may be used as a solid support for the linkage of the sequence chain. The enhanced resin may include at least two linkers in which each link is configured to anchor a particular amino acid. In some embodiments, any number of linkers may be provided by the resin, such that the resin is considered a "universal"

resin. The universal resin may enable the insertion of a single universal resin for any automated flow process, instead of having to change out resins having particular linkers based on the amino acids that are to be synthesized.

The synthesis of the sequences may include coupling a chain of amino acids together to form a polypeptide. The artificial intelligence engine may be communicatively coupled to or included in the AFSP. The AF SP may include certain hardware that enables synthesis of the sequence in an automated flow process. For example, the hardware may include one or more reagent reservoirs, pumps, mixers, heaters, reaction chambers, detectors, and the like. The artificial intelligence engine may include one or more machine learning models trained to output optimized synthesizing recipes. The synthesizing recipes may be optimized in real-time or near real-time to prevent amino acid aggregation (disordered or mis-folded proteins aggregate either intra- or extra-cellularly) or coupling failure. The synthesizing recipes may include one or more attributes of parameters that indicate or specify how to control the automated flow process of synthesizing the sequence.

For example, the attributes of parameters may include solvents, temperature settings of a heater, protection groups, resins (Wang Resin, Fmoc-Pro-DHPP resin, Tricyclic amide linker resin, etc.), resin linkers (Fmoc-2,4-dimethoxy-4'-(carboxymethyloxy)-benzhydrylamine (Rink amide linker), 4-Formyl-3-methoxy-phenoxyacetic acid, 2-Hydroxy-5-dibenzosuberone, 4-Hydroxymethylbenzoic acid (HMBA), 4-Hydroxymethyl-phenoxyacetic acid (HMP linker), 4-(Fmoc-hydrazino)-benzoic acid, 4(4-(1-hydroxyethyl)-2-methoxy-5-nitrophenoxy)-butyric acid, Fmoc-Suberol (5-Fmoc-amino-2-carboxymethoxy-10,11-dihydro-5H-dibenzo[a,d] cycloheptene)), pressure settings of a reaction chamber, and the like. Various hardware may be controlled by the attributes of parameters to enable continuous flow of reactive components or reagents through the reaction chamber as desired. The continuous flow of the reactive components or reagents may enable a steady state to be achieved, such that real-time monitoring of the chemical reactions in the reaction chamber in real-time is enabled using detectors. There are different types of peptide coupling reagents (e.g., carbomiides, aminium/uranium and phosphonium salts, propanephosphonic acid anhydride, etc.), and each may be beneficial for a particular coupling. The attributes of parameters selected in the recipe may themselves be selected by the one or more machine learning models to enable, during synthesis, a specific chemical reaction for each coupling of a terminal amino acid in the sequence chain and a newly added amino acid.

One or more detectors may monitor the synthesis of the sequence in the reaction chamber. The detectors may collect data related to the automated flow process (e.g., hardware settings) to improve peptide synthesis and data related to the peptide (e.g., amide couplings, deprotection, etc.) to enable connecting a peptide sequence and structure to a particular function (e.g., protein-protein, substrate-enzyme, DNA-protein, RNA-protein, or ligand-protein interactions).

During the automated flow process, each amino acid and a solvent may sequentially be pumped into the reaction chamber to synthesize the sequence of amino acids. The one or more detectors may monitor each reaction point (e.g., amide coupling) in the reaction chamber in real-time. The detectors may include various spectral devices, such as an ultra violet (UV)-vis spectrometer, a fluorescence spectrometer, a calorimeter (e.g., heat flow measurement of a chemical reaction or physical change), an infrared spectrometer, a flow cytometry protein interaction assay (FCPIA), a circular dichroism (CD) spectrophotometer (e.g., ultraviolet, visible, and infrared radiation, an electromagnetic spectrometer (e.g., x-ray, ultraviolet, visible, infrared, or microwave wavelengths, a nuclear magnetic resonance (NMR) spectrometer, a high-performance liquid chromatographer high performance liquid spectrometer, florescence spectrometer, Fourier-transform infrared spectrometer, Raman spectrometer, calorimeter, absorption spectrometer, impedance spectrometer, dual polarization interferometer, circular dichroism spectrometer, etc. configured to obtain measurements to include in a spectral profile describing the characteristics of the chemical reaction at the particular reaction point (e.g., amide coupling). The detectors may also include a thermal detector configured to measure the temperature within the reaction chamber. In some embodiments, during synthesis of the sequence, the detectors may monitor analog and digital purification data. The analog data may be a benchmark target purification goal and the digital data may be the measured purification data associated with the sequence. For example, during purification, a certain percentage of the final product may be lost and the yield may be reduced. Using nanopore technology, the disclosed techniques may enable retaining the final product (synthesized sequence) because the final product is small enough to fit through the nanopores, while the byproduct and waste are not. As a result, the byproduct and waste are filtered out, leaving a larger portion of the final product intact. The benchmark target purification goal may be any suitable percentage (e.g., 25 to 50%) yield of final product. To obtain the digital data and determine whether the benchmark target purification goal is met or exceeded, the mass spectrometer may measure the final product during post-purification. Such techniques may enable a reduction in the cost associated with purification and may improve yields. Improving yields may enable the use of less reagents, thereby saving money.

The spectral measurements may represent a length, width, or height of a sequence chain being synthesized. Further, in some embodiments, the mass spectrometer may obtain spectral data that enables determining whether the final product (synthesized sequence) matches the sequence generated by the artificial intelligence engine.

While the detectors observe each reaction point and transmit the measurements obtained to the artificial intelligence engine, numerous parameters, reagents, or sequences may be used during the automated flow process. One or more machine learning models may be trained with training data, where such training data may include a corpus of labeled indicators of the spectral data and corresponding labeled characteristics of chemical reactions. Accordingly, when these trained machine learning models receive the measurements from the detectors in real-time or near real-time during synthesis of a sequence, the machine learning models may determine, based on the spectral data in the measurements, characteristics of the chemical reaction that occurred at a particular reaction point. These characteristics may be associated with certain desired chemical reactions or undesired side reactions, as described further herein. Further, the artificial intelligence engine may train one or more machine learning models to associate the synthesizing recipe (e.g., attributes of parameters) with the characteristics of the chemical reaction for the sequence being synthesized. These trained machine learning models may determine, based on desired chemical reactions, the same or different synthesizing recipes for subsequent sequences to be synthesized.

The spectral data collected during synthesis in the reaction chamber may enable the measurement of side reactions as such side reactions occur. The side reactions may be detected via the spectral data received from the one or more detectors. For example, each side reaction may include various characteristics of a chemical reaction, wherein the various characteristics are associated with a particular spectral profile. Thus, the artificial intelligence engine may determine, based on characteristics associated with received spectral profiles, side reactions that occur during amide coupling in real-time or near real-time in the automated flow process. Example side reactions may include aggregation (e.g., amino acids clump together during synthesis), racemization (e.g., conversion of optically active compounds into a racemic (optically inactive) form), aspartimide formation (e.g., which causes the sequence chain to be terminated during synthesis), cyclization (e.g., presence of a benzyl ester can cause premature cleavage of a chain from insoluble support), glutamic acid side reactions (e.g., deprotection of glutamic acid residues during cleavage can result in the formation of an acylium ion), etc.

In some embodiments, a machine learning model may be trained to receive, as input, a sequence generated by another machine learning model. The machine learning model may determine, based on training data, a synthesizing recipe that has not produced, during synthesis of the sequence, any of the one or more side reactions. The machine learning model may output the synthesizing recipe that has not produced any of the one or more side reactions. If the sequence is synthesized using the synthesized recipe in the automated flow process and a side reaction is detected by the detectors, the machine learning model may be retrained to associate the synthesized recipe for the sequence with the side reaction. As such, the artificial intelligence engine may be continually or continuously trained to generate new sequences or synthesizing recipes until a sequence is synthesized without any side reactions. In other words, to synthesize a sequence, the artificial intelligence "prunes" a "tree" of possible synthesizing recipes quickly by avoiding undesired side reactions and arrives at a synthesizing recipe that results in desired chemical reactions. Such a technique is further enhanced by using a minimum amount of peptide during each synthesis process, as described further herein. As a result, the automated flow process is economically superior to other automated flow processes. Alternatively, the machine learning model may receive a sequence and output a synthesizing recipe that results in a particular side reaction, if desired. Thus, the techniques described herein enable a robust and enhanced automated flow process.

The automated flow process provided by the AFSP may enable improved reaction outcomes due to increased heat and mass transfer as opposed to batch methods, which lack such benefits. In some embodiments, a minimum amount of peptide may be synthesized to enable data collection. Such a technique may reduce waste and resource consumption, as well as save money by limiting the amount of peptide that is produced. For example, in some embodiments, approximately 10-100 micrograms (ug) of peptide may be produced during each automated flow process, and data may be collected from the 10-100 ug of peptide.

Quality control may be performed on the synthesized sequence. The quality control may include performing structural screening or functional screening on the synthesized sequence. The structural and functional data generated during the quality control may be transmitted to the artificial intelligence engine to be associated with the synthesized sequence that was tested. The artificial intelligence engine may retrain one or more machine learning models, such that sequences having desired structural and functional data are subsequently selected. In some embodiments, quality control may be performed on the synthesized sequence that remains attached to the resin. In some embodiments the synthesized peptide may be cleaved from the resin and quality control may be performed on the cleaved synthesized resin.

In some embodiments, using high throughput liquid chromatography mass spectrometer by emitting a laser through the synthesized sequence and measuring chemical reactions, structural screening may be performed on the synthesized sequence. The chemical reactions may indicate properties of the synthesized sequence, such as stability (e.g., whether the synthesized sequence maintains its structure or falls apart). Further, the synthesized sequence may be exposed to a certain amount of light to determine its degradability properties. Such properties may enable determining the synthesized sequence's shelf-life. Certain reducing agents or oxidizing agents may be added to an environment in which the synthesized sequence is present and measurements may be taken to determine how the synthesized sequence reacts. The measurements may indicate additional structural properties of the synthesized sequence.

In some embodiments, functional screening may be performed on the synthesized sequence. The functional screening may implement microarrays, which refer to bidimensional molecular receptor arrays that allow the simultaneous detection of a large number of substances and interactions, and are beneficial for high-throughput analysis. Microarrays may include DNA spots attached to a surface of a solid material. The DNA spots may include fluorescent labels attached to the target DNA fragments. If the particular DNA spots are present in the synthesized sequence when the synthesized sequence is passed over the microarray, the fluorescent label at the associated DNA spot may light up. The synthesized sequences may be analyzed via the microarrays to identify certain protein-protein, substrate-enzyme, DNA-protein, RNA-protein, or ligand-protein interactions. If such interactions occur, various light frequencies, light spectra, or indicators of the microarray analyzing the synthesized sequence may be emitted or actuated. In some embodiments, the structural and functional data may be transmitted to the artificial intelligence engine to train the machine learning models to associate the particular synthesized sequences t analyzed with the structural and functional data. Accordingly, to enhance the generation of subsequent candidate drug compounds, the artificial intelligence engine may continually or continuously learn and evolve its understanding of which sequences are associated with certain structural and functional properties.

Further, if the structural or functional data indicate a desired property in a particular therapeutic application domain (e.g., anti-infective, anti-cancer, anti-microbial, anti-bacterial, etc.), the synthesized sequence may be selected and used in clinical trials.

As further described herein, non-canonical amino acids may be selected and used during synthesis to produce desired sequences, including the non-canonical amino acids. Non-canonical amino acids may incorporate certain ribozymes that introduce a variant codon not present in the genetic code associated with canonical amino acids. However, incorporating a non-canonical amino acid into a sequence may be difficult due to lack of knowledge of chemical reactions that may result during synthesis. For example, non-canonical amino acids may have R groups magnetically charged more electro-negatively or electro-positively that canonical amino acids. Such charged R groups can cause unexpected chemical reactions to occur (e.g., disbursement of electrons at a carboxyl end of a terminal amino acid in a sequence chain during coupling) that may make non-canonical amino acids more difficult to incorporate into sequences than canonical amino acids.

Accordingly, the disclosed techniques enable generating massive amounts of data pertaining to the introduction of non-canonical amino acids into sequences. The massive amounts of data may include the spectral profiles of the chemical reactions that occur each time a non-canonical amino acid is bound to another amino acid (e.g., either canonical or non-canonical). The spectral profiles may be obtained in real-time or near real-time using detectors monitoring the synthesis of the sequences in the reaction chamber. The spectral profiles may indicate characteristics (e.g., whether a chemical reaction occurred, by products, side reactions, etc.) of the chemical reaction that occurs at each amide coupling of the non-canonical amino acid with a terminal amino acid in the sequence chain. In some embodiments, the yields of the sequences including the non-canonical amino acids may be measured, and the resulting yields may be processed by the artificial intelligence engine to determine whether to incorporate the non-canonical amino acid in subsequent sequences to be synthesized in accordance with certain synthesizing recipes.

Further, the artificial intelligence engine may associate the synthesizing recipe used to synthesize the sequence with the resulting characteristics in order to understand how non-canonical amino acids react during an automated flow synthesis process. As a result, sequences, including those containing certain non-canonical amino acids, may be generated by the artificial intelligence engine, and synthesizing recipes for those sequences may be generated that enable synthesizing those sequences (including the non-canonical amino acid) in view of known chemical reactions. The disclosed techniques describe enhanced training of one or more machine learning models using training data including amide coupling data (e.g., amino acids bound by the amide coupling, coupling reagents used to form the amide coupling, etc.), spectral profile data (e.g., various wavelengths of light), or amide coupling fidelity data. The amide coupling fidelity data may provide an indication of a characteristic of the amide coupling, such as strength, quality, successful, unsuccessful, etc. Amide fidelity data may refer to the efficacy of the synthesis, such as an amount of yield and/or effluent. The trained machine learning models may output a synthesizing recipe for synthesizing a sequence including the canonical or non-canonical amino acids.

Quality control may be performed on the synthesized sequences, including the non-canonical amino acids, to determine their biochemical properties (e.g., structural or functional properties). The biochemical properties, determined may be used to retrain one or more machine learning models, such that the machine learning models output subsequent sequences including non-canonical amino acids that provide similar or different biochemical properties, as desired.

Also, certain markets (e.g., anti-infective, animal, industrial, etc.) may prefer, based on a type of data those markets generate, to use certain machine learning models that generate high scores for a subset of parameters. Accordingly, in some embodiments, the subset of machine learning models that generate the high scores for the subset of parameters may be combined into a package and transmitted to a third party. That is, some embodiments enable custom tailoring of machine learning model packages for particular needs of third parties based on their data.

Further, additional benefits of the embodiments disclosed herein may include using the AI engine to produce algorithmically designed drug compounds that have been validated in vivo and in vitro and that provide (i) a broad-spectrum activity against greater than, e.g., 900 multi-drug resistant bacteria, (ii) at least, e.g., a 2-to-10 times improvement in exposure time required to generate a drug resistance profile, (iii) effectiveness across, e.g., four key animal infection models (both Gram-positive and Gram-negative bacteria), or (iv) effectiveness against, e.g., biofilms.

It should be noted that the embodiments disclosed herein may not only apply to the anti-infective market (e.g., for prosthetic joint infections, urinary tract infections, intra-abdominal or peritoneal infections, otitis media, cardiac infections, respiratory infections including but not limited to sequelae from diseases such as cystic fibrosis, neurological infections (e.g., meningitis), dental infections (including periodontal), other organ infections, digestive and intestinal infections (e.g., *C. difficile*), other physiological system infections, wound and soft tissue infections (e.g., cellulitis), etc.), but to numerous other suitable markets or industries. For example, the embodiments may be used in the animal health/veterinary industry, for example, to treat certain animal diseases (e.g., bovine mastitis). Also, the embodiments may be used for industrial applications, such as anti-biofouling, or generating optimized control action sequences for machinery. The embodiments may also benefit a market for new therapeutic indications, such as those for eczema, inflammatory bowel disease, Crohn's Disease, rheumatoid arthritis, asthma, auto-immune diseases and disease processes in general, inflammatory disease progressions or processes, or oncology treatments and palliatives. The video game industry may also benefit from the disclosed techniques to improve the AI used for generating sequences of decisions that non-player characters (NPC) make during gameplay. For example, the knowledge graph may include multiple states of: player characters, non-player characters, levels, settings, actions, results of the actions, and so forth, and, when the states are encountered, one or more machine learning models may use the techniques described herein to generate optimized sequences of decisions for NPCs to make during gameplay. The integrated circuit/chip industry may also benefit from the disclosed techniques to improve the mask works generation and routing processes used for generating the most efficient, highest performance, lowest power, lowest heat generating systems on a chip or solid state devices. For example, the knowledge graph may include configurations of mask works and routings of systems on a chip or solid state drives, as well as their associated properties (e.g., efficiency, performance, power consumption, operating temperature, etc.). The disclosed techniques may generate one or more machine learning models trained using the knowledge graph to generate optimized mask works or routings to achieve desired properties. Accordingly, it should be understood that the disclosed embodiments may benefit any market or industry associated with a sequence (e.g., items, objects, decisions, actions, ingredients, etc.) that can be optimized.

FIGS. 1A through 14, discussed below, and the various embodiments used to describe the principles of this disclosure are by way of illustration only and should not be construed in any way to limit the scope of the disclosure.

FIG. 1A illustrates a high-level component diagram of an illustrative system architecture 100 according to certain embodiments of this disclosure. In some embodiments, the system architecture 100 may include a computing device 102 communicatively coupled to a computing system 116. The computing system 116 may be a real-time software platform, include privacy software or protocols, or include security software or protocols. Each of the computing device 102 and components included in the computing system 116 may include one or more processing devices, memory devices, or network interface cards. The network interface cards may enable communication via a wireless protocol for transmitting data over short distances, such as Bluetooth, ZigBee, NFC, etc. Additionally, the network interface cards may enable communicating data via a wired protocol over short or long distances, and in one example, the computing device 102 and the computing system 116 may communicate with a network 112. Network 112 may be a public network (e.g., connected to the Internet via wired (Ethernet) or wireless (WiFi)), a private network (e.g., a local area network (LAN) or wide area network (WAN)), or a combination thereof. In some embodiments, network 112 may also comprise a node or nodes on the Internet of Things (IoT).

The computing device 102 may be any suitable computing device, such as a laptop, tablet, smartphone, or computer. The computing device 102 may include a display capable of presenting a user interface of an application 118. The application 118 may be implemented in computer instructions stored on the one or more memory devices of the computing device 102 and executable by the one or more processing devices of the computing device 102. The application 118 may present various screens to a user that present various views (e.g., topographical heatmaps) including measures, gradients, or levels of certain types of activity and optimized sequences of selected candidate drug compounds, information pertaining to the selected candidate drug compounds or other candidate drug compounds, options to modify the sequence of ingredients in the selected candidate drug compound, and so forth, as described in more detail below. The computing device 102 may also include instructions stored on the one or more memory devices that, when executed by the one or more processing devices of the computing device 102, perform operations of any of the methods described herein.

In some embodiments, the computing system 116 may include one or more servers 128 that form a distributed computing system, which may include a cloud computing system. The servers 128 may be a rackmount server, a router, a personal computer, a portable digital assistant, a mobile phone, a laptop computer, a tablet computer, a camera, a video camera, a netbook, a desktop computer, a media center, any other device capable of functioning as a server, or any combination of the above. Each of the servers 128 may include one or more processing devices, memory devices, data storage, or network interface cards. The servers 128 may be in communication with one another via any suitable communication protocol. The servers 128 may execute an artificial intelligence (AI) engine 140 that uses one or more machine learning models 132 to perform at least one of the embodiments disclosed herein. The computing system 128 may also include a database 150 that stores data, knowledge, and data structures used to perform various embodiments. For example, the database 150 may store a knowledge graph containing the biological context representation described further below. Further, the database 150 may store the structures of generated candidate drug compounds, the structures of selected candidate drug compounds, and information pertaining to the selected candidate drug compounds (e.g., activity for certain types of ingredients, sequences of ingredients, test results, correlations, semantic information, structural information, physical information, chemical information, etc.). Although depicted separately from the server 128, in some embodiments, the database 150 may be hosted on one or more of the servers 128.

In some embodiments the computing system 116 may include a training engine 130 capable of generating one or more machine learning models 132. Although depicted separately from the AI engine 140, the training engine 130 may, in some embodiments, be included in the AI engine 140 executing on the server 128. In some embodiments, the AI engine 140 may use the training engine 130 to generate the machine learning models 132 trained to perform inferencing operations. The machine learning models 132 may be trained to discover, translate, design, generate, create, develop, classify, or test candidate drug compounds, among other things. The one or more machine learning models 132 may be generated by the training engine 130 and may be implemented in computer instructions executable by one or more processing devices of the training engine 130 or the servers 128. To generate the one or more machine learning models 132, the training engine 130 may train the one or more machine learning models 132. The one or more machine learning models 132 may be used by any of the modules in the AI engine 140 architecture depicted in FIG. 2.

The training engine 130 may be a rackmount server, a router, a personal computer, a portable digital assistant, a smartphone, a laptop computer, a tablet computer, a netbook, a desktop computer, an Internet of Things (IoT) device, any other desired computing device, or any combination of the above. The training engine 130 may be cloud-based, be a real-time software platform, include privacy software or protocols, or include security software or protocols.

To generate the one or more machine learning models 132, the training engine 130 may train the one or more machine learning models 132. The training engine 130 may use a base data set of biological context representation (e.g., physical properties data, peptide activity data, microbe data, antimicrobial data, anti-neurodegenerative compound data, pro-neuroplasticity compound data, clinical outcome data, etc.) for a set of drug compounds. For example, the biological context representation may include sequences of ingredients for the drug compounds. The results may include information indicating levels of certain types of activity associated with certain design spaces. In one embodiment, the results may include causal inference information pertaining to whether certain ingredients in the drug compounds are correlated with or determined by certain effects (e.g., activity levels) in the design space.

The one or more machine learning models 132 may refer to model artifacts created by the training engine 130 using training data that includes training inputs and corresponding target outputs. The training engine 130 may find patterns in the training data wherein such patterns map the training input to the target output and generate the machine learning models 132 that capture these patterns. Although depicted separately from the server 128, in some embodiments, the training engine 130 may reside on server 128. Further, in some embodiments, the artificial intelligence engine 140, the database 150, or the training engine 130 may reside on the computing device 102.

As described in more detail below, the one or more machine learning models 132 may comprise, e.g., a single level of linear or non-linear operations (e.g., a support vector machine (SVM) or the machine learning models 132 may be a deep network, i.e., a machine learning model comprising multiple levels of non-linear operations. Examples of deep networks are neural networks, including generative adversarial networks, convolutional neural networks, recurrent neural networks with one or more hidden layers, and fully connected neural networks (e.g., each artificial neuron may transmit its output signal to the input of the remaining neurons, as well as to itself). For example, the machine learning model may include numerous layers or hidden layers that perform calculations (e.g., dot products) using various neurons. In some embodiments, one or more of the machine learning models 132 may be trained to use causal inference and counterfactuals.

For example, the machine learning model 132 trained to use causal inference may accept one or more inputs, such as (i) assumptions, (ii) queries, and (iii) data. The machine learning model 132 may be trained to output one or more outputs, such as (i) a decision as to whether a query may be answered, (ii) an objective function (also referred to as an estimand) that provides an answer to the query for any received data, and (iii) an estimated answer to the query and an estimated uncertainty of the answer, where the estimated answer is based on the data and the objective function, and the estimated uncertainty reflects the quality of data (i.e., a measure which takes into account the degree or salience of incorrect data or missing data). The assumptions may also be referred to as constraints and may be simplified into statements used in the machine learning model 132. The queries may refer to scientific questions for which the answers are desired.

The answers estimated using causal inference by the machine learning model may include optimized sequences of ingredients in selected candidate drug compounds. As the machine learning model estimates answers (e.g., candidate drug compounds), certain causal diagrams may be generated, as well as logical statements, and patterns may be detected. For example, one pattern may indicate that "there is no path connecting ingredient D and activity P," which may translate to a statistical statement "D and P are independent." If alternative calculations using counterfactuals contradict or do not support that statistical statement, then the machine learning model 132 or the biological context representation may be updated. For example, another machine learning model 132 may be used to compute a degree of fitness which represents a degree to which the data is compatible with the assumptions used by the machine learning model that uses causal inference. There are certain techniques that may be employed by the other machine learning model 132 to reduce the uncertainty and increase the degree of compatibility. The techniques may include those for maximum likelihood, propensity scores, confidence indicators, or significance tests, among others.

In some embodiments, a generative adversarial network (GAN) may generate a set of candidate drug compounds without using causal inference. In some embodiments, the GAN may generate a set of candidate drug compounds using causal inference. A GAN refers to a class of deep learning algorithms including two neural networks, a generator and a discriminator, that both compete with one another to achieve a goal. For example, regarding candidate drug compound generation, the generator goal may include generating candidate drug compounds, including compatible/incompatible sequences of ingredients, and effective/ineffective sequences of ingredients, etc. that the discriminator classifies as feasible candidate drug compounds, including compatible and effective sequences of ingredients that may produce desired activity levels for a design space. In one embodiment, the generator may use causal inference, including counterfactuals, to calculate numerous alternative scenarios that indicate whether a certain result (e.g., activity level) still follows when any element or aspect of a sequence changes. For example, the generator may be a neural network based on Markov models (e.g., Deep Markov Models), which may perform causal inference. In some embodiments, one or more of the counterfactuals used during the causal inference may be determined and provided by the scientist module. The discriminator goal may include distinguishing candidate drug compounds which include undesirable sequences of ingredients from candidate drug compounds which include desirable sequences of ingredients.

In some embodiments, the generator initially generates candidate drug compounds and continues to generate better candidate drug compounds after each iteration until the generator eventually begins to generate candidate drug compounds that are valid drug compounds which produce certain levels of activity within a design space. A candidate drug compound may be "valid" when it produces a certain level of effectiveness (e.g., above a threshold activity level as determined by a standard (e.g., regulatory entity)) in a design space. In order to classify the candidate drug compounds as a valid drug compound or invalid candidate drug compound, the discriminator may receive real drug compound information from a dataset and the candidate drug compounds generated by the generator. "Real drug compound," as used in this disclosure, may refer to a drug compound that has been approved by any regulatory (governmental) body or agency. The generator obtains the results from the discriminator and applies the results in order to generate better (e.g., valid) candidate drug compounds.

General details regarding the GAN are now discussed. The two neural networks, the generator and the discriminator, may be trained simultaneously. The discriminator may receive an input and then output a scalar indicating whether a candidate drug compound is an actual or viable drug compound. In some embodiments, the discriminator may resemble an energy function that outputs a low value (e.g., close to 0) when input is a valid drug compound and a positive value when the input is not a valid drug compound (e.g., if it includes an incorrect sequence of ingredients for certain activity levels pertaining to a design space).

There are two functions that may be used, the generator function (G(V)), and the discriminator function (D(Y)). The generator function may be denoted as G(V), where V is generally a vector randomly sampled in a standard distribution (e.g., Gaussian). The vector may be any suitable dimension and may be referred to as an embedding herein. The role of the generator is to produce candidate drug candidates to train the discriminator function (D(Y)) to output the values indicating the candidate drug candidate is valid (e.g., a low value), where Y is generally a vector referred to as an embedding and where, further, Y may include candidate drug compounds or real drug compounds.

During training, the discriminator is presented with a valid drug compound and adjusts its parameters (e.g., weights and biases) to output a value indicative of the validity of the candidate drug compounds that produce real activity levels in certain design spaces. Next, the discriminator may receive a modified candidate drug compound (e.g., modified using counterfactuals) generated by the generator and adjust its parameters to output a value indicative of whether the modified candidate drug compound provides the same or a different activity level in the design space.

The discriminator may use a gradient of an objective function to increase the value of the output. The discriminator may be trained as an unsupervised "density estimator," i.e., a contrast function produces a low value for desired data (e.g., candidate drug compounds that include sequences producing desired levels of certain types of activity in a design space) and higher output for undesired data (e.g., candidate drug compounds that include sequences producing undesirable levels of certain types of activity in a design space). The generator may receive the gradient of the discriminator with respect to each modified candidate drug compound it produces. The generator uses the gradient to train itself to produce modified candidate drug compounds that the discriminator determines include sequences producing desired levels of certain types of activity in a design space.

Recurrent neural networks include the functionality, in the context of a hidden layer, to process information sequences and store information about previous computations. As such, recurrent neural networks may have or exhibit a "memory." Recurrent neural networks may include connections between nodes that form a directed graph along a temporal sequence. Keeping and analyzing information about previous states enables recurrent neural networks to process sequences of inputs to recognize patterns (e.g., such as sequences of ingredients and correlations with certain types of activity level). Recurrent neural networks may be similar to Markov chains. For example, Markov chains may refer to stochastic models describing sequences of possible events in which the probability of any given event depends only on the state information contained in the previous event. Thus, Markov chains also use an internal memory to store at least the state of the previous event. These models may be useful in determining causal inference, such as whether an event at a current node changes as a result of the state of a previous node changing.

The set of candidate drug compounds generated may be input into another machine learning model 132 trained to classify of the set of candidate drug compounds as a selected candidate drug compound. The classifier may be trained to rank the set of candidate drug compounds using any suitable ranking (i.e., for example, non-parametric) technique. For example, in some embodiments, one or more clustering techniques may be used to cluster the set of candidate drug compounds. To classify the selected candidate drug compound, the machine learning model 132 may also perform objective optimization techniques while clustering. To classify the selected candidate drug compound having desired levels of certain types of activity, the objective optimization may include using a minimization or maximization function for each candidate drug compound in the clusters.

A cluster may refer to a group of data objects similar to one another within the same cluster, but dissimilar to the objects in the other clusters. Cluster analysis may be used to classify the data into relative groups (clusters). One example of clustering may include K-means clustering where "K" defines the number of clusters. Performing K-means clustering may comprise specifying the number of clusters, specifying the cluster seeds, assigning each point to a centroid, and adjusting the centroid.

Additional clustering techniques may include hierarchical clustering and density based spatial clustering. Hierarchy clustering may be used to identify the groups in the set of candidate drug compounds where there is no set number of clusters to be generated. As a result, a tree-based representation of the objects in the various groups may be generated. Density-based spatial clustering may be used to identify clusters of any shape in a dataset having noise and outliers. This form of clustering also does not require specifying the number of clusters to be generated.

Figure 1B:
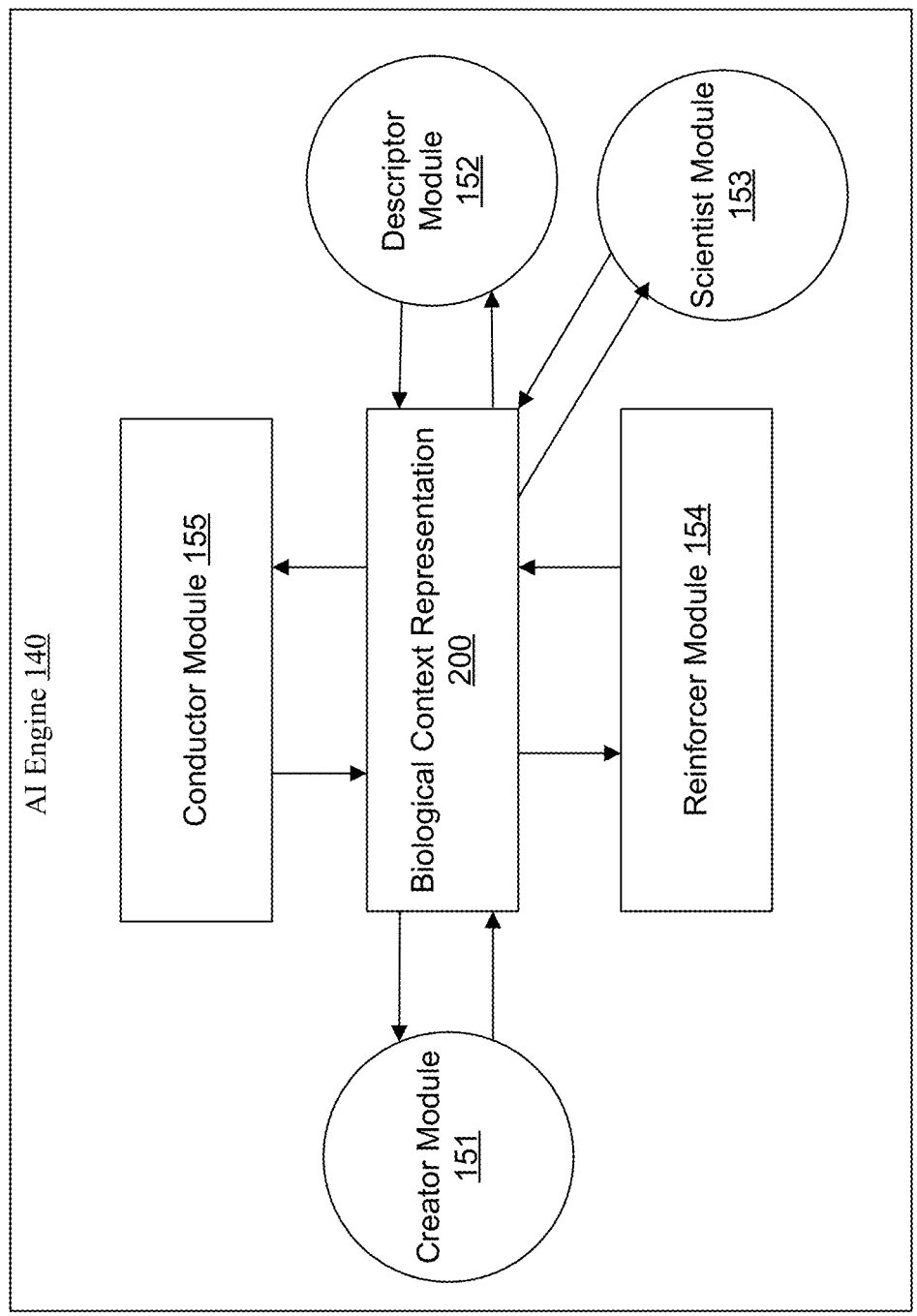
FIG. 1B illustrates an architecture of the artificial intelligence engine according to certain embodiments of this disclosure.

FIG. 1B illustrates an architecture of the artificial intelligence engine according to certain embodiments of this disclosure. The architecture may include a biological context representation 200, a creator module 151, a descriptor module 152, a scientist module 153, a reinforcer module 154, and a conductor module 155. The architecture may provide a platform that improves its machine learning models over time by using benchmark analysis to produce enhanced candidate drug compounds for target design spaces. The platform may also continuously or continually learn new information from literature, clinical trials, studies, research, or any suitable data source about drug compounds. The newly learned information may be used to continuously or continually train the machine learning models to evolve with evolving information.

The biological context representation 200 may be implemented in a general manner such that it can be applied to solve different types of problems across different markets. The underlying structure of the biological context representation 200 may include nodes and relationships between the nodes. There may be semantic information, activity information, structural information, chemical information, pathway information, and so forth represented in the biological context representation 200. The biological context representation 200 may include any number of layers of information (e.g., five layers of information). The first layer may pertain to molecular structure and physical property information, the second layer may pertain to molecule-to-molecule interactions, the third layer may pertain to molecule pathway interactions, the fourth layer may pertain to molecule cell profile associations, and the fifth layer may pertain to therapeutics (including those using biologics) and indications relevant for molecules. The biological context representation 200 is discussed further below with reference to FIGS. 2 and 5.

Further, to increase computing processing using various encodings, those various encodings may be selected to preferentially represent certain types of data. For example, to effectively capture common backbone structures of molecules, Morgan fingerprints may be used to describe physical properties of the candidate drug compounds. The encodings are discussed further below with reference to FIG. 1G.

Although just one creator module 151 is depicted, there may any suitable number of creator modules 151. Each of the creator modules 151 may include one or more generative machine learning models trained to generate new candidate drug compounds. The new candidate drug compounds are then added to the biological context representation 200. To that end, the term "creator module" and "generative model" may be used interchangeably herein. Each node in the biological context representation 200 may be a candidate drug compound (e.g., a peptide candidate).

The generative machine learning modules included in the creator module 151 may be of different types and perform different functions. The different types and different functions may include a variational autoencoder, structured transformer, Mini Batch Discriminator, dilation, self-attention, upsampling, loss, and the like. Each of these generative machine learning model types and functions is briefly explained below.

Regarding the variational autoencoder, it may simultaneously train two machine learning models, an inference model $q_\varphi(z|x)$ and a generative model $p_\Theta(x|z)p_\Theta(z)$ for data x and a latent variable z. In some embodiments, both the inference model and the generative model may be conditioned on a chosen attribute of the sequences. Both models may be jointly optimized using a tractable variational Bayesian approach which maximizes the evidence lower bound (ELBO).

Regarding the structured transformer, it may perform autoregressive decomposition to decompose the joint probability distribution of the sequence given a structure autoregressively as:

$$p(s|x) = \Pi_i p(s_i|x_{<i})$$

The conditional probability $p(s_i|x_{<i})$ of amino acid $s_i$ at position i is conditioned on both the input structure x and the preceding amino acid $s_i$ and the preceding amino acid $s_{<i} = \{s_1, \ldots s_{i-1}\}$. These conditionals may be parameterized in terms of two sub-networks: an encoder that computes embeddings from structure-based features and edge features, and a decoder that autoregressively predicts amino acid letter $s_i$ given the preceding sequence and structural embeddings from the encoder.

Mode collapse occurs in generative adversarial networks when the generator generates a limited diversity of samples, or even the same sample, regardless of the input. To overcome mode collapse, some embodiments implement a Mini Batch Discriminator (MBD) approach. MBDs each work as an extra layer in the network that computes the standard deviation across the batch of examples (the batch contains only real drug compounds or only candidate drug compounds). If the batch contains a small variety of examples, the standard deviation will be low, and the discriminator will be able to use this information to lower the score for each example in the batch. To further reduce mode collapse occurrence, some embodiments balance the sampling frequency of the training dataset clusters.

Regarding dilation, convolution filters may be capable of detecting local features, but they have limitations when it comes to relationships separated by long distances. Accordingly, some embodiments implement convolution filters with dilation. By introducing gaps into convolution kernels, such techniques increase the receptive field without increasing the number of parameters. Dilation rate may be applied to one convolution filter in each residual block of a generator or a discriminator. In this way, by the last layer of the generative adversarial network, filters may include a large enough receptive field to learn relationships separated by long-distances. Residual blocks are discussed further below with reference to FIGURE 1F.

Regarding self-attention, different areas of a protein have different associations and effects on overall protein behavior. Accordingly, the architecture of the generative adversarial network disclosed herein implements a self-attention mechanism. The self-attention mechanism may include a number of layers that highlight different areas of importance across the entire sequence and allow the discriminator to determine whether parts in distant portions of the protein are consistent with each other.

Regarding upsampling, some embodiments implement techniques best suited for protein generation. For example, nearest-neighbor interpolation, transposed convolution, and sub-pixel convolution may be used. During candidate drug compound generation, sub-pixel convolution may be used to increase resolution of a design space. Any combination of these techniques may be used in the upsampling layers. In some embodiments, transposed convolution by itself may be used for all upsampling layers.

Regarding the loss function, it is a component that aids in the successful performance of a neural network. Various losses, such as non-saturating, non-saturating with RI regularization, hinge, hinge with relativistic average, and Wasserstein and Wasserstein with gradient penalty losses, may be used. In some embodiments, due to performance increases, the non-saturating loss with RI regularization may be used for the generative adversarial network.

Details pertaining to the architecture of the creator module 151 are described below with reference to FIGS. 1C-1I.

The descriptor module 152 may include one or more machine learning models trained to generate descriptions for each of the candidate drug compounds generated by the creator module 151. The descriptor module 152 may be trained to use different encodings to represent the different types of information included in the candidate drug compound. The descriptor module 152 may populate the information in the candidate drug compound with ordinal values, cardinal values, categorical values, etc. depending on the type of information. For example, the descriptor module 152 may include a classifier that analyzes the candidate drug compound and determines whether it is a cancer peptide, an antimicrobial peptide, or a different peptide. The descriptor module 152 describes the structure and the physiochemical properties of the candidate drug compound.

The reinforcer module 154 may include one or more machine learning models trained to analyze, based on the descriptions, the structure and the physiochemical properties of the candidate drug compounds in the biological context representation 200. Based on the analysis, the reinforcer module 154 may identify a set of experiments to perform on the candidate drug compounds to elicit certain desired data (e.g., activity effectiveness, biomedical features, etc.). The identification may be performed by matching a pattern of the structure and physiochemical properties of the candidate drug compounds with the structure and physiochemical properties of other drug compounds and determining which experiments were performed on the other drug compounds to elicit desired data. The experiments may include in vitro or in vivo experiments. Further, the reinforcer module 154 may identify experiments that should not be performed for the candidate drug compounds if a determination is made that those experiments yield useless data for drug compounds.

The conductor module 155 may include one or more machine learning models trained to perform inference queries on the data stored in the biological context representation 200. The inference queries may pertain to performing queries to improve the quality of the data in the biological context representation 200. For example, there may be a gap in data in one of the nodes (e.g., candidate drug compounds) stored in the biological context representation 200. An inference query refers to the process of identifying a first node and a second node similar to the first node, and to obtaining data from the second node to fill a data gap in the first node. An inference query may be executed to search for another node having similarities to the node with the gap and may fill the gap with the data from the other node.

The scientist module 153 may include one or more machine learning models trained to perform benchmark analysis to evaluate various parameters of the creator module 151. In some embodiments, the scientist module 153 may generate scores for the candidate compound drugs generated by the creator module 151. The benchmark analysis may be used to electronically and recursively optimize the creator module 151 to generate candidate drug compounds having improved scores in subsequent generation rounds. There may be several types of benchmarks (e.g., distribution learning benchmarks, goal-directed benchmarks, etc.) used by the scientist module 153 to evaluate generative machine learning models used by the creator module 151. As described herein, one or more parameters (e.g., validity, uniqueness, novelty, Frechet ChemNet Distance (FCD), internal diversity, Kullback-Leibler (KL) divergence, similarity, rediscovery, isomer capability, median compounds, etc.) of the creator module 151 may be scored during benchmark analysis. The benchmark analysis may also be used to electronically and recursively optimize the creator module 151 to improve scores of the parameters in subsequent generation rounds. Any combination of the benchmarks described below may be used to evaluate the creator module 151.

One type of benchmark used by the scientist module 153 may include a distribution learning benchmark. The distribution learning benchmark evaluates, when given a set of molecules, how well the creator module 151 generates new molecules which follow the same chemical distribution. For example, when provided with therapeutic peptides, the distribution learning benchmark evaluates how well the creator module 151 generates other therapeutic peptides having similar chemical distributions.

The distribution learning benchmark may include generating a score for an ability of the creator module 151 to generate valid candidate drug compounds, a score for an ability of the creator module 151 to generate unique candidate drug compounds, a score for an ability of the creator module 151 to generate novel candidate drug compounds, a Frechet ChemNet Distance (FCD) score for the creator module 151, an internal diversity score for the creator module 151, a KL divergence score for the creator module 151, and so forth. Each of the distribution learning benchmarks is now discussed.

The validity score may be determined as a ratio of valid candidate drug compounds to non-valid candidate drug compounds of generated candidate drug compounds. In some embodiments, the ratio may be determined from a certain number (e.g., 10,000) of candidate drug compounds. In some embodiments, candidate drug compounds may be considered valid if their representation (e.g., simplified molecular-input line-entry system (SMILES)) can be successfully parsed using any suitable parser.

The uniqueness score may be determined by sampling candidate drug compounds generated by the creator module 151 until a certain number (e.g., 10,000) of valid molecules are identified by identical representations (e.g., canonical SMILES strings). The uniqueness score may be determined as the number of different representations divided by the certain number (e.g., 10,000).

The novelty score may be determined by generating candidate drug compounds until a certain number (e.g., 10,000) of different representations (e.g., canonical SMILES strings) are obtained and computing the ratio of candidate drug compounds (including real drug compounds) not present in the training dataset.

The Frechet ChemNet Distance (FCD) score may be determined by selecting a random subset of a certain number (e.g., 10,000) of drug compounds from the training dataset, and generating candidate drug compounds using the creator module 151 until a certain number (10,000) of valid candidate drug compounds are obtained. The FCD between the subset of the drug compounds and the candidate drug compounds may be determined. The FCD may consider chemically and biologically relevant information about drug compounds, and also measure the diversity of the set via the distribution of generated candidate drug compounds. The FCD may detect if generated candidate drug compounds are diverse, and the FCD may detect if generated candidate drug compounds have similar chemical and biological properties as real drug compounds. The FCD score ("S") is determined using the following relationship: $S = \exp(-0.2*FCD)$.

The internal diversity score may assess the chemical diversity within a set of generated candidate drug compounds ("GROUP"). The internal diversity score may be determined using the following relationship:

$$IntDiv_p(G) = 1 - \sqrt[p]{\frac{1}{|G|^2} \sum_{(m_1, m_2) \in G} T(m_1, m_2)^p}$$

In the above equation, $T(m_1, m_2)$ is the Tanimoto Similarity (SNN) between molecule 1, $m_1$, and molecule 2, $m_2$. Variable G is the set of candidate drug compounds and variable P is the set number of groups being tested. While SNN measures the dissimilarity to external diversity, the internal diversity score may consider dissimilarity between generated candidate drug compounds. The internal diversity score may be used to detect mode collapse in certain generative models. For example, mode collapse may occur when the generative model produces a limited variety of candidate drug compounds while ignoring some areas of a design space. A higher score for the internal diversity corresponds to higher diversity in the set of candidate drug compounds generated.

The KL divergence score may be determined by calculating physiochemical descriptors for both the candidate drug compounds and the real drug compounds. Further, a determination may be made of the distribution of maximum nearest neighbor similarities on fingerprints (e.g., extended connectivity fingerprint of up to four bonds (ECFP4)) for both the candidate drug compounds and the real drug compounds. The distribution of these descriptors may be determined via kernel density estimation for continuous descriptors, or as a histogram for discrete descriptors. The KL divergence $D_{KL,i}$ may be determined for each descriptor i, and is aggregated to determine the KL divergence score S via:

$$S = \frac{1}{k} \sum_i^k \exp(-D_{KL,i})$$

Where k is the number of descriptors (e.g., k=9).

The isomer capability score may be determined by whether molecules may be generated that correspond to a target molecular formula (for example C7H8N2O2). The isomers for a given molecular formula can in principle be enumerated, but except for small molecules this number will in general be very large. The isomer capability score represents fully-determined tasks that assess the flexibility of the creator module to generate molecules following a simple pattern (which is a priori unknown).

A second type of benchmark may include a goal-directed benchmark. The goal-direct benchmark may evaluate whether the creator module 151 generates a best possible candidate drug compound to satisfy a pre-defined goal (e.g., activity level in a design space). A resulting benchmark score may be calculated as a weighted average of the candidate drug compound scores. In some embodiments, the candidate drug compounds with the best benchmark scores may be assigned a larger weight. As such, generative models of the creator module 151 may be tuned to deliver a few candidate drug compounds with top scores, while also generating candidate drug compounds with satisfactory scores. For each of the goal-directed benchmarks, one or several average scores may be determined for the given number of top candidate drug compounds and then the resulting benchmark score may be calculated as the mean of these average scores. For example, the resulting benchmark score may be a combination of the top-1, top-10, and top-100 scores, in which the resulting benchmark score is determined by the following relationship:

$$IntDiv_p(G) = 1 - \sqrt[p]{\frac{1}{|G|^2} \sum_{m_1, m_2 \in G} T(m_1, m_2)^p}$$

Where s is an n-dimensional (e.g., 100-dimensional) vector of candidate drug compound scores $s_v$, $1 \leq i \leq 100$ sorted in decreasing order (e.g., $s_i \geq s_j$ for i<j). Variable G is the set of candidate drug compounds and variable P is the set number of groups being tested.

The goal-directed benchmark may include generating a score for an ability of the creator module 151 to generate candidate drug compounds similar to a real drug compound, a score for an ability of the creator module 151 to rediscover the potential viability of previously-known drug compounds (e.g., using a drug which is prescribed for certain conditions for a new condition or disease), and the like.

The similarity score may be determined using nearest neighbor scoring, fragment similarity scoring, scaffold similarity scoring, SMARTS scoring, and the like. Nearest neighbor scoring (e.g., nns(G, R)) may refer to a scoring function that determines the similarity of the candidate drug compound to a target real drug compound g. The score corresponds to the Tanimoto similarity when considering the fingerprint r and may be determined by the following relationship:

$$NNS(G, R) = \frac{1}{|G|} \sum_{m_G \ in \ G}^{max} T(m_G m_R)$$

Where $m_R$ and $m_G$ are representations of the real drug compounds (R) and the candidate drug compounds (G) as bit strings (e.g., digital fingerprints, e.g., outputs of hash functions, etc.). The resulting score reflects how similar candidate drug compounds are to real drug compounds in terms of chemical structures encoded in these fingerprints. In some embodiments, Morgan fingerprints may be used with a radius of a configurable value (e.g., 2) and an encoding with a configurable number of bits (e.g., 1024). The radius and encoding bits may be configured to produce desirable results in a biochemical space.

The similarity score may be determined using fragment similarity scoring, which itself may be defined as the cosine distance between vectors of fragment frequencies. For a set of candidate drug compounds (G), its fragment frequency vector $f_G$ has a size equal to the size of all chemical fragments in the dataset, and elements of $f_G$ represent frequencies with which the corresponding fragments appear in G. The distance is determined by the following relationship:

$$Frag(G,R)=1-\cos(f_G f_R)$$

Candidate drug compounds and real drug compounds may be fragmented using any suitable decomposition algorithm. The fragment similarity scoring score represents the similarity of the set of candidate drug compounds and the set of real drug compounds at the level of chemical fragments.

The similarity score may be determined using scaffold similarity scoring, which may be determined in a similar way to the fragment similarity scoring. For example, the scaffold similarity scoring may be determined as a cosine similarity between vectors $s_G$ and $s_R$ that represent frequencies of scaffolds in a set of candidate drug compounds (G) and a set of real drug compound (R). The scaffold similarity scoring score may be determined by the following relationship $$Frag(G,R)=1-\cos(s_G s_R).$$

The similarity score may be determined using SMARTS scoring. SMARTS scoring may be implemented according to the relationship: SMART (a, b). The SMARTS scoring may evaluate whether the SMARTS pattern s is present in a candidate drug compound. $b$ is a Boolean value indicating whether the SMARTS pattern should be present (true) or absent (false). When the pattern is desired, a score of 1, for true, is returned if the SMARTS pattern is found. If the pattern is not found, then a score of 0, for false, is returned.

In some embodiments, a goal-directed benchmark may include determining a rediscovery score for the creator module 151. In some embodiments, certain real drug compounds may be removed from the training dataset and the creator module 151 may be retrained using the modified training set lacking the removed real drug compounds. If the creator module 151 is able to generate ("rediscover") a candidate drug compound that is identical or substantially similar to the removed real drug compounds, then a high rediscovery score may be assigned. Such a technique may be used to validate the creator module 151 is effectively trained or tuned.

Various modifiers may be used to modify the scores for the various benchmarks discussed above. For example, a Gaussian modifier may be implemented to target a specific value of some property, while giving high scores when the underlying value is close to the target. It may be adjustable as desired. A minimum Gaussian modifier may correspond to the right half of a Gaussian function and values smaller than a threshold may be given a full score, while values larger than the threshold decrease continuously to zero. A maximum Gaussian modifier may correspond to a left half of the Gaussian function and values larger than the threshold are given a full score, while values smaller than the threshold decrease continuously to zero. A threshold modifier may attribute a full score to values above a given threshold, while values smaller than the threshold decrease linearly to zero.

There are a variety of competing generative models that may be used to evaluate the performance of the creator module 151. For example, the competing generative models may include a random sampling, best of dataset method, SMILES genetic algorithm (GA), graph GA, graph Monte-Carlo tree search (MCTS), SMILES long short-term memory (LSTM), character-level recurrent neural networks (CharRNN), variational autoencoder, adversarial autoencoder, Latent generative adversarial network (LatentGAN), junction tree variational autoencoder (JT-VAE), and objective-reinforced generative adversarial network (ORGAN). Each of these competing generative models will now be discussed briefly.

Regarding random sampling, this baseline samples at random the requested number of molecules (candidate drug compounds) for the dataset. Random sampling may provide a lower bound for the goal-directed benchmarks, because no optimization is performed to obtain the returned molecules.

Random sampling may provide an upper bound for the distribution learning benchmarks, because the molecules returned may be taken directly for the original distribution.

Regarding best of dataset method (or "best of dataset" herein), one goal of de novo molecular design is to explore unknown parts of the biochemical space, generating new candidate drug compounds with better properties than the drug compounds already known. The best of dataset scores the entire generated dataset including the candidate drug compounds with a provided scoring function and returns the highest scoring molecules. This effectively provides a lower bound for the goal-directed benchmarks that enables the creator module 151 to create better candidate drug compounds than the real or candidate drug compounds provided.

Regarding SMILES GA, this technique may evolve string molecular representations using mutations exploiting the SMILES context-free grammar. For each goal-directed benchmark, a certain number (e.g., 300) of highest scoring molecules in the dataset may be selected as an initial population. In this example, each molecule is represented by 300 genes. During each epoch an offspring of a certain number (e.g., 600) of new molecules may be generated by randomly mutating the population molecules. After deduplication and scoring, these new molecules may be merged with the current population and a new generation is chosen by selecting the top scoring molecules overall. This process may be repeated a certain number of times (e.g., 1000) or until progress has stopped for a certain number (e.g., 5) of consecutive epochs. Distribution-learning benchmarks do not apply to this baseline.

Regarding graph GA, this GA involves molecule evolution at the graph level. For each goal-directed benchmark a certain number (e.g., 100) of highest scoring molecules in the dataset are selected as the initial population. During each epoch, a mating pool of a certain number (e.g., 200) of molecules is sampled with replacement from the population, using scores as weights. This pool may contain many repeated molecules if their score is high. A new population of a certain number (e.g., 100) is then generated by iteratively choosing two molecules at random from the mating pool and applying a crossover operation. With probability of, e.g., 0.5 (i.e., 100/200), a mutation is also applied to the offspring molecule. This process is repeated a certain number (e.g., 1000) of times or until progress has stopped for a certain number (e.g., 5) of consecutive epochs. Distribution-learning benchmarks do not apply to this baseline.

Regarding graph MCTS, the statistics used during sampling may be computed on the training dataset. For this baseline, no initial population is selected for the goal-directed benchmarks. Each new molecule may be generated by running a certain number (e.g., 40) of simulations, starting from a base molecule. At each step, a certain number (e.g., 25) of children are considered and the sampling stops when reaching a certain number (e.g., 60) of atoms. The best-scoring molecule found during the sampling may be returned. A population of a certain number (e.g., 100) of molecules is generated at each epoch. This process may be repeated a certain number (e.g., 1000) of times or until progress has stopped for a certain number (e.g., 5) of consecutive epochs. For the distribution learning benchmark. the generation starts from a base molecule and a new molecule is generated with the same parameters. As for the goal-directed benchmarks, the only difference is that no scoring function is provided, so the first molecule to reach terminal state is returned instead of the highest scoring molecule.

Regarding SMILES LSTM, the technique is a baseline model, consisting of an LSTM neural network which predicts the next character of partial SMILES strings. In some embodiments, a SMILES LSTM may be used with 3 layers of hidden size of 1024. For the goal-directed benchmarks, a certain number (e.g., 20) of iterations of hill-climbing may be performed; at each step the model generated a certain number (e.g., 8192) of molecules and a certain number (e.g., 1024) of the top scoring molecules may be used to fine-tune the model parameters. For the distribution-learning benchmark, the model may generate the requested number of molecules.

Regarding character-level recurrent neural networks (CharRNN), the technique treats the task of generating SMILES as a language model attempting to learn the statistical structure of SMILES syntax by training it on a large corpus of SMILES. The CharRNN parameters may be optimized using maximum likelihood estimation (MLE). In some embodiments, CharRNN may be implemented using LSTM RNN cells stacked into a certain number of layers (e.g., 3 layers) with a certain number of hidden dimensions (e.g., 600 hidden dimensions). In some embodiments, to prevent overfitting, a dropout layer with a certain dropout probability (e.g., p=0.2) may be added between intermediate layers. Training may be performed with a batch size of a certain number (e.g., 64) using an optimizer.

Regarding a variational autoencoder (VAE), it is a framework for training two neural networks, an encoder and a decoder, to learn a mapping from a higher-dimensional data representation (e.g., vector) into a lower-dimensional data representation and from the lower-dimensional data representation back to the higher-dimensional data representation. The lower-dimensional space is called the latent space, which is often a continuous vector space with normally distributed latent representation. The latent representation of our data may contain all the important information needed to represent an original data point. The latent representation represents the features of the original data point. In other words, one or more machine learning models may learn the data features of the original data point and simplify its representation to make it more efficient to analyze. VAE parameters may be optimized to encode and decode data by minimizing the reconstruction loss while also minimizing a KL-divergence term arising from the variational approximation, such that the KL-divergence term may loosely be interpreted as a regularization term. Since molecules are discrete objects, properly trained VAE defines an invertible continuous representation of a molecule.

In some embodiments, aspects from both implementations may be combined. The encoder may implement a bidirectional Gated Recurrent Unit (GRU) with a linear output layer. The decoder may be a 3-layer GRU RNN of 512 hidden dimensions with intermediate dropout layers, the layers having a dropout probability of 0.2. Training may be performed with a batch size of a certain number (e.g., 128), utilizing a gradient clipping of 50 and a KL-term weight of 1, and further optimized with a learning rate of 0.0003 across 50 epochs. Other training parameters may be used to perform the embodiments disclosed herein.

Regarding adversarial autoencoders (AAE), they combine the idea of VAE with that of adversarial training as found in a GAN. In AAE, the KL divergence term is avoided by training a discriminator network to predict whether a given sample came from the latent space of the AE or from a prior distribution of the autoencoder (AE). Parameters may be optimized to minimize the reconstruction loss and to minimize the discriminator loss. The AAE model may consist of an encoder with a 1-layer bidirectional LSTM with 380 hidden dimensions, a decoder with a 2-layer LSTM with 640 hidden dimensions and a shared embedding of size 32. The latent space is of 640 dimensions, and the discriminator networks is a 2-layer fully connected neural network with 640 and 256 nodes respectively, utilizing the ELU activation function. Training may be performed with a batch size of 128, with an optimizer using a learning rate of 0.001 across 25 epochs. Other training parameters may be used to perform the embodiments disclosed herein.

Regarding LatentGAN, the technique encodes SMILES strings into latent vector representations of size 512. A Wasserstein Generative Adversarial network with Gradient Penalty may be trained to generate latent vectors resembling that of the training set, which are then decoded using a heteroencoder.

Regarding a junction tree variational autoencoder (JT-VAE), the model generates molecular graphs in two phases. The model first generates a tree-structured scaffold over chemical substructures, and then combines them into a molecule with a graph message passing network. This approach enables incrementally expanding molecules while maintaining chemical validity at every step.

Regarding an objective-reinforced generative adversarial network (ORGAN), the model is a sequence-generation model based on adversarial training that aims at generating discrete sequences that emulate a data distribution while using reinforcement learning to bias the generation process towards some desired objective rewards. ORGAN incorporates at least 2 networks: a generator network and a discriminator network. The goal of the generator network is to create candidate drug compounds indistinguishable from the empirical data distribution of real drug compounds. The discriminator exists to learn to distinguish a candidate drug compound from real data samples. Both models are trained in alternation.

To properly train a GAN, the gradient must be back-propagated between the generator and discriminator networks. Reinforcement uses an N-depth Monte Carlo tree search, and the reward is a weighted sum of probabilities from the discriminator and objective reward. Both the generator and discriminator may be pre-trained for 250 and 50 epochs, respectively, and then jointly trained for 100 epochs utilizing an optimizer with a learning rate of 0.0001. The learning rate may refer to a hyperparameter of a neural network, and the learning rate may be a number that determines an amount of change (e.g., weights, hidden layers, etc.) to make to a machine learning model in response to an estimated error. Bayesian optimization may be used to determine the optimal learning rate during training of a particular neural network. In some embodiments, validity and uniqueness of candidate drug compounds may be used as rewards.

The scientist module 153 may also include one or more machine learning models trained to perform causal inference using counterfactuals. The causal inference, as described herein, may be used to determine whether the creator module 151 actually generated a candidate drug candidate, including a desired activity in such candidate, or if it was determined because of noisy data (e.g., scarce or incorrect data).

Figure 1C:
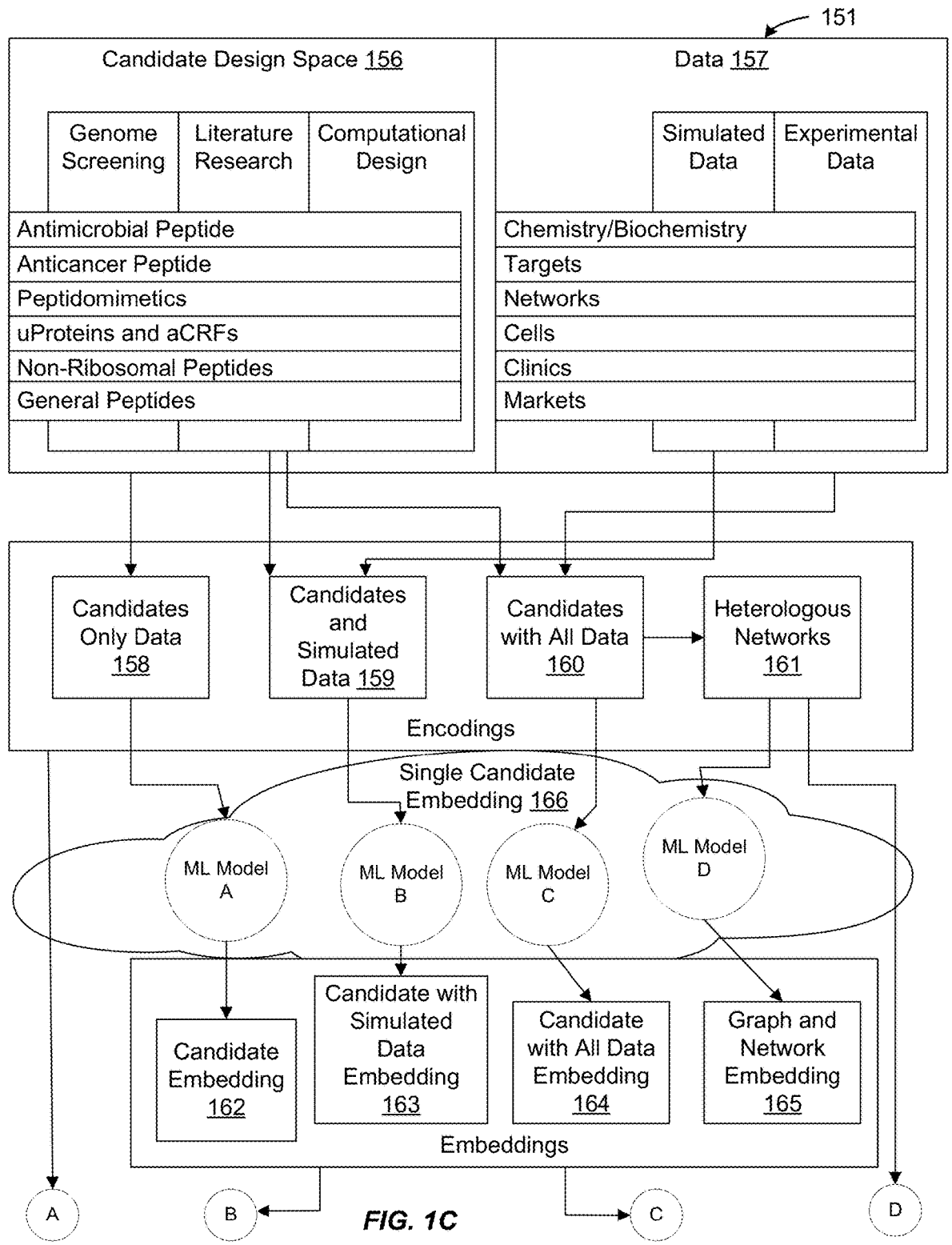
FIG. 1C illustrates first components of an architecture of the creator module according to certain embodiments of this disclosure.

FIG. 1C illustrates first components of an architecture of the creator module 151 according to certain embodiments of this disclosure. A candidate design space 156 and data 157 may be included in the biological context representation 200, such space 156 and data 157 to include the various sequences of the candidate drug compounds or real drug compounds. In some embodiments, the creator module 151 may populate the candidate design space 156. The candidate design space 156 may include a vast amount of information retrieved from numerous sources or generated by the AI engine 140. The candidate design space 156 may include information pertaining to antimicrobial peptides, anticancer peptides, peptidomimetics, uProteins and aCRFs, non-ribosomal peptides, and general peptides that are retrieved via genomic screening, literature research, or computationally designed using the AI engine 140. The candidate design space 156 may be updated each time the creator module 151 generates a new candidate drug compound. The candidate design space 156 may also be updated continuously or continually as new literature is published or genomic screenings are performed.

The creator module 151 may also use data 157 to generate the candidate drug compounds. In some embodiments, the data 157 may be generated or provided by the descriptor module 152. In some embodiments, the data may be received from any suitable source. The data may include molecular information pertaining to chemistry/biochemistry, targets, networks, cells, clinical trials, market (e.g., analysis, results, etc.) that result from performing simulations or experiments.

The creator module 151 may encode the candidate design space 156 and the data 157 into various encodings. In some embodiments, an attention message-passing neural network may be used to encode molecular graphs. An initial set of states may be constructed, one for each node in a molecular graph. Then, each node may be allowed to exchange information, to "message" with its neighboring nodes. Each message may be a vector describing an atom of a molecule from the atom's perspective in the molecule. After one such step, each node state will contain an awareness of its immediate neighborhood. Repeating the step makes each node aware of its second-order neighborhood, and so forth. During the message-passing stage and based on the total number of occurrences of a message, an attention layer may be used to identify interesting features of a molecule. A certain weight (e.g., heavy, light) may be assigned to a message that occurs more or fewer than a threshold number of times, thereby causing that message to stand out more when the messages are aggregated. For example, a message that occurs a very small number of times (e.g., less than a threshold) may be more likely to include a desirable feature as opposed to a message that occurs a large number of times. In another example, a message that occurs more than a threshold number of times may be weighted more heavily than a message that occurs fewer than the threshold number of times. Any suitable weighting may be configured to cause a message to stand out more.

Using a summation function to reduce the size of the messages and increase computational efficiency, the attention mechanism may aggregate the messages with their weights. In such a way, the techniques may be able to scale to remain computationally efficient as the number of messages increases. Such a technique may be beneficial because it reduces resource (e.g., processing, memory) consumption when performing computations with a large design space, including information in that design space pertaining to structure, semantic, sequence, physiochemical properties, etc.

After a chosen number of "messaging rounds", all the context-aware node states are collected and converted to a summary representing the whole graph. All the transformations in the steps above may be carried out with machine learning models (e.g., neural networks), yielding a machine learning model that can be trained with known techniques to optimize the summary representation for the current task. The following relationships may be used by the attention message-passing neural network:

1. Message Passing $$m_v^{(t)} = A_t(h_v^{(t)}, S_v^{(t)}), \text{ where}$$

$$S_v^{(t)} = \{(h_w^{(t)}, e_{vw}) | w \in N(v)\}$$

$$A_t(h_v^{(t)}, \{(h_w^{(t)}, e_{vw})\}) = \sum_{w \in N(v)} f_{NN}^{(e_{vw})}(h_w^{(t)}) \odot \frac{\exp(g_{NN}^{(e_{vw})}(h_w^{(t)}))}{\sum_{w' \in N(v)} \exp(g_{NN}^{(e_{vw'})}(h_{w'}^{(t)}))}$$

2. Node Update $$h_v^{(t+1)} = u_t(h_v^{(t)}, m_v^{(t)})$$

3. Readout $$\hat{y} = R\{(h_v^{(K)} | v \in G)\}$$

$m^{(t)}_v$ is the message function, At is the attention function, $U_t$ is the node update function, N(v) is the set of neighbors of node v in graph G, $h^{(t)}_v$ is the hidden state of node v at time t, and $m^{(t)}_v$ is a corresponding message vector. For each atom v, messages will be passed from its neighbors and aggregated as the message vector $m^{(t)}$ from its surrounding environment. Then the hidden state $h^{(t)}_v$ is updated by the message vector.

ŷ is a resulting fixed-length feature vector generated for the graph, and R is a readout function invariant to node ordering, a feature allowing the MPNN framework to be invariant to graph isomorphism. The graph feature vector ŷ then is passed to a fully connected layer to give prediction. All functions $M_t$, $U_t$, and R are neural networks and their weights are learned during training.

As depicted, a "Candidates Only Data" encoding 158 may encode just the information from the candidate design space, a "Candidates and Simulated Data" encoding 159 may encode information from the candidate design space 156 and the simulated data from the data 157, and a "Candidates with All Data" encoding 160 may encode information from the candidate design space 156 and both the simulated and experimental data from the data 157. Further, a "Heterologous Networks" encoding 161 may be generated using the "Candidates with All Data" encoding 160. The encodings 158, 159, 160, and 161 may include information pertaining to molecular structure, physiochemical properties, semantics, and so forth.

Each of the encodings 158, 159, 160, and 161 may be input into a separate machine learning model trained to generate an embedding. ML Model A, ML Model B, ML Model C, and ML Model D may be included in a "Single Candidate Embedding" Layer.

"Candidates Only Data" encoding 158 may be input into ML Model A, which outputs a "Candidate Embedding" 162. "Candidates and Simulated Data" encoding 159 may be input into ML Model B, which outputs a "Candidate and Simulated Data Embedding" 163. "Candidates with All Data" encoding 160 may be input into ML Model C, which outputs "Candidate with All Data Embedding" 164. "Heterologous Networks" encoding 161 may be input into ML Model D, which outputs "Graph and Network Embedding" 165. The embeddings 162, 163, 164, and 165 may represent information pertaining to a single candidate drug compound.

Figure 1D:
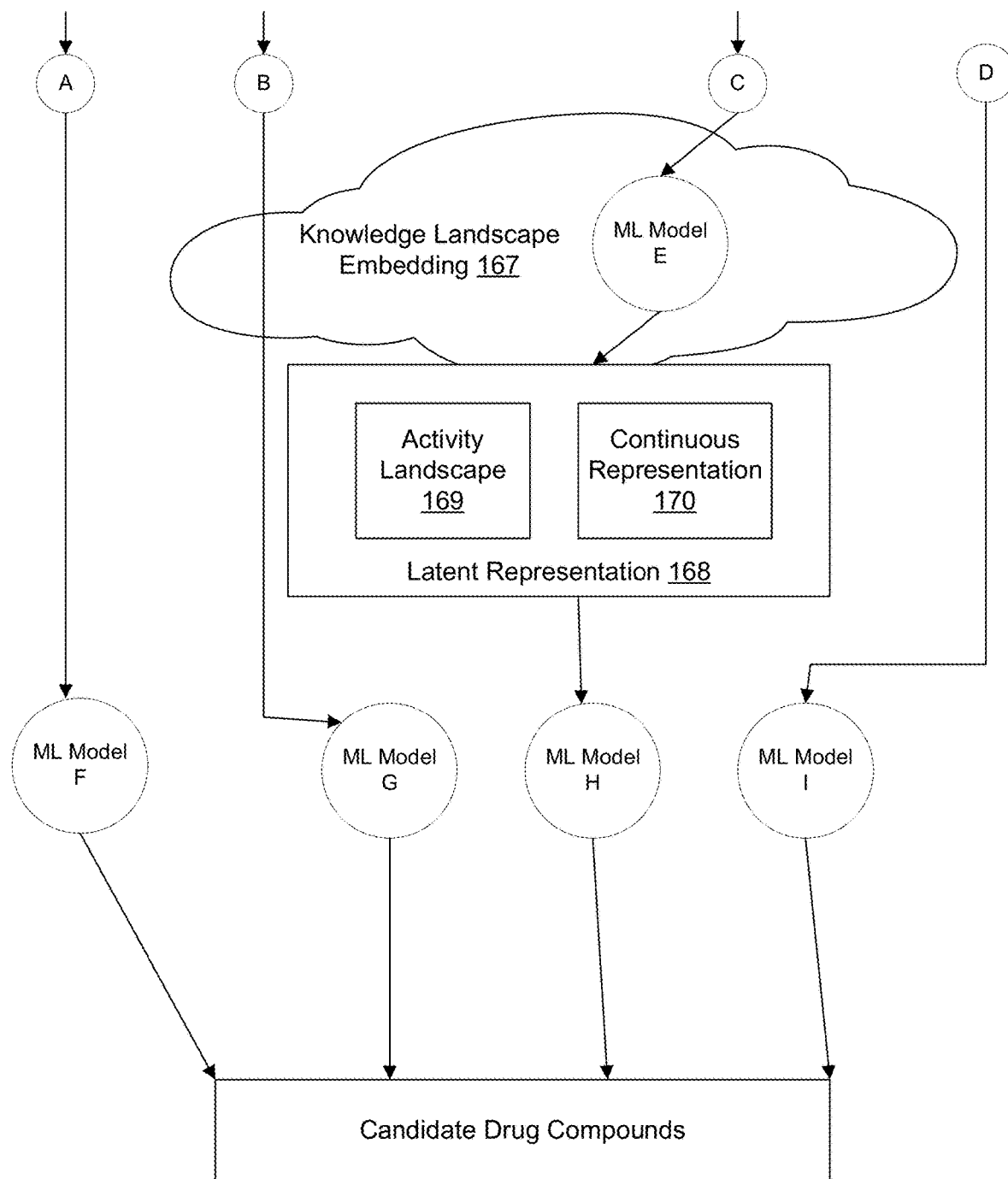
FIG. 1D illustrates second components of the architecture of the creator module according to certain embodiments of this disclosure.

FIG. 1D illustrates second components of the architecture of the creator module 151 according to certain embodiments of this disclosure. As depicted, the encodings 158, 159, 160, and 161 are input into ML Model F, which is trained to output a candidate drug compound based on the encodings 158, 159, 160, and 161.

The embeddings 162, 163, 164, and 165 are input into ML Model G, which is trained to output a candidate drug compound based on the embeddings 162, 163, 164, and 165. In some embodiments, the "Heterologous Networks" 161 may be input into ML Model I, which is trained to output a candidate drug compound based on the "Heterologous Networks" 161. The embeddings 162, 163, 164, and 165 are also input into ML Model E in a "Knowledge Landscape Embedding" layer 167. The ML Model E is trained to output a "Latent Representation" based on the embeddings 162, 163, 164, and 165.

The "Latent Representation" 168 may include an "Activity Landscape" 169 and a "Continuous Representation" 170. The "Continuous Representation" 170 may include information (e.g., structural, semantic, etc.) pertaining to all of the molecules (e.g., real drug compounds and candidate drug compounds), and the "Activity Landscape" 169 may include activity information for all of the molecules. In some embodiments, the ML Model E may be a variational autoencoder that receives the embeddings 162, 163, 164, and 165 and outputs lower-dimensional embeddings that are machine-readable and less computationally expensive for processing. The lower-dimensional embeddings may be used to generate the "Latent Representation" 168. An architecture of the variational autoencoder is described further below with reference to FIG. 1E.

Figure 8A:
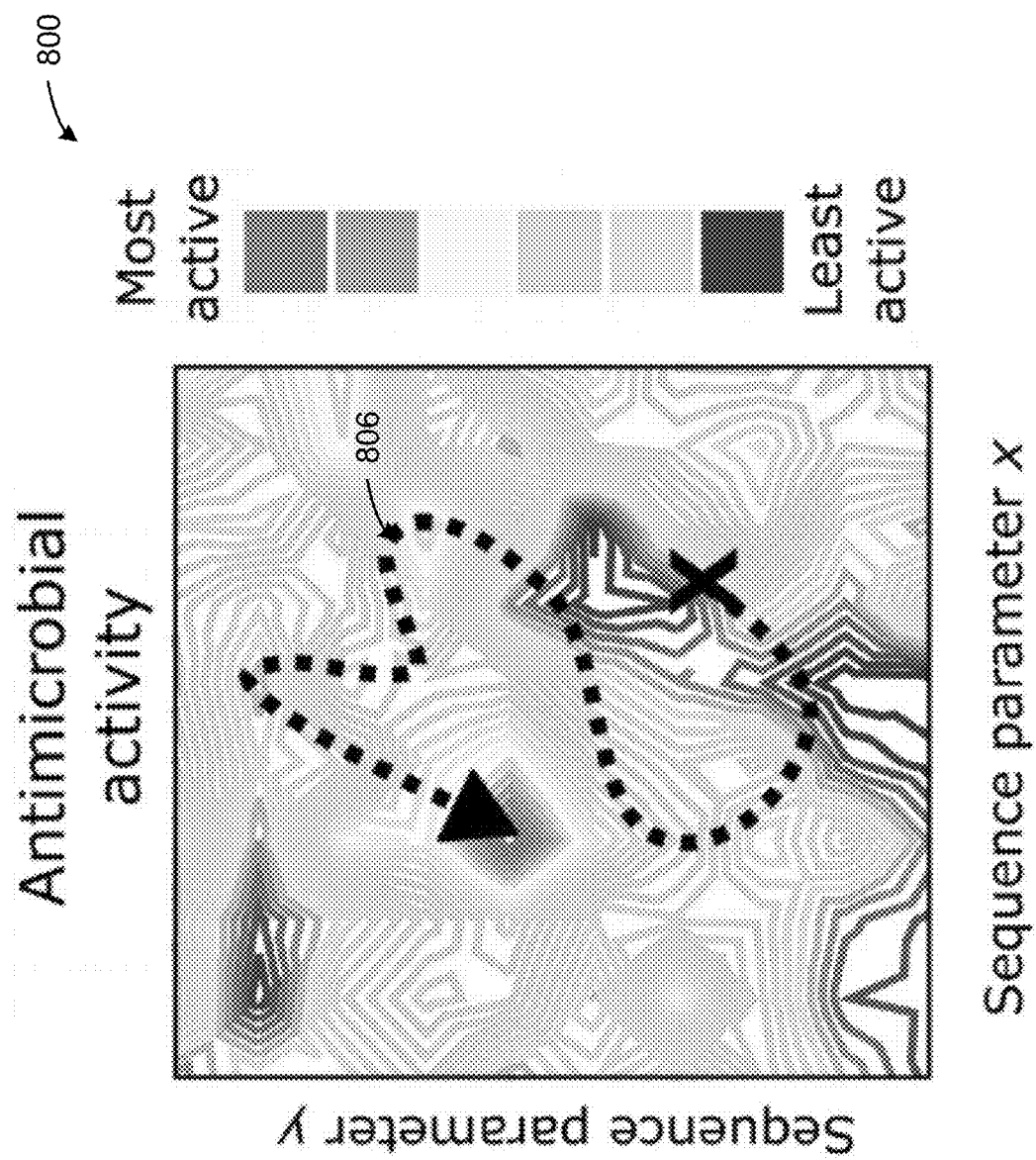

The "Latent Representation" 168 is input into the ML Model H. ML Model H may be any suitable type of machine learning model described herein. ML Model H may be trained to analyze the "Latent Representation" 168 and generate a candidate drug compound. The "Latent Representation" 168 may include multiple dimensions (e.g., tens, hundreds, thousands) and may have a particular shape. The shape may be rectangular, cube, cuboid, spherical, an amorphous blob, conical, or any suitable shape having any number of dimensions. The ML Model H may be a generative adversarial network, as described herein. The ML Model H may determine a shape of the "Latent Representation" 168 and may determine an area of the shape from which to obtain a slice based on "interesting" aspects of that area. An interesting aspect may be a peak, valley, a flat portion, or any combination thereof. The ML Model H may use an attention mechanism to determine what is "interesting" and what is not. The interesting aspect may be indicative of a desirable feature, such as a desirable activity for a particular disease or medical condition. The slice may include a combination of a portion of any of the information included in the "Latent Representation" 168, such as the structural information, physiochemical properties, semantic information, and so forth. The information included in the slice may be represented as an eigenvector that includes any number of dimensions from the "Latent Representation" 168. The term "slice" and "candidate drug compound" may be used interchangeably. The slice may be visually presented on a display screen, as shown in FIG. 8A.

A decoder may be used to transform the slice from the lower-dimensional vector to a higher-dimensional vector, which may be analyzed to determine what information is included in that slice. For example, the decoder may obtain a set of coordinates from the higher-dimensional vector which may be back-calculated to determine what information (e.g., structural, physiochemical, semantic, etc.) they represent.

Each of the candidate drug compounds generated by the ML Model F, ML Model G, ML Model H, and ML Model I may be ranked and one of the candidate drug compounds may be classified as a selected candidate drug compound, as described herein. Further, the candidate drug compounds may be input into one or more machine learning models trained to perform benchmark analysis, as described herein. Based on the benchmark analysis, any of the machine learning models in the creator module 151 may be optimized (e.g., tuning weights, adding or removing hidden layers, changing an activation function, etc.) to modify a parameter (e.g., uniqueness, validity, novelty, etc.) score for the machine learning models when generating subsequent candidate drug compounds.

Figure 1E:
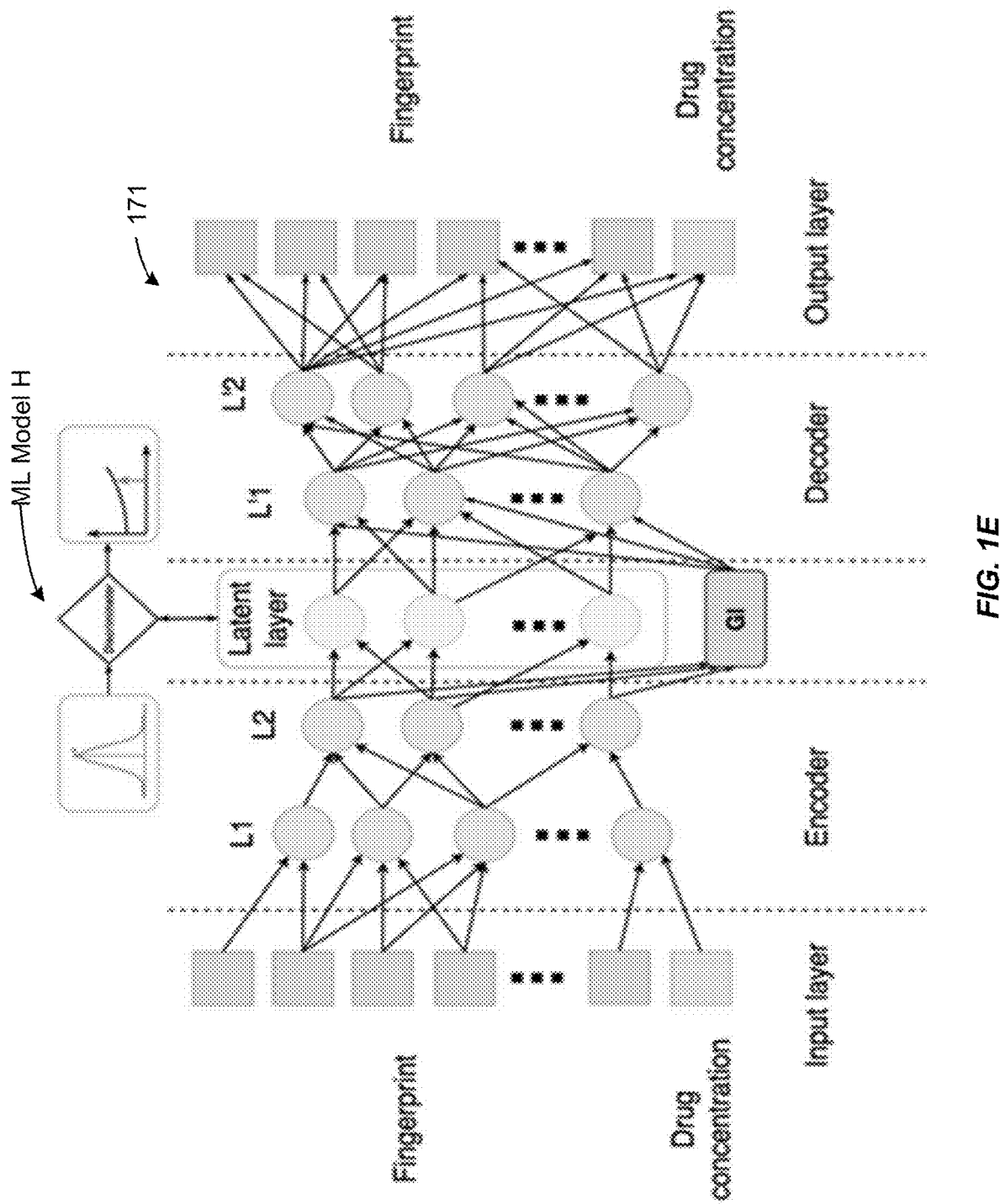
FIG. 1E illustrates an architecture of a variational autoencoder according to certain embodiments of this disclosure.

FIG. 1E illustrates an architecture of a variational autoencoder machine learning model according to certain embodiments of this disclosure. In some embodiments, the variational autoencoder may include an input layer, an encoder layer, a latent layer, a decoder layer, and an output layer. The input layer may receive fingerprints of drug compounds or candidate drug compounds represented as higher-dimensional vectors, as well as associated drug concentration(s). The encoder layer may include one or more hidden layers, activation functions, and the like. The encoder layer may receive the fingerprint and drug concentration from the input layer and may perform operations to translate the higher-dimensional vectors into lower-dimensional vectors, as described herein. The latent layer may receive the lower-dimensional vectors and represent them in the "Latent Representation" 168. The latent layer may input the "Latent Representation" 168 into the ML Model H, which is a generative adversarial network including a generator and a discriminator, as described herein. The architecture of the generator and the discriminator is discussed further below with reference to FIG. 1F. The generator generates candidate drug compounds and the discriminator analyzes the candidate drug compounds to determine whether they are valid or not. The GI may generate the candidate drug compounds.

The candidate drug compounds output by the latent layer may be input into the decoder layer where the lower-dimensional vectors are translated back into the higher-dimensional vectors. The decoder layer may include one or more hidden layers, activation functions, and the like. The decoder layer may output the fingerprints and the drug concentration. The output fingerprint and drug concentration may be analyzed to determine how closely they match the input fingerprint and drug concentration. If the output and input substantially match, the variational autoencoder may be properly trained. If the output and the input do not substantially match, one or more layers of the variational autoencoder may be tuned (e.g., modify weights, add or remove hidden layers).

Figure 1F:
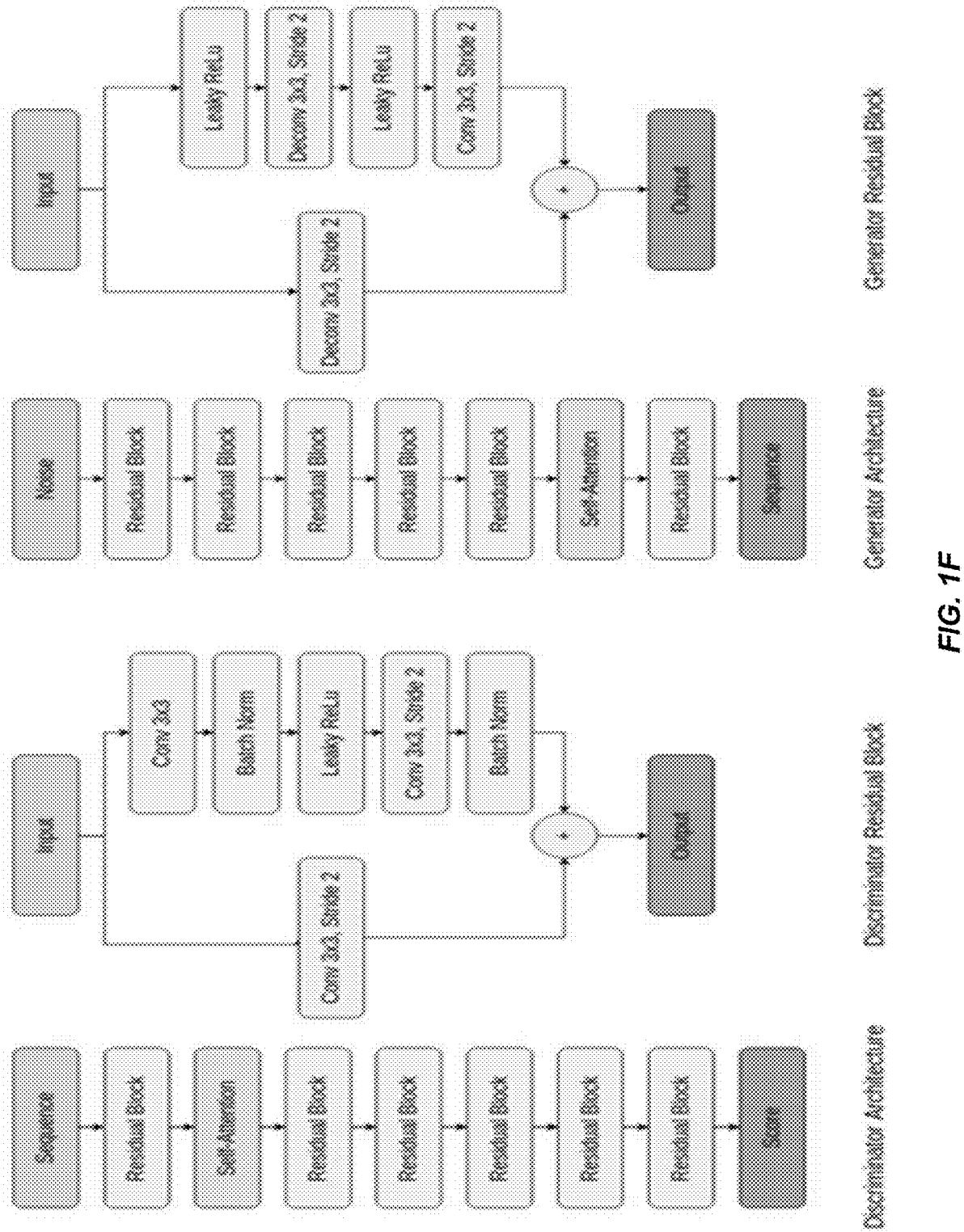
FIG. 1F illustrates an architecture of a generative adversarial network used to generate candidate drugs according to certain embodiments of this disclosure.

FIG. 1F illustrates an architecture of a generative adversarial network used to generate candidate drugs according to certain embodiments of this disclosure. As depicted, there is an architecture for the discriminator, discriminator residual block, generator, and generator residual block.

The discriminator architecture may receive a sequence (e.g., candidate drug compound) as an input. The discriminator architecture may include an arrangement of blocks in a particular order that improves computational efficiency when processing the sequence to determine whether the sequence is valid or not. For example, the particular order of blocks includes a first residual block, a self-attention block, a second residual block, a third residual block, a fourth residual block, a fifth residual block, and a sixth residual block. The discriminator may output a score (e.g., 0 or 1) for whether the received sequence is valid or not.

The discriminator residual block architecture may receive an input filtered into two processing pathways. A first processing pathway performs a conversion operation on the input. The second processing pathway performs several operations, including a conversion, a batch normalization operation, a leaky rectified linear (e.g., ReLu) operation, a conversion operation, and another batch normalization operation. The leaky ReLu operation may perform a threshold operation, where any input value less than zero is multiplied by a fixed scalar, for example. The output from the first and second processing pathways is summed and then output.

The generator architecture may receive a noise (e.g., biological context representation 200) as an input. The generator architecture may include an arrangement of blocks in a particular order that improves computational efficiency when processing the noise to generate a sequence (e.g., candidate drug compound). For example, the particular order of blocks includes a first residual block, a second residual block, a third residual block, a fourth residual block, a fifth residual block, a self-attention block, and a sixth residual block. The generator may output a score (e.g., 0 or 1) for whether the received sequence is valid or not.

The generator residual block architecture may receive an input filtered into two processing pathways. A first processing pathway performs a de-conversion operation on the input. The second processing pathway performs several operations, including a conversion, a batch normalization operation, a leaky ReLu operation, a de-conversion operation, and another batch normalization operation. The output from the first and second processing pathways is summed and then output.

FIG. 1G illustrates types of encodings to represent certain types of drug information according to certain embodiments of this disclosure. A table 180 includes three columns labeled "Encoding", "Compressed?", and "Information". The "Encoding" column includes rows storing a type of encoding used to represent a certain type of information; the "Compressed?" column includes rows storing an indication of whether the encoding in that row is compressed; and the "Information" column includes rows storing a type of information represented by the encoding in each respective row. The descriptor module 152 may include a machine learning module trained to analyze a candidate drug compound and identify various structural properties, physiochemical properties, and the like. The descriptor module 152 may be trained to represent the type of structural and physiochemical properties using an encoding that increases computational efficiency and to store a description including the encodings at a node representing the candidate drug compound. During processing, the encodings may be aggregated for each candidate drug compound.

For example, using an alphanumeric string, SMILES encoding spells out molecular structure from a beginning portion to an ending portion. Morgan Fingerprints may be useful for temporal molecular structures and the descriptor module 152 may include a machine learning module trained to output a compressed vector. Morgan Fingerprints may include the isomer for a particular molecule, and common backbone structures for molecules.

As depicted, SMILES, Morgan Fingerprints, InChI, One-Hot, N-gram, Graph-based Graphic Processing Unit Nearest Neighbor Search (GGNN), Gene regulatory network (GRN), M-P Neural Network (MPNN), and Knowledge Graph (Structural/Semantic) encodings represent structural information of molecules (drug compounds). The Morgan Fingerprints, GGNN, GRN, and 1MPNN are also compressed to improve computations, while the SMILES, InChI, One-Hot, N-gram, and the Knowledge Graph are not compressed.

Quantitative structure-activity relationship (QSAR), Z-descriptors, and the Knowledge Graph encodings may represent physiochemical properties of molecules. These encodings may not be compressed. The QSAR encoding may include the type of activity (e.g., and without limitation to a particular physiological or anatomical organ, organ, state or states, or to a particular disease-process, antiviral, antimicrobial, antifungal, antiemetic, antineoplastic, anti-inflammatory, leukotriene inhibitory, neurotransmitter inhibitory, etc.) the molecule provides. The encodings selected for each type of information may optimize the computations when considering such a large design space with information pertaining to structure, physiochemical properties, and semantic information. The large design space referred to may include not only a string of amino acid sequences, and physiochemical properties, but also the semantic information, such as system biology and ontological information, including relationships between nodes, molecular pathways, molecular interactions, molecular family, and the like.

Figure 1H:
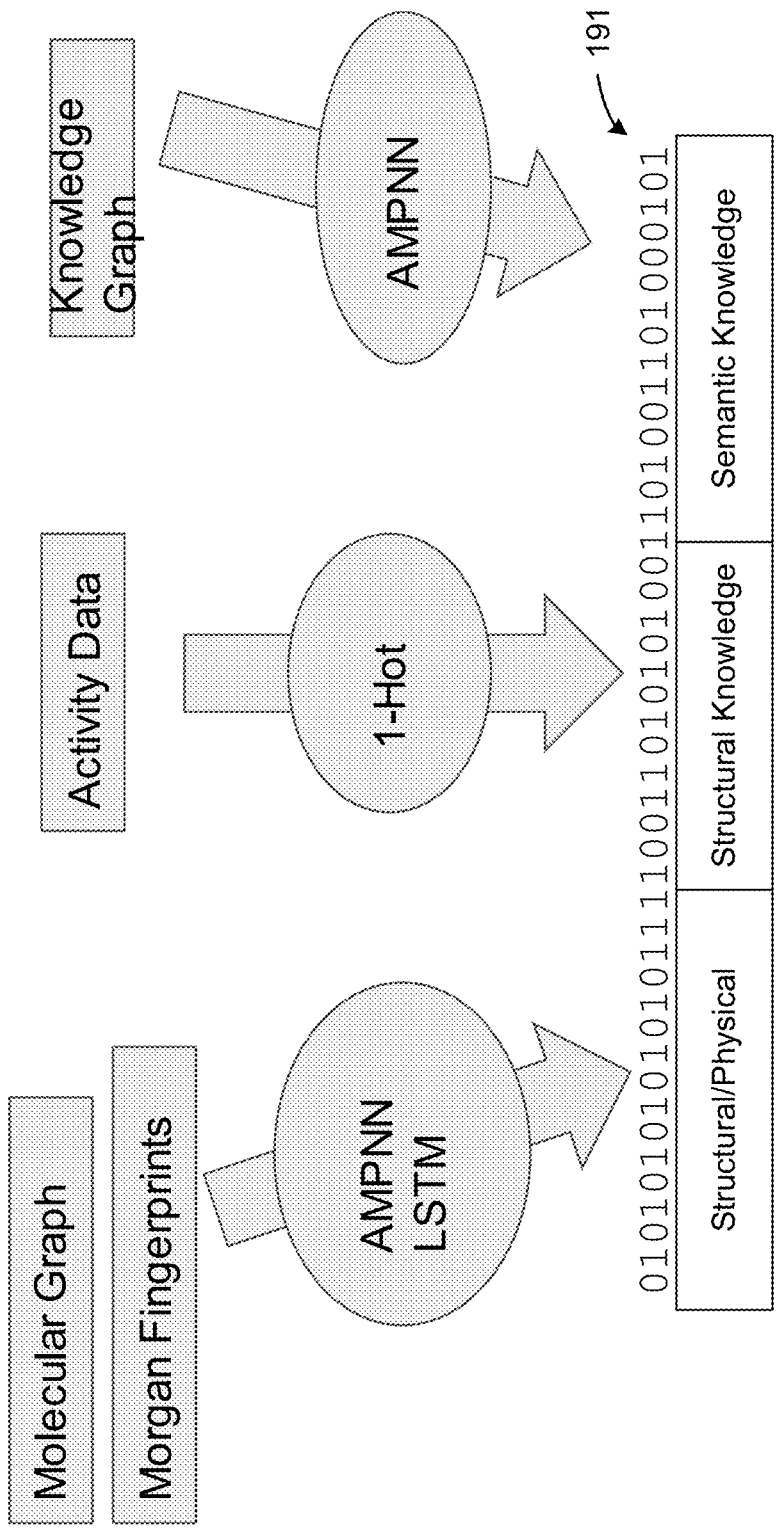
FIG. 1H illustrates an example of concatenating numerous encodings into a candidate drug according to certain embodiments of this disclosure.

FIG. 1H illustrates an example of concatenating (merging) numerous encodings into a candidate drug compound according to certain embodiments of this disclosure. A concatenated vector 191 may represent an embedding for a candidate drug compound. In some embodiments, an ensemble learning approach may be implemented by using different types of techniques to generate unique encodings and merge those unique encodings to improve generated candidate drug compounds. As depicted, various encoding techniques may be used to represent different types of information. The different types of information (e.g., structural, semantic, etc.) may be represented by unique encodings. For example, molecular graphs and Morgan Fingerprints may represent structural and physical molecular information. Activity data (e.g., QSAR) may represent molecular structural knowledge or molecular physiochemical knowledge, and a knowledge graph may represent molecular semantic knowledge. An attention message passing neural network (AMPNN) or long short-term memory (LSTM) may receive the molecular graph and Morgan Fingerprints as input and output the structural/physical information represented by 1s and 0s. One-hot may receive the activity data as input and output the structural knowledge represented by 1s and 0s. AMPNN may receive a knowledge graph as input and output semantic knowledge represented by 1s and 0s. The resulting concatenated vector 191 is a combination of each type of information for a single candidate drug compound. Accordingly, the single candidate drug compound may include better properties and more robust information than conventional techniques.

Figure 1I:
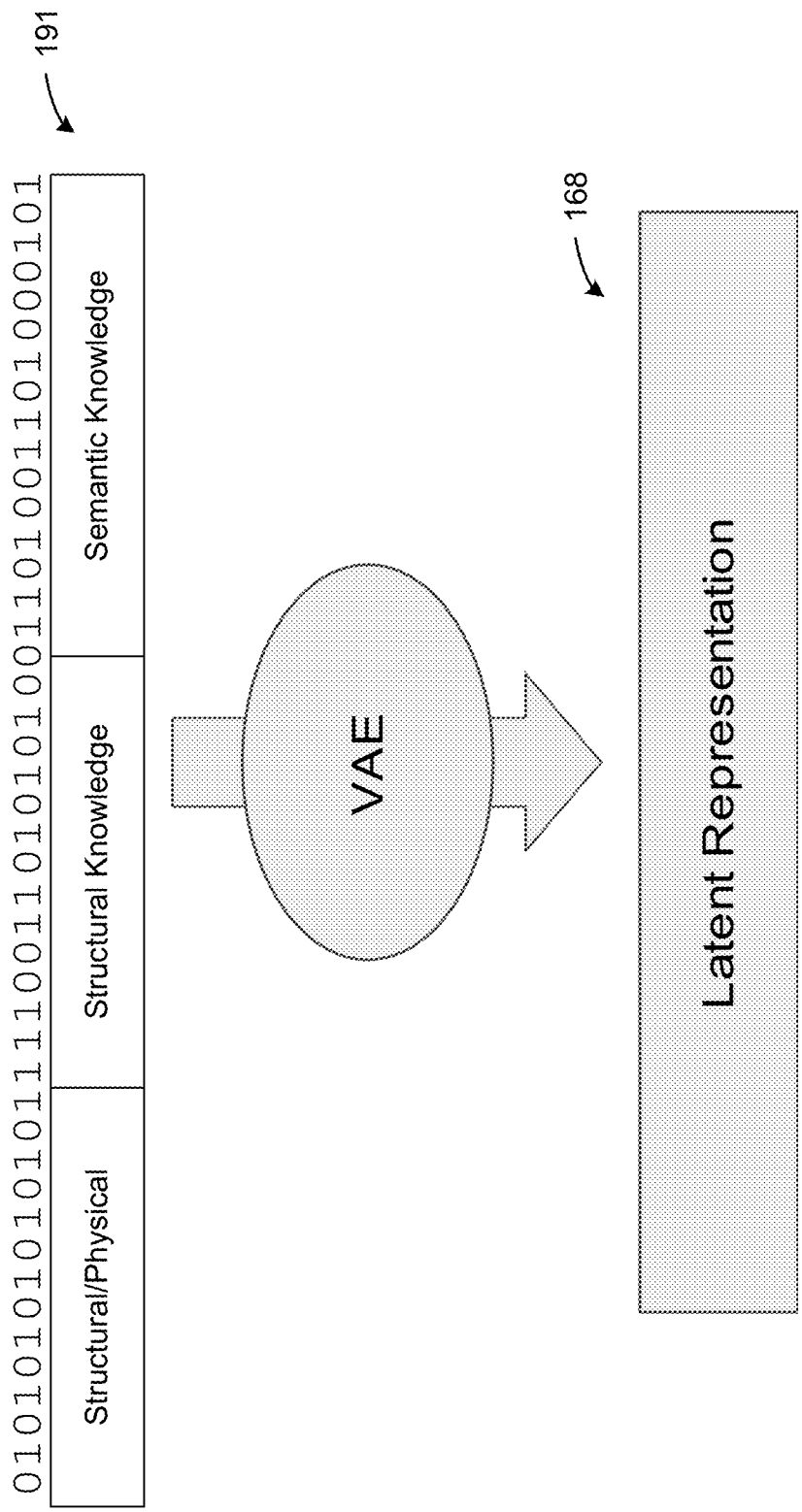
FIG. 1I illustrates an example of using a variational autoencoder to generate a latent representation of a candidate drug according to certain embodiments of this disclosure.

FIG. 1I illustrates an example of using a variational autoencoder (VAE) to generate a Latent Representation 168 of a candidate drug compound according to certain embodiments of this disclosure. The concatenated vector 191 (e.g., embedding) may be higher-dimensional prior to being input to the VAE. The VAE may be trained to translate the higher-dimensional concatenated vector 191 to a lower-dimensional concatenated vector that represents the Latent Representation 168.

Figure 2:
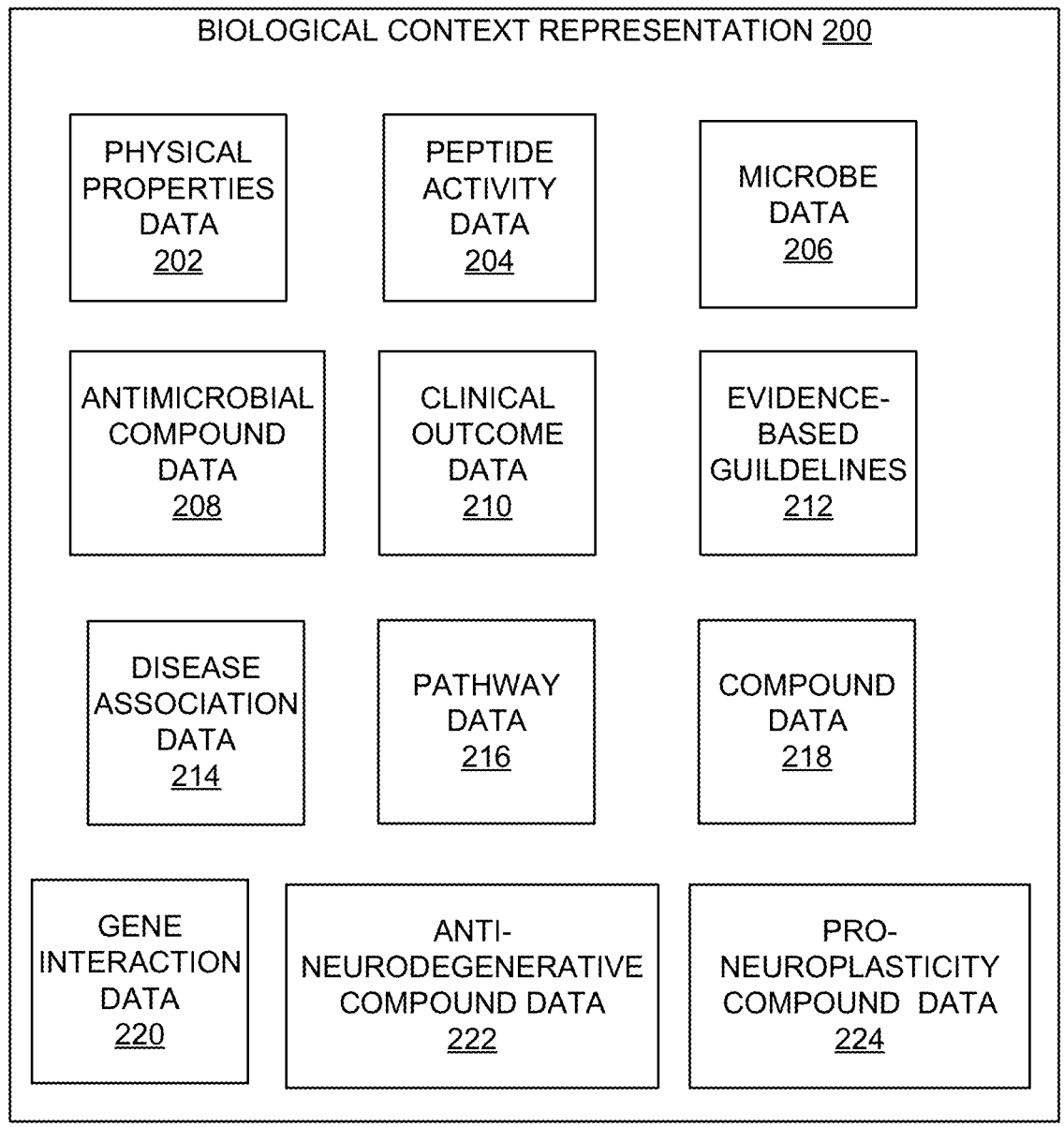
FIG. 2 illustrates a data structure storing a biological context representation according to certain embodiments of this disclosure.

FIG. 2 illustrates a data structure storing a biological context representation 200 according to certain embodiments of this disclosure. Biology is context-dependent and dynamic. For example, the same molecule can manifest multiple, potentially competing, phenotypes. Further, data on an existing drug labeled as antimicrobial can suggest a null behavior in applications against different microbes or even against the same microbes but in different contexts, e.g., temperature, pressure, environmental, contextual, comorbid. To accurately predict candidate drug compounds that provide desirable activity levels in design spaces, the machine learning models 132 are trained to handle evolving knowledge maps of biology and drug compounds. Further, conventional techniques for discovery and generating drug compounds may be ineffective for biological data because such data is non-Euclidian.

In some embodiments, the biological context representation 200 generated by the disclosed techniques may be used to graphically model the continually or continuously modifying biological and drug compound knowledge. That is, the biology may be represented as graphs within a comprehensive knowledge graph (e.g., biological context representation 200), where the graphs have complex relationships and interdependencies between nodes.

The biological context representation 200 may be stored in a first data structure having a first format. The first format may be a graph, an array, a linked list, or any suitable data format capable of storing the biological context representation. In particular, FIG. 2 illustrates various types of data received from various sources, including physical properties data 202, peptide activity data 204, microbe data 206, antimicrobial compound data 208, clinical outcome data 210, evidence-based guidelines 212, disease association data 214, pathway data 216, compound data 218, gene interaction data 220, anti-neurodegenerative compound data 222, or pro-neuroplasticity compound data 224.

These example data may be curated by the AI engine 140 or a person having a certain degree (e.g., a degree in data science, molecular biology, microbiology, etc.), certification, license (e.g., a licensed medical doctor (e.g., M.D. or D.O.), or credential. Further, the data in the biological context representation 200 may be retrieved from any suitable data source (e.g., digital libraries, websites, databases, files, or the like). These examples are not meant to be limiting. Thus, the example types of data are also not meant to be limiting and other types of data may be stored within the biological context representation without departing from the scope of this disclosure. Further, the various data included in the biological context representation 200 may be linked based on one or more relationships between or among the data, in order to represent knowledge pertaining to the biological context or drug compound.

The physical properties data 202 includes physical properties exhibited by the drug compound. The physical properties may refer to characteristics that provide a physical description of the drug such as color, particle size, crystalline structure, melting point, and solubility. In some instances, the physical properties data 202 may also include chemical property data, such as the structure, form, and reactivity of a substance. In some embodiments, biological data may also be included (e.g., anti-neurodegenerative compound data, pro-neuroplasticity compound data, anti-cancer data) in the biological context representation 200.

The peptide activity data 204 may include various types of activity exhibited by the drug. For example, the activity may be hormonal, antimicrobial, immunomodulatory, cytotoxic, neurological, and the like. A peptide may refer to a short chain of amino acids linked by peptide bonds.

The microbe data 206 may include information pertaining to cellular structure (e.g., unicellular, multicellular, etc.) of a microscopic organism. The microbes may refer to bacteria, parasites, fungi, viruses, prions, or any combination of these, etc.

The antimicrobial compound data 208 may include information pertaining to agents that kill microbes or stop their growth. This data may include classifications based on the microorganisms against which the antimicrobial compound acts (e.g., antibiotics act against bacteria but not against viruses; antivirals act against viruses but not against bacteria). The antimicrobial compound may also be classified according to function (e.g., microbicidal, meaning "that which kills, vitiates, inactivates or otherwise impairs the activity of certain microbes").

The clinical outcome data 210 may include information pertaining to the administration of a drug compound to a subject in a clinical setting. For example, upon or subsequent to administration of the drug compound, the outcome may be a prevented disease, cured disease, treated symptom, etc.

The evidence-based guidelines 212 may include information pertaining to guidelines based upon clinical studies for acceptable treatment or therapeutics for certain diseases or medical conditions. Evidence-based guidelines data 212 may include data specific to various specialties within healthcare such as, for example, obstetrics, anesthesiology, hepatology, gastroenterology, neurology, pulmonology, orthopedics, pediatrics, trauma care (including but not limited to burns and post-burn infections), histology, oncology, ophthalmology, endocrinology, rheumatology, internal medicine, surgery (including reconstructive (plastic) and cosmetic), vascular medicine, emergency medicine, radiology, psychiatry, cardiology, urology, gynecology, genetics, and dermatology. In the example described herein, the evidence-based guidelines 212 include systematically developed statements to assist practitioner and patient decisions about appropriate health care (e.g., types of drugs to prescribe for treatment) for specific clinical circumstances.

The disease association data 214 may include information about which disease or medical condition the drug compounds are associated with. For example, the drug compound Metformin may be associated with the disease type 2 diabetes.

The pathway data 216 may include information pertaining in a design space to the relationships or paths between ingredients (e.g., chemicals) and activity levels.

The compound data 218 may include information pertaining to the compound such as the sequence of ingredients (e.g., type, amount, etc.) in the compound. In the therapeutics industry, for example, the compound data 218 can include data specific to the various types of drug compounds that are designed, defined, developed, or distributed.

The gene interaction data 220 may include information pertaining to which gene the drug compound or a disease may interact with.

The anti-neurodegenerative compound data 222 may include information pertaining to characteristics of anti-neurodegenerative compounds, such as their physical and chemical properties and activities on portions of tissue. For example, the activity may include anti-inflammatory or neuro-protective actions.

The pro-neuroplasticity compound data 224 may include information pertaining to characteristics of pro-neuroplasticity compound, such as their physical and chemical properties and activities on portions of tissue. For example, the activity may enhance the capacity of motor systems by upregulation of neurotrophins.

Figure 3A:
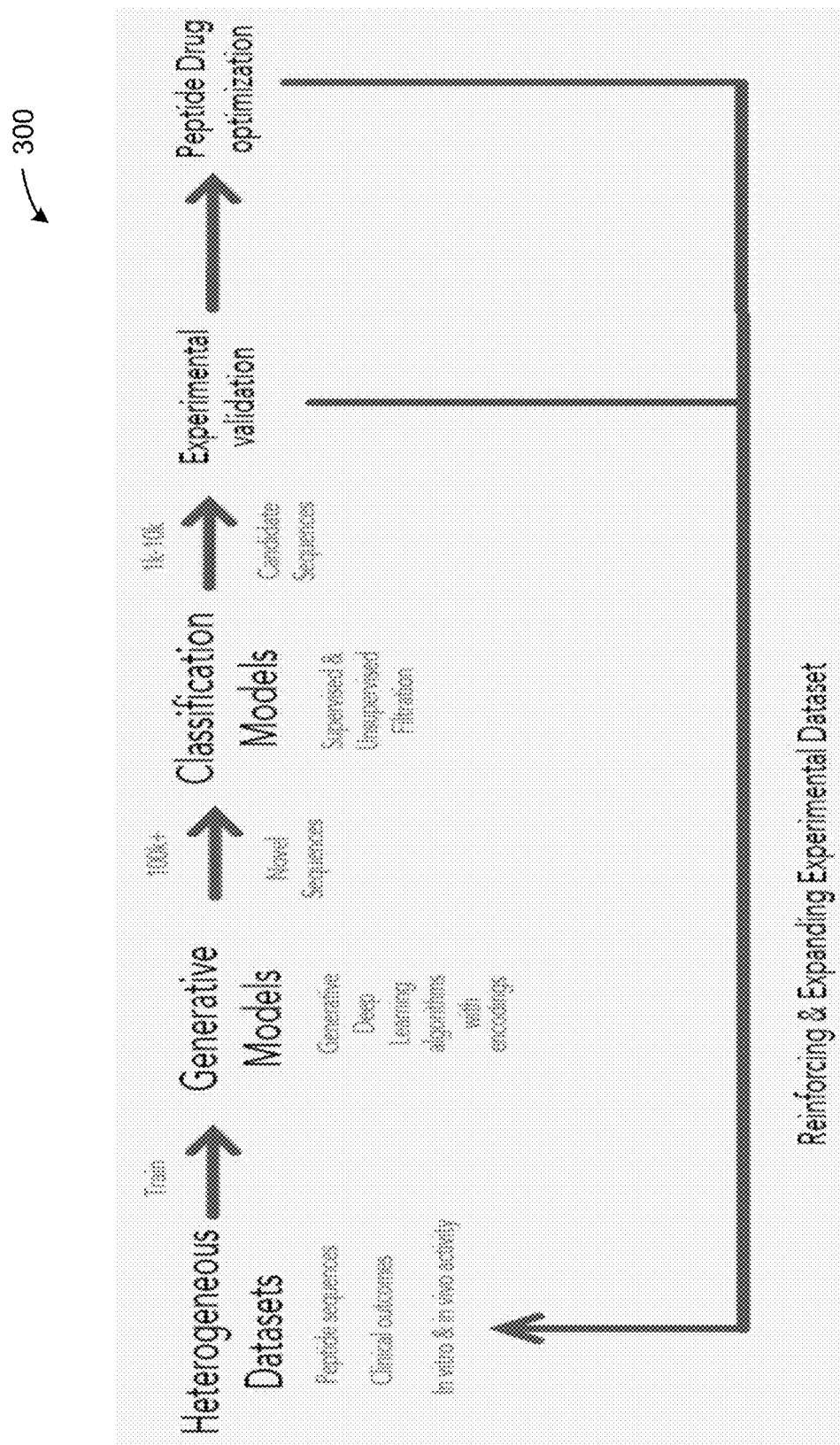
FIGS. 3A-3B illustrate a high-level flow diagram according to certain embodiments of this disclosure.
Figure 3B:
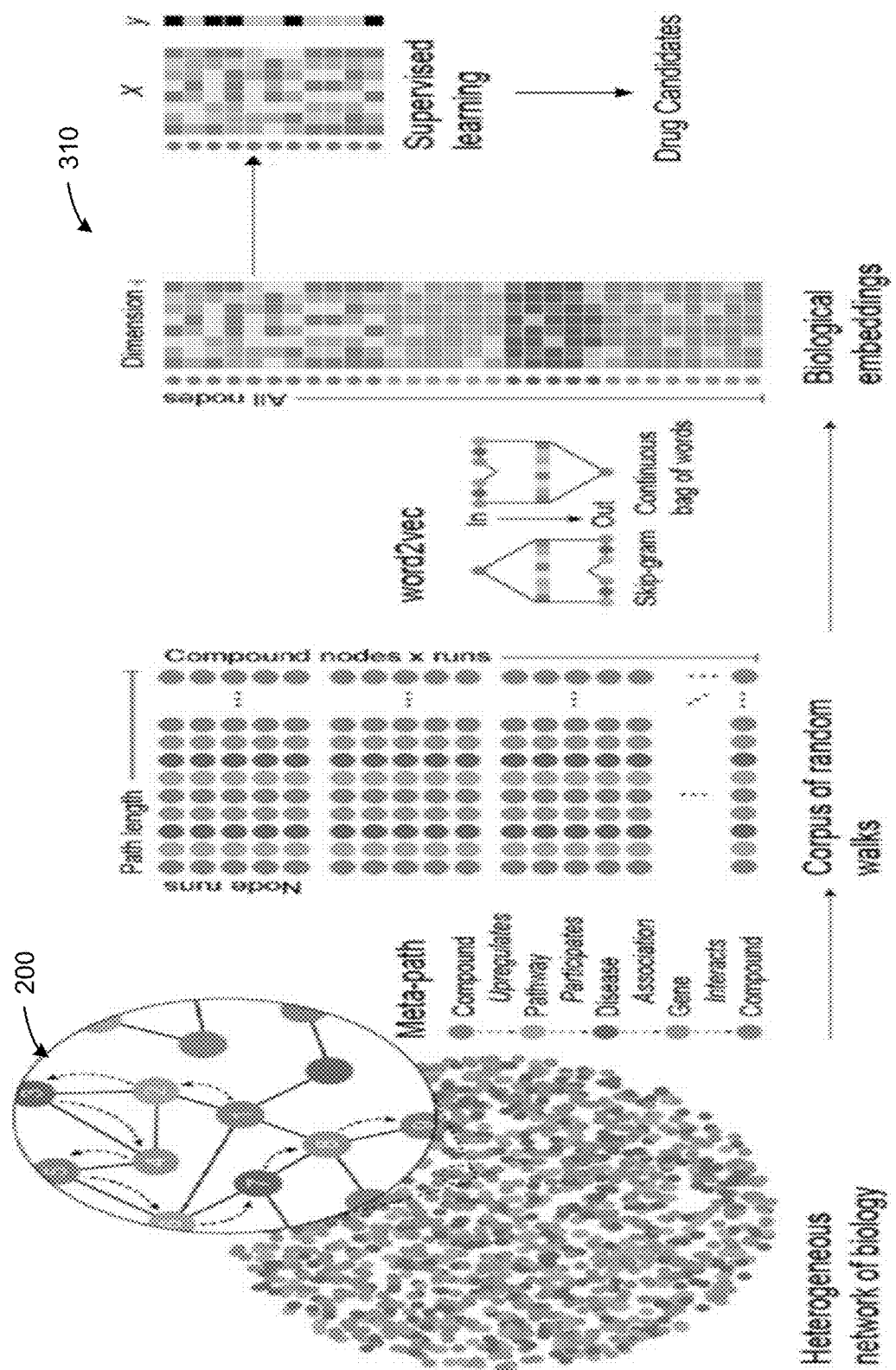

FIGS. 3A-3B illustrate a high-level flow diagram according to certain embodiments of this disclosure. Regarding FIG. 3A, a flow diagram 300 begins with obtaining heterogeneous datasets, such as the biological context representation 200. Heterogeneous datasets may refer to populations or samples of data that are different (e.g., as opposed to homogenous datasets where the data is the same). The heterogeneous datasets may include compound data (e.g., peptide sequence data), clinical outcome data, or activity data (in vitro and in vivo activity), as well as any other suitable data depicted in FIG. 2.

The data structure storing the heterogeneous datasets may be translated to a second data structure having a second format (e.g., a 2-dimensional vector) that the AI engine 140 may use to generate the candidate drug compounds. The next step in the flow diagram 300 includes training the one or more machine learning models 132 using the heterogeneous datasets. The one or more machine learning models 132 (e.g., generative models) may generate a set of candidate drug compounds based on the heterogeneous datasets. As described herein, a machine learning model may use causal inference and counterfactuals when generating the set of candidate drug compounds. Further, a GAN may be used in conjunction with causal inference to generate the set of candidate drug compounds. In some embodiments, a certain number (e.g., over 100,000 candidate drug compounds) of novel candidate drug compounds may be generated in a set. That is, each candidate drug compound in the set of candidate drug compounds is intended to be unique.

The next step in the flow diagram 300 includes inputting the set of candidate drug compounds into one or more machine learning models 132 trained to classify the set of candidate drug compounds. The machine learning models 132 may perform supervised or unsupervised filtering. In some embodiments, the machine learning models 132 may perform clustering to rank the various candidate drug compounds to classify one candidate drug compound as a selected candidate drug compound. In some embodiments, the machine learning models 132 may output a subset (e.g., 1,000 to 10,000, or more, or fewer) of candidate drug compounds.

The next step in the flow diagram 300 may include performing experimental validation by validating whether each candidate drug compound in the subset of candidate drug compounds provides the desired level of certain types of activity in a design space. The results of the experimental validation may be fed back into the heterogeneous dataset to reinforce and expand the experimental dataset.

The next step in the flow diagram 300 may include performing peptide drug optimization. The optimizations may include performing gradient descent or ascent using the sequence of ingredients in the candidate drug compounds to attempt to increase or decrease certain activity levels in a design space. The results of the peptide drug optimization may be fed back into the heterogeneous datasets to reinforce and expand the experimental dataset.

FIG. 3B illustrates another high-level flow diagram 310 according to some embodiments. As depicted, a heterogeneous network of biology may be included in a knowledge graph of a biological context representation 200. Various paths or meta-paths may be expressed between nodes in the biological context representation 200. For example, the meta-paths may include indications for compound upregulates, pathway participates, disease associations, gene interactions, and compound data.

The biological context representation 200 may be translated from a first format (e.g., knowledge graph) to a format (e.g., vector) that may be processed by the AI engine 140. The AI engine 140 may use one or more machine learning models to traverse the knowledge graph by performing random walks until a corpus of random walks is generated, wherein such random walks include the indications associated with the meta-paths representing sequences of ingredients. The corpus of random walks may be referred to as a set of candidate drug compounds. A generative adversarial network using causal inference may be used to generate the set of candidate drug compounds. The set of candidate drug compounds may be stored in a higher-dimensional vector.

The AI engine 140 may compress the higher-dimensional vector of the set of candidate drug compounds into a lower-dimensional vector of the set of candidate drug compounds, depicted as biological embeddings in FIG. 3B. In some embodiments, the lower-dimensional vector may include fewer dimensions (e.g., 2, 3, . . . N) than the higher-dimensional vector (e.g., greater than N). As depicted, the nodes may be organized by the meta-path indicators and by dimension.

To output a subset of candidate drug compounds, the lower-dimensional vector of the set of candidate drug compounds may be input to one or more machine learning models 132 trained to perform classification. The classification techniques may include using clustering to filter out candidate drug compounds that produce undesirable levels of types of activity. In some embodiments, to enable the AI engine 140 to perform the classification, views presenting the levels of types of activity of each candidate drug compound in a design space may be generated using the lower-dimensional vectors. These views may also be presented to a user via the computing device 102. The machine learning models 132 may output a candidate drug candidate classified as a selected candidate drug candidate based on the clustering. For example, the selected candidate drug candidate may include an optimized sequence of ingredients that provides the most desirable levels of a certain type of activity in a design space.

Figure 4:
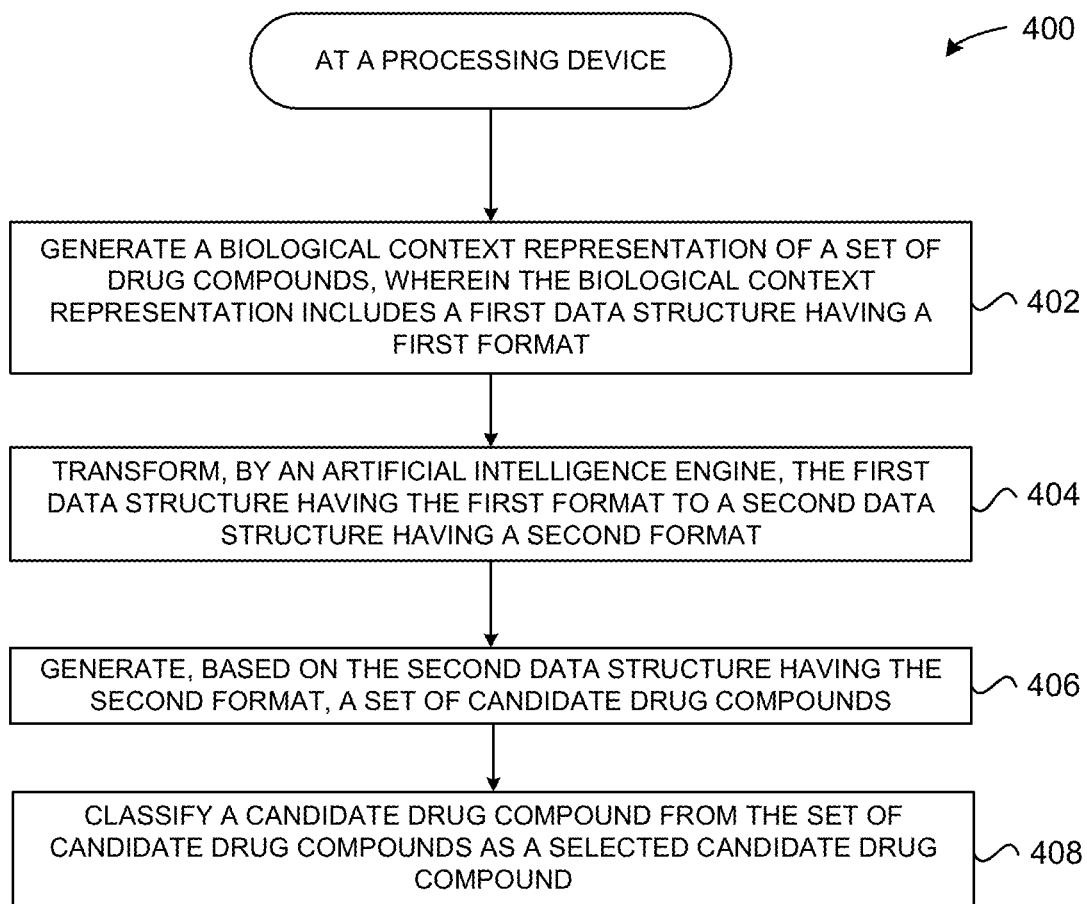
FIG. 4 illustrates example operations of a method for generating and classifying a candidate drug compound according to certain embodiments of this disclosure.

FIG. 4 illustrates example operations of a method 400 for generating and classifying a candidate drug candidate compound according to certain embodiments of this disclosure. The method 400 is performed by processing logic that may include hardware (circuitry, dedicated logic, etc.), software (such as is run on a computer system or specialized dedicated machine), or a combination of both. The method 400 or each of their individual functions, routines, subroutines, or operations may be performed by one or more processors of a computing device (e.g., any component of FIG. 1, such as server 128 executing the artificial intelligence engine 140). In certain implementations, the method 400 may be performed by a single processing thread. Alternatively, the method 400 may be performed by two or more processing threads, each thread implementing one or more individual functions, routines, subroutines, or operations of the methods. In some embodiments, one or more accelerators may be used to increase the performance of a processing device by offloading various functions, routines, subroutines, or operations from the processing device. One or more operations of the method 400 may be performed by the training engine 130 of FIG. 1.

For simplicity of explanation, the method 400 is depicted and described as a series of operations. However, operations in accordance with this disclosure can occur in various orders or concurrently, and with other operations not presented and described herein. For example, the operations depicted in the method 400 may occur in combination with any other operation of any other method disclosed herein. Furthermore, not all illustrated operations may be required to implement the method 400 in accordance with the disclosed subject matter. In addition, those skilled in the art will understand and appreciate that the method 400 could alternatively be represented as a series of interrelated states via a state diagram or events.

At 402, the processing device may generate a biological context representation 200 of a set of drug compounds. The biological context representation 200 may include a first data structure having a first format (e.g., a knowledge graph). The biological context representation 200 may include, for each drug compound of the set of drug compounds, one or more relationships between or among, without limitation, (i) physical properties data 202, (ii) peptide activity data 204, (iii) microbe data 206, (iv) antimicrobial compound data 208, (v) clinical outcome data 210, (vi) evidence-based guidelines 212, (vii) disease association data 214, (viii) pathway data 216, (ix), compound data 218, (x) gene interaction data 220, (xi) antimicrobial compound data, (xii) pro-neuroplasticity data 224, or some combination thereof.

At 404, the processing device may translate, by the artificial intelligence engine 140, the first data structure having the first format to a second data structure having a second format. The translating may include converting the first data structure having the first format (e.g., knowledge graph) to the second data structure having the second format (e.g., vector) according to a specific set of rules executed by the artificial intelligence engine 140. In some embodiments, the translating may be performed by one or more of the machine learning models 132. For example, a recurrent neural network may perform at least a portion of the translating.

The translating may include obtaining a higher-dimensional vector and compressing the higher-dimensional vector into a lower-dimensional vector (e.g., two-dimensional, three-dimensional, four-dimensional), referred to as an embedding herein. In some embodiments, one or more embeddings may be created from the first data structure having the first format. There may be any suitable number of dimensions of the embeddings. When used for classifying candidate drug compounds, the number of dimensions may be selected based on a desired performance to process the embeddings. The lower-dimensional vector may have at least one fewer dimension than the higher-dimensional vector.

At 406, the processing device may generate, based on the second data structure having the second format, a set of candidate drug compounds. In some embodiments, the generating may be performed by one or more of the machine learning models 132. For example, a generative adversarial network may perform the generating of the set of candidate drug compounds. In some embodiments, the set of candidate drug compounds may be associated with design spaces pertaining to antimicrobial, anticancer, anti-biofilm, or the like. A biofilm may include any syntrophic consortium of microorganisms in which cells stick to each other and often also to a surface. These adherent cells may become embedded within an extracellular matrix that is composed of extracellular polymeric substances (EPS).

At 408, the processing device may classify a candidate drug compound from the set of candidate drug compounds as a selected candidate drug compound. In some embodiments, the classifying may be performed by one or more of the machine learning models 132. For example, a classifier trained using supervised or unsupervised learning may perform the classifying. In some embodiments, the classifier may use clustering techniques to rank and classify the selected candidate drug compound.

In some embodiments, the processing device may generate a set of views including a representation of a design space. The design space may be antimicrobial. The processing device may cause the set of views to be presented on a computing device (e.g., computing device 102). The representation of the design space may pertain to, without limitation, (i) antimicrobial activity, (ii) immunomodulatory activity, (iii) neuromodulatory activity, (iv) cytotoxic activity, or some combination thereof. Each view of the set of views may present an optimized sequence representing the selected candidate drug compound.

The optimized sequence in each view may be generated using any suitable optimization technique. The optimization technique may include maximizing or minimizing an objective function by systematically selecting input values from a domain of values and computing the value using the objective function. The domain of values may include a subset of values from a Euclidean space. The subset of values may satisfy one or more constraints, equalities, or inequalities. A value that minimizes or maximizes the objective function may be referred to as an optimal solution. Certain values in the subset may result in a gradient of the objective function being zero. Those certain values may be at stationary points, where a first derivative at those points with respect to time (dt) is zero. The gradient may refer to a scalar-valued differentiable function (e.g., objective function) of several variables, where a point p is a vector whose components are the partial derivatives of the objective function. If the gradient is not a zero vector at a certain point p, then a direction of the gradient is the direction of fastest increase of the objective function at the certain point p.

Gradients may be used in gradient descent, which refers to a first-order iterative optimization algorithm for finding the local minimum of an objective function. To find the local minimum, gradient descent may proceed by performing operations proportional to the negative of the gradient of the objective function at a current point. In some embodiments, the optimized sequence may be found for a candidate drug compound performing gradient descent in the design space. Additionally, gradient ascent, which is the algorithm opposite to gradient descent, may determine a local maximum of the objective function at various points in the design space.

The views generated may include a topographical heatmap, itself including indicators for the least activity at points in the design space and the most activity at points in the design space. The indicator associated with the most activity may represent a local maximum obtained using gradient ascent. The indicator associated with the least activity may represent a local minimum obtained using gradient descent. The optimal sequence may be generated by navigating points between the local minima and local maxima. The optimized sequence may be overlaid on the indicators ranging from at least one least active property to an at least one most active property.

In some embodiments, the processing device may cause the selected candidate drug compound to be formulated. In some embodiments, the processing device may cause the selected candidate drug compound to be created, manufactured, developed, synthesized, or the like. In some embodiments, the processing device may cause the selected candidate drug compound to be presented on a computing device (e.g., computing device 102). The selected candidate drug compound may include one or more active ingredients (e.g., chemicals) at a specified amount.

FIGS. 5A-5D provide illustrations of generating a first data structure including a biological context representation 200 of a plurality of drug compound devices according to certain embodiments of this disclosure. The first data format may include a knowledge graph. The biological context representation 200 may capture an entire biological context by integrating every known association or relationship for each drug compound into a comprehensive knowledge graph.

Figure 5A:
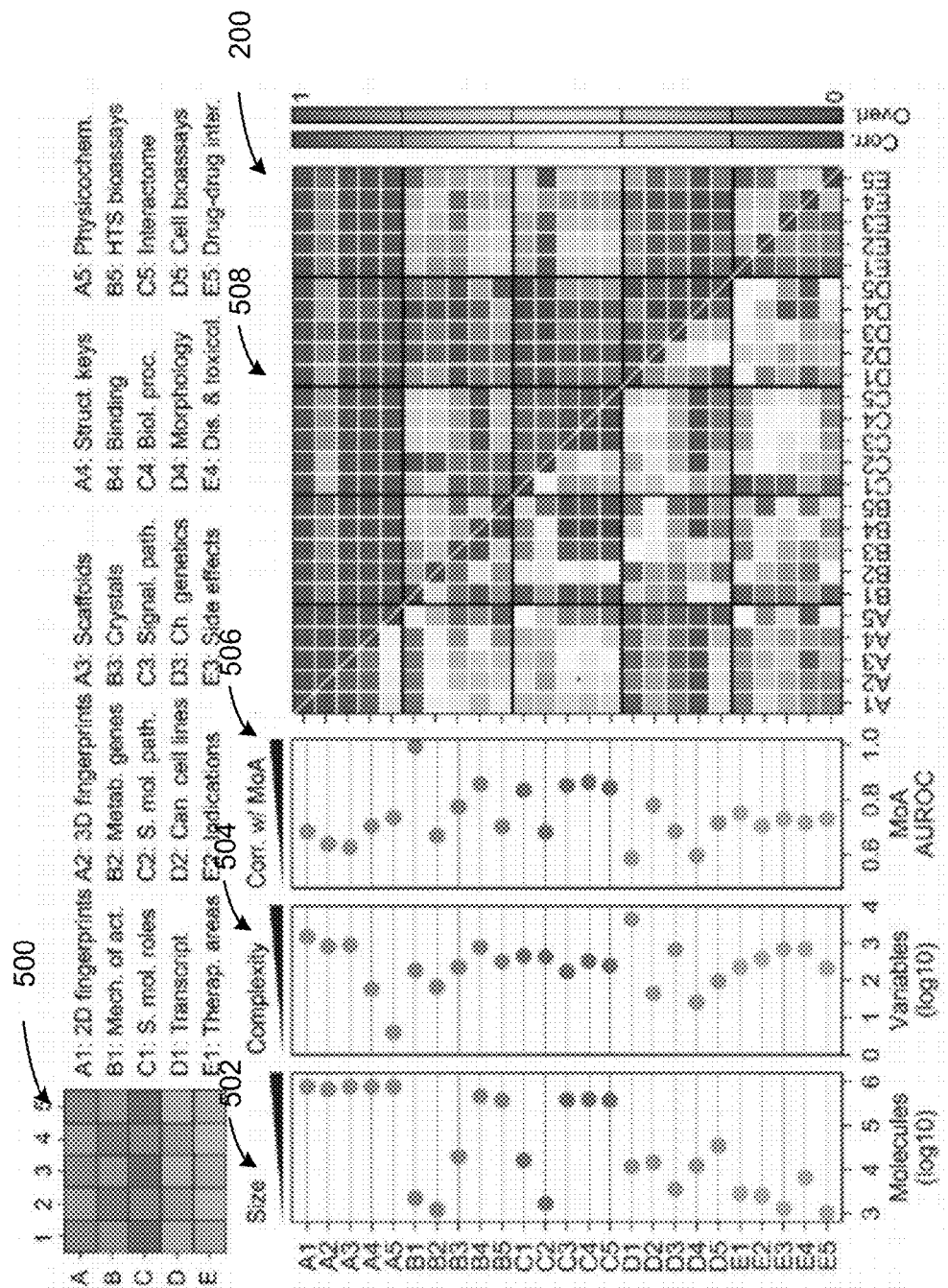
FIGS. 5A-5D provide illustrations of generating a first data structure including a biological context representation of a plurality of drug compounds according to certain embodiments of this disclosure.

FIG. 5A presents the biological context representation 200 including biomedical and domain knowledge on peptide activity, microbes, antimicrobial compounds, clinical outcomes, and any relevant information depicted in FIG. 2. A table 500 may include rows representing various categories (A, B, C, D, and E) pertaining to a biological context for each drug compound and columns representing sub-categories (1, 2, 3, 4, and 5). For example, the table includes subcategories for category A: A1 2D Fingerprints, A2 3D Fingerprints, A3 Scaffolds, A4 Structure Keys, A5 Physico-chemical/B: B1 Mechanism. Of Activity, B2 Metabolic Genes, B3 Crystals, B4 Binding, B5 High-throughput Screening Bioassays/C: C1 S. Molecular Roles, C2 S. Molecular Pathway, C3 Signal. Pathway, C4 Biological Process, C5 Interactome/D: D1 Transcript, D2 Cancer Cell Lines, D3 Chromosome Genetics, D4 Morphology, D5 Cell Bioassays/E: E1 Therapeutic Areas, E2 Indications, E3 Side Effects, E4 Disease & Toxicology, E5 Drug-drug Interaction.

Charts 502, 504, and 506 represent characteristics for each subcategory. The characteristics for chart 502 include the size of molecules, for chart 504 the complexity of variables, and for 506 the correlation with mechanism of action. Another chart 508 may represent the various characteristics of the subcategories using an indicator (such as a range of colors from 0 to 1) to express the values of the characteristics in relation to each other.

Figure 5B:
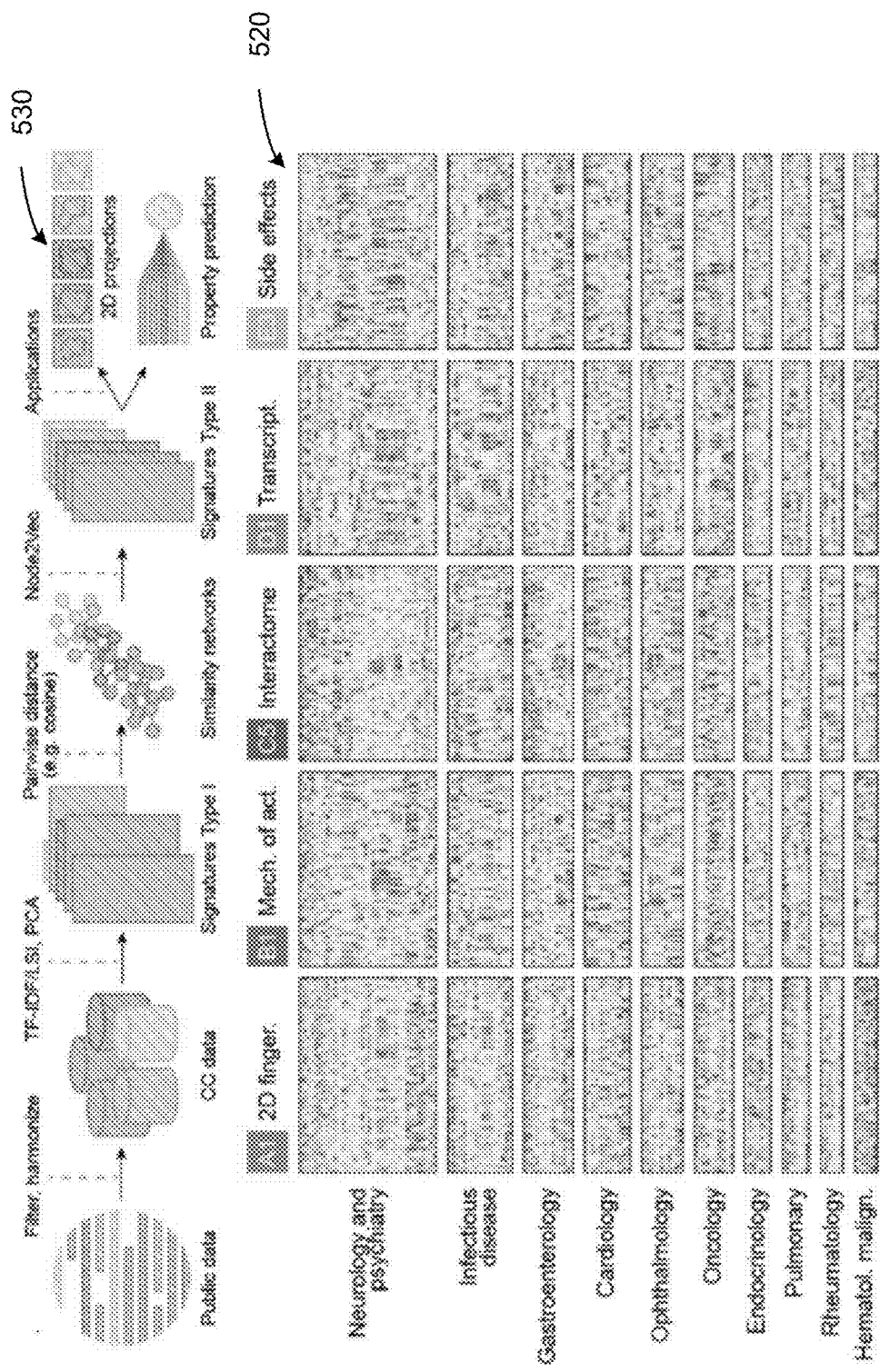

FIG. 5B illustrates a different representation 520 of characteristics for several subcategories (e.g., A1, B1, C5, D1, and E3) across different subject matter areas (e.g., neurology and psychiatry, infectious disease, gastroenterology, cardiology, ophthalmology, oncology, endocrinology, pulmonary, rheumatology, and malignant hematology.). Accordingly, the representation 520 provides an even more granular representation of the biological context representation 200 than does the chart 508. Flowchart 530 represents the process for generating candidate drugs as described further herein.

Figure 5C:
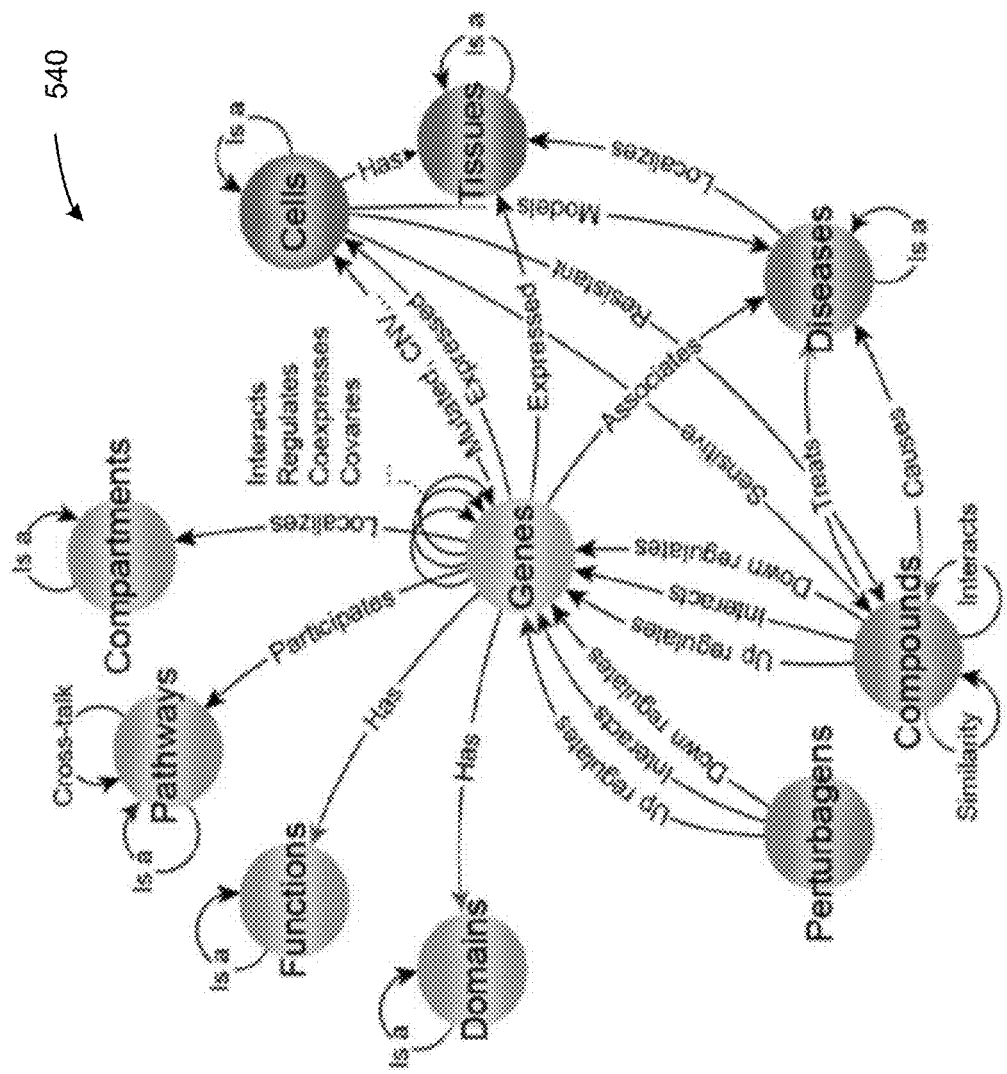
Figure 5D:
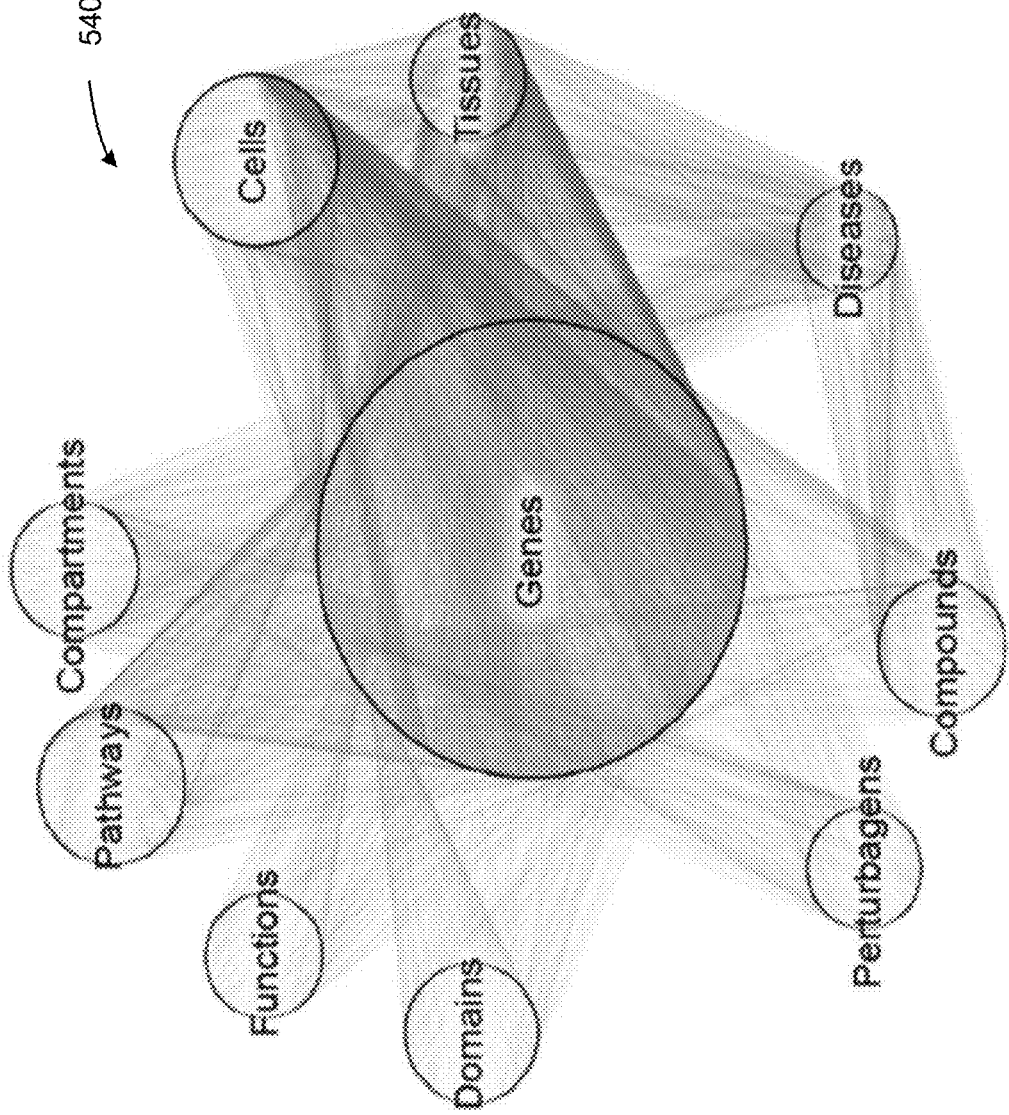

FIG. 5C illustrates a knowledge graph 540 representing the biological context representation 200. The knowledge graph 540 may refer to a cognitive map. In particular, the knowledge graph 540 represents a graph traversed by the AI engine 140, when generating candidate drug compounds having desired levels of certain types of activity in a design space. Individual nodes in the knowledge graph 540 represent a health artifact (health-related information) or relationship (predicate) gleaned and curated from numerous data sources. Further, the knowledge represented in the knowledge graph 540 may be improved over time as the machine learning models discover new associations, correlations, or relationships. The nodes and relationships may form logical structures that represent knowledge (e.g., Genes, Participates, and Pathways). FIG. 5D illustrates another representation of the knowledge graph 540 that more clearly identifies all the various relationships among the nodes.

Figure 6:
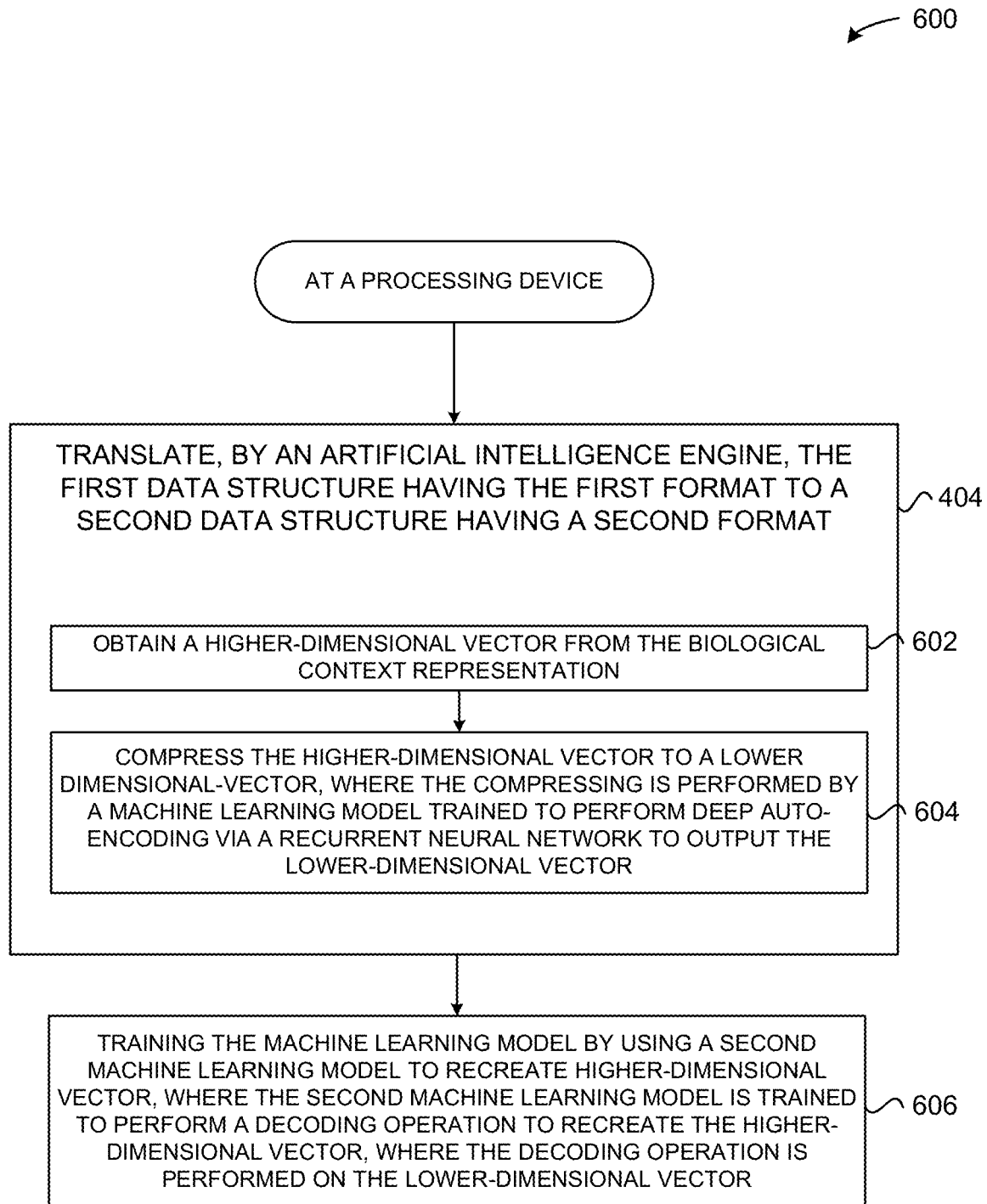
FIG. 6 illustrates example operations of a method for translating the first data structure of FIGS. 5A-5D into a second data structure having a second format according to certain embodiments of this disclosure.

FIG. 6 illustrates example operations of a method 600 for translating the first data structure of FIGS. 5A-5B a second data structure according to certain embodiments of this disclosure. Method 600 includes operations performed by processors of a computing device (e.g., any component of FIG. 1, such as server 128 executing the artificial intelligence engine 140). In some embodiments, one or more operations of the method 600 are implemented in computer instructions that are stored on a memory device and executed by a processing device. The method 600 may be performed in the same or a similar manner as described above in regard to method 400. The operations of the method 600 may be performed in some combination with any of the operations of any of the methods described herein.

The method 600 may include operation 404 from the previously described method 400 depicted in FIG. 4. For example, at 404 in the method 600, the processing device may translate, by the artificial intelligence engine 140, the first data structure having the first format (e.g., knowledge graph) to the second data structure having the second format (e.g., vector). The method 600 in FIG. 6 includes operations 602 and 604.

At 602, the processing device may obtain a higher dimensional vector from the biological context representation 200. This process is further illustrated in FIG. 7.

At 604, the processing device may compress the higher-dimensional vector to a lower dimensional-vector. The compressing may be performed by a first machine learning model 132 trained to perform deep autoencoding via a recurrent neural network configured to output the lower-dimensional vector.

At 606, the processing device may train the first machine learning model 132 by using a second machine learning model 132 to recreate the first data structure having the first format. The second machine learning model 132 is trained to perform a decoding operation to recreate the first data structure having the first format. The decoding operation may be performed on the second data structure having the second data format (e.g., two-dimensional vector).

Figure 7:
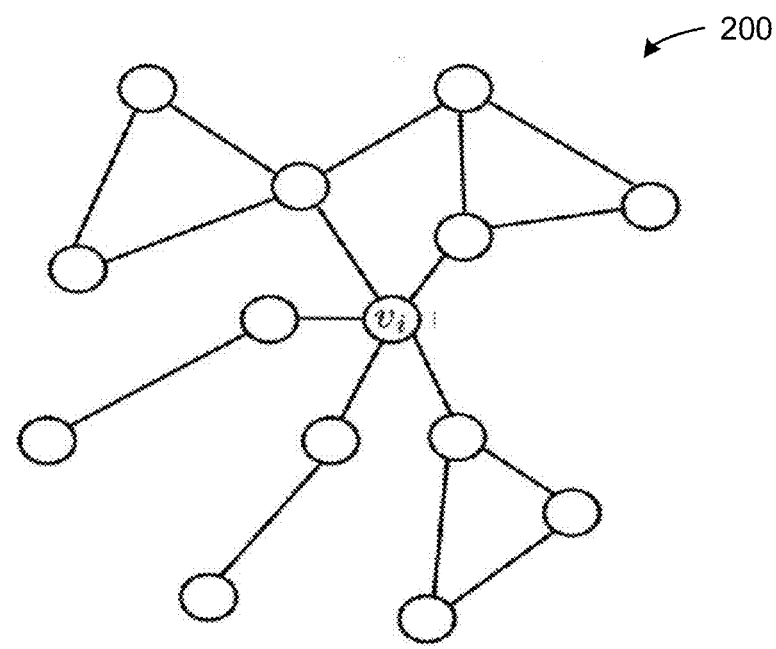
FIG. 7 provide illustrations of translating the first data structure of FIGS. 5A-5D into the second data structure having the second format according to certain embodiments of this disclosure.
Figure 7:
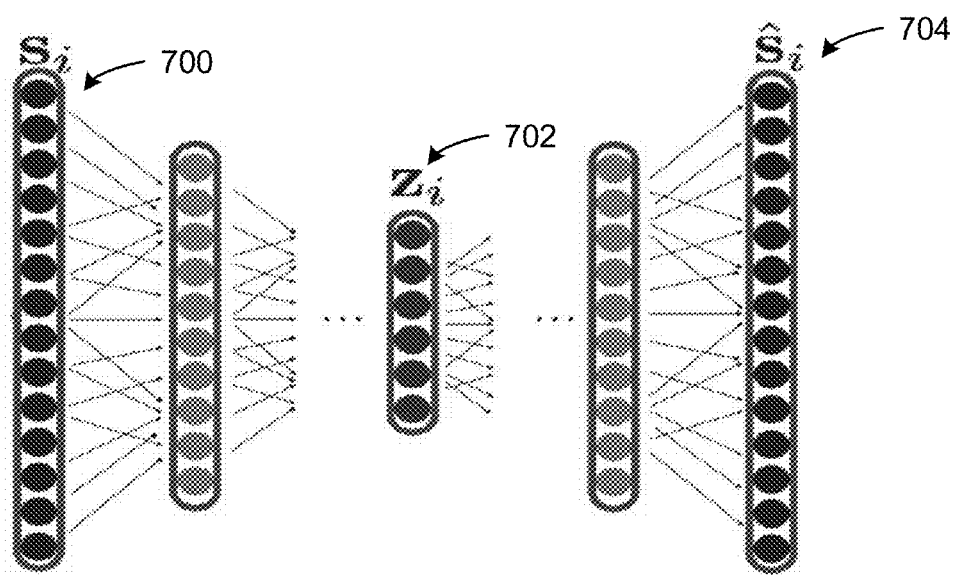

FIG. 7 provides illustrations of translating the first data structure of FIGS. 5A-5B to the second data structure according to certain embodiments of this disclosure. Aggregated biological data may be difficult to model and format correctly for an AI engine to process. Aspects of the present disclosure overcome the hurdle of modeling and formatting the aggregated biological data to enable the AI engine 140 to generate candidate drug compounds accurately and efficiently.

As depicted, a higher-dimensional vector 700 may be obtained from the biological context representation 200. Using a recurrent neural network performing autoencoding, the higher-dimensional vector is compressed to a lower-dimensional vector 702. The recurrent neural network performing autoencoding is trained using another machine learning model 132 that recreates the higher-dimensional vector 704. If the other machine learning model 132 is unable to recreate higher-dimensional vector 704 from the lower-dimensional vector 702, then the other machine learning model 132 provides feedback to the recurrent neural network performing autoencoding in order to update its weights, biases, or any suitable parameters.

Figure 8B:
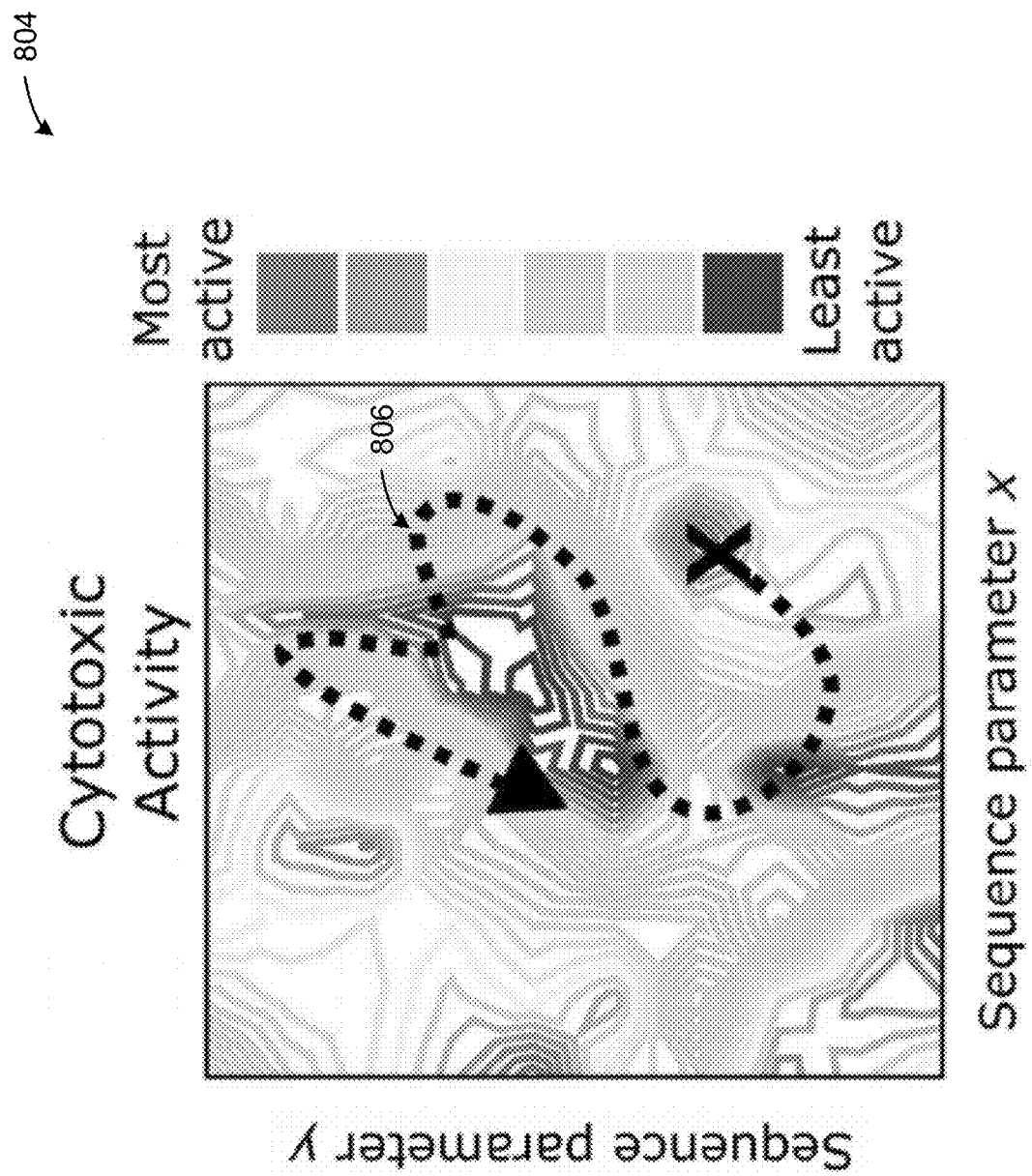
Figure 8C:
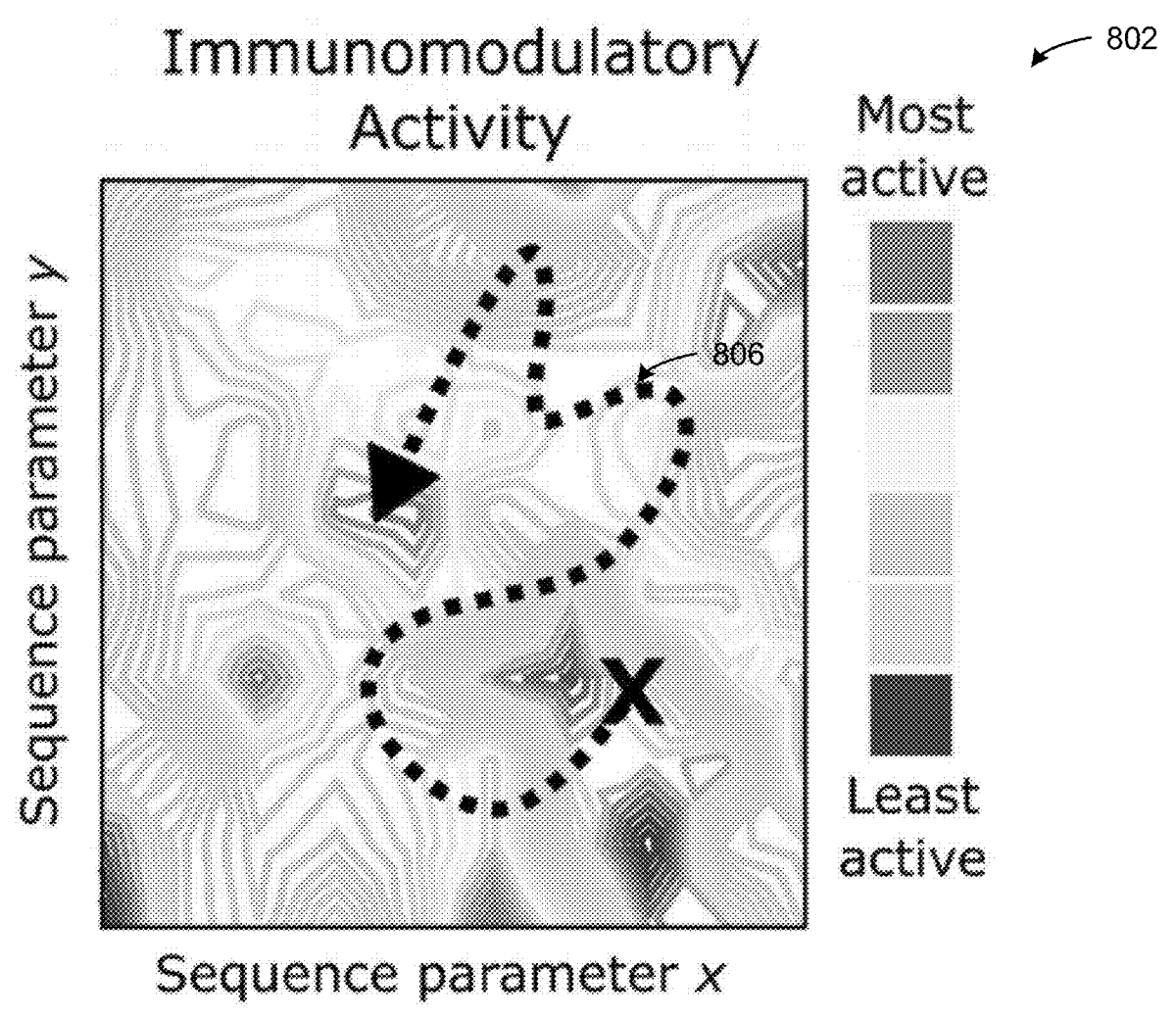

FIGS. 8A-8C provide illustrations of views of a selected candidate drug compound according to certain embodiments of this disclosure. As depicted, FIG. 8A illustrates a view 800 including antimicrobial activity, FIG. 8B illustrates a view 802 including immunomodulatory activity, and FIG. 8C illustrates a view 804 including cytotoxic activity. Each view presents a topographical heatmap where one axis is for sequence parameter y and the other axis is for sequence parameter x. Each view includes an indicator ranging from a least active property to a most active property. Further each view includes an optimized sequence 806 for a selected candidate drug compound classified by the classifier (machine learning model 132). These views may be presented to the user on a computing device 102. Further, the selected candidate drug compound 806 may be formulated, generated, created, manufactured, developed, or tested.

Figure 9:
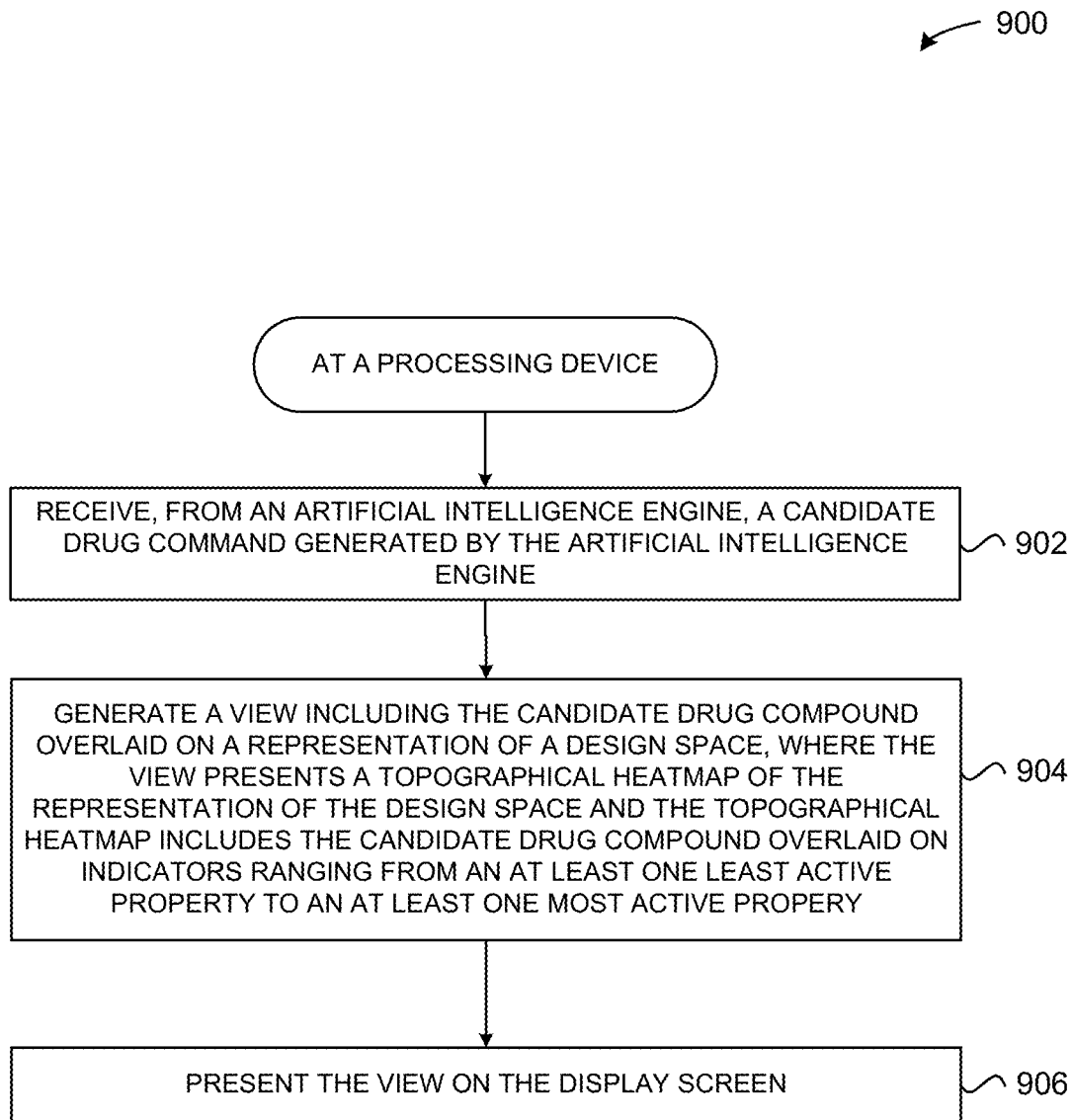
FIG. 9 illustrates example operations of a method for presenting a view including a selected candidate drug compound according to certain embodiments of this disclosure.

FIG. 9 illustrates example operations of a method 900 for presenting a view including a selected candidate drug compound according to certain embodiments of this disclosure. Method 900 includes operations performed by processors of a computing device (e.g., any component of FIG. 1, such as computing device 102). In some embodiments, one or more operations of the method 1000 are implemented in computer instructions that are stored on a memory device and executed by a processing device. The method 1000 may be performed in the same or a similar manner as described above in regards to method 400. The operations of the method 1000 may be performed in some combination with any of the operations of any of the methods described herein.

At 902, the processing device may receive, from the artificial intelligence engine 140, a candidate drug compound generated by the artificial intelligence engine 140.

At 904, the processing device may generate a view including the candidate drug compound overlaid on a representation of a design space. The view may present a topographical heatmap of the representation of the design space. The topographical heatmap may include the candidate drug compound overlaid on indicators ranging from an at least one least active property to an at least one most active property. Although a topographical heatmap is depicted as an example in the view, other suitable visual elements (e.g., graphs, charts, two-dimensional density plots, three-dimensional density plots, etc.) may be used to depict the representation of the design space.

At 906, the processing device may present the view on a display screen of a computing device (e.g., computing device 102).

Figure 10A:
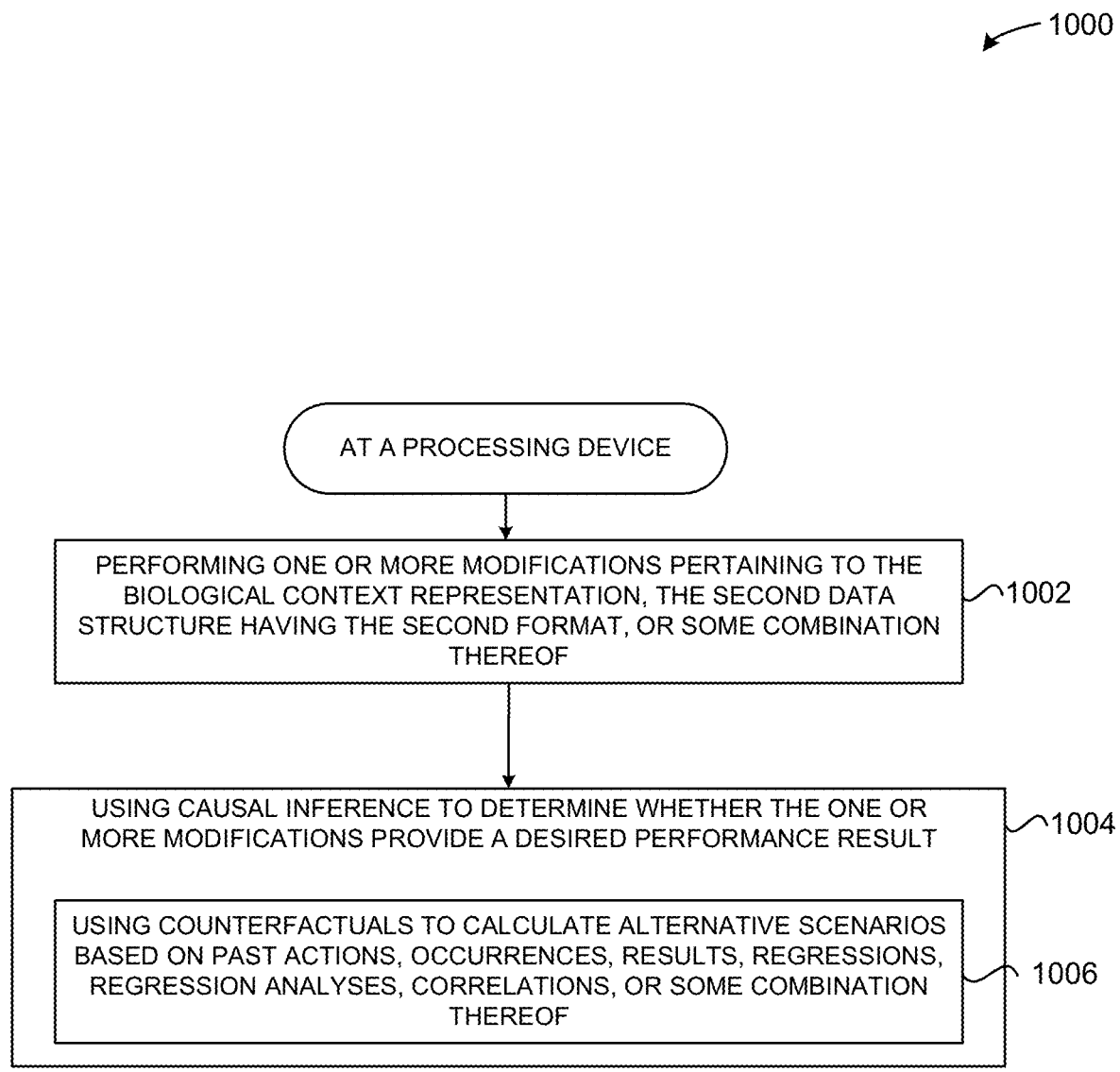
FIG. 10A illustrates example operations of a method for using causal inference during the generation of candidate drug compounds according to certain embodiments of this disclosure.

FIG. 10A illustrates example operations of a method 1000 for using causal inference during the generation of candidate drug compounds according to certain embodiments of this disclosure. Method 1000 includes operations performed by processors of a computing device (e.g., any component of FIG. 1, such as server 128 executing the artificial intelligence engine 140). In some embodiments, one or more operations of the method 1000 are implemented in computer instructions that are stored on a memory device and executed by a processing device. The method 1000 may be performed in the same or a similar manner as described above in regards to method 400. The operations of the method 1000 may be performed in some combination with any of the operations of any of the methods described herein.

At 1002, the processing device may perform one or more modifications pertaining to the biological context representation 200, the second data structure having the second format, or some combination thereof.

At 1004, the processing device may use causal inference to determine whether the one or more modifications provide one or more desired performance results. In some embodiments, using causal inference may further include using 1006 counterfactuals to calculate alternative scenarios based on past actions, occurrences, results, regressions, regression analyses, correlations, or some combination thereof. A counterfactual may refer to determining whether the desired performance still results if something does not occur during the calculation. For example, in a scenario, a person may improve their health after taking a medication. The counterfactual may be used in causal inference to calculate an alternative scenario to see whether the person's health improved without taking the medication. If the person's health still improved without taking the medication it may be inferred that the medication did not cause the health of the person to improve. However, if the person's health did not improve without taking the medication, it may be inferred that the medication is correlated with causing the health of the person to improve. There may, however, be other factors involved in conjunction with taking the medication that actually cause the health of the person to improve.

Figure 10B:
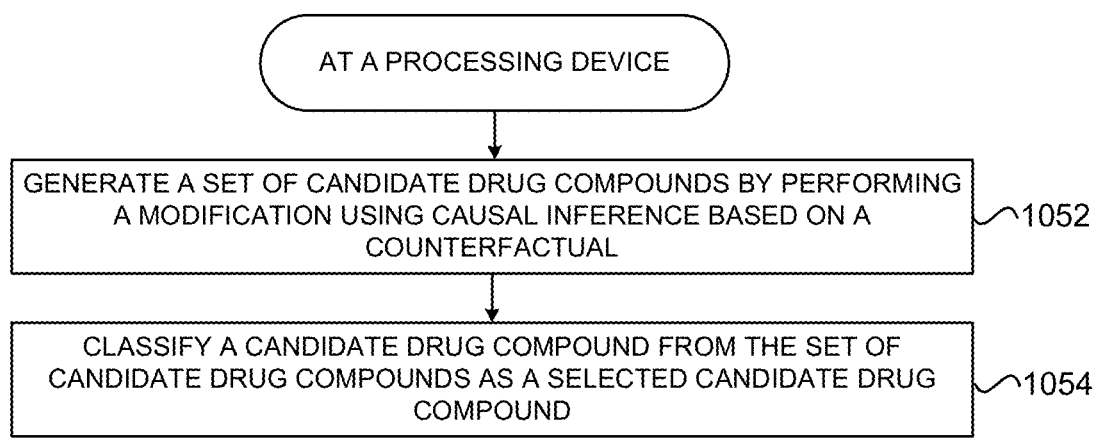
FIG. 10B illustrates another example of operations of a method for using causal inference during the generation of candidate drug compounds according to certain embodiments of this disclosure.

FIG. 10B illustrates another example of operations of method 1050 for using causal inference during the generation of candidate drug compounds according to certain embodiments of this disclosure. Method 1050 includes operations performed by processors of a computing device (e.g., any component of FIG. 1, such as server 128 executing the artificial intelligence engine 140). In some embodiments, one or more operations of the method 1050 are implemented in computer instructions that are stored on a memory device and executed by a processing device. The method 1050 may be performed in the same or a similar manner as described above in regards to method 400. The operations of the method 1050 may be performed in some combination with any of the operations of any of the methods described herein.

At 1052, the processing device may generate a set of candidate drug compounds by performing a modification using causal inference based on a counterfactual. For example, the counterfactual may include removing an ingredient from a sequence of ingredients to determine whether a candidate drug compound provides the same level or type of activity it previously provided when the ingredient was included in the sequence. If the same level or type of activity is still provided after application of the counterfactual (e.g., removal of the ingredient), then the processing device may use causal inference to determine that the ingredient is not correlated with the level or type of activity. If the same level or type of activity is not present after application of the counterfactual (e.g., removal of the ingredient), then the processing device may use causal inference to determine that the ingredient is correlated with the level or type of activity.

At 1054, the processing device may classify a candidate dug compound from the set of candidate drug compounds as a selected candidate drug compound, as previously described herein.

Figure 11:
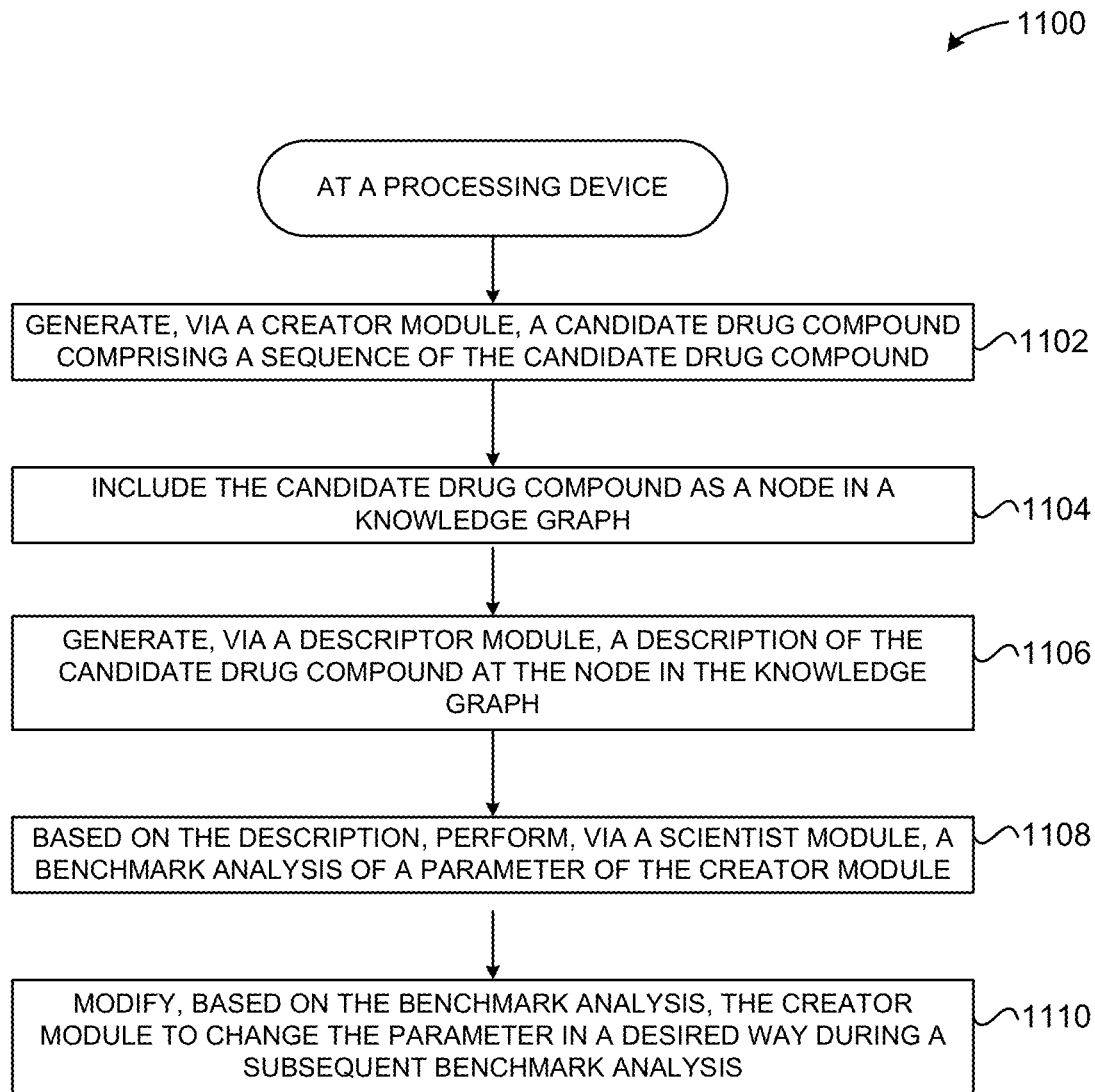
FIG. 11 illustrates example operations of a method for using several machine learning models in an artificial intelligence engine architecture to generate peptides according to certain embodiments of this disclosure.

FIG. 11 illustrates example operations of a method 1100 for using several machine learning models in an artificial intelligence engine architecture to generate peptides according to certain embodiments of this disclosure. Method 1100 includes operations performed by processors of a computing device (e.g., any component of FIG. 1, such as server 128 executing the artificial intelligence engine 140). In some embodiments, one or more operations of the method 1100 are implemented in computer instructions stored on a memory device and executed by a processing device. The method 1100 may be performed in the same or a similar manner as described above in regard to method 400. The operations of the method 1100 may be performed in some combination with any of the operations of any of the methods described herein.

At block 1102, the processing device may generate, via a creator module 151, a candidate drug compound including a sequence for candidate drug compound. The sequence for the candidate drug compound includes a concatenated vector that may include drug compound sequence information, drug compound activity information, drug compound structure information, and drug compound semantic information.

In some embodiments, the candidate drug compound may be generated using a GAN. In some embodiments, the processing device may use an attention message passing neural network including an attention mechanism that identifies and assigns a weight to a desired feature in a portion of the knowledge graph. The desired feature may be included in the candidate drug compound as drug compound semantic information, drug compound structural information, drug compound activity information, or some combination thereof.

In some embodiments, the creator module 151 may generate the candidate drug compound by performing ensemble learning by concatenating a set of encodings. The encodings may each respective sequences represented in a vector. A first encoding of the set of encodings may pertain to drug compound sequence information. A second encoding of the set of encodings may pertain to drug compound structural information. A third encoding of the set of encodings may pertain to peptide activity information. A fourth encoding of the set of encodings may pertain to drug compound semantic information.

In some embodiments, the creator module 151 may generate the candidate drug compound using an autoencoder machine learning model trained to receive a higher-dimensional vector encoding representing the candidate drug compound and output a lower-dimensional vector embedding representing the candidate drug compound. The creator module 151 may generate a latent representation using the lower-dimensional vector embedding representing the candidate drug compound.

At block 1104, the processing device may include, via the creator module 151, the candidate for the candidate drug compound as a node in a knowledge graph (e.g., biological context representation 200). In some embodiments, the knowledge graph may include a first layer including structure and physical properties of molecules, a second layer including molecule-to-molecule interactions, a third layer including molecular pathway interactions, a fourth layer including molecular cell profile associations, and a fifth layer including molecular therapeutics and indications. Indications may refer to drug indications, or the disease which gives a valid reason for clinicians to administer a specific drug.

At block 1106, the processing device may generate, via a descriptor module 152, a description of the candidate drug compound at the node in the knowledge graph. The description may include drug compound sequence information, drug compound structural information, drug compound activity information, and drug compound semantic information.

At block 1108, based on the description, the processing device may perform, via a scientist module 153, a benchmark analysis of a parameter of the creator module 151. In some embodiments, the scientist module 153 may perform causal inference using the candidate drug compound in a design space pertaining to biomedical activity (e.g., antimicrobial, anticancer, etc.) to determine if the candidate drug compound still provides a desired effect regarding the type of biomedical activity if the candidate drug compound, or the design space, is changed.

At block 1110, the processing device may modify, based on the benchmark analysis, the creator module 151 to change the parameter in a desired way during a subsequent benchmark analysis. Changing the parameter in a desired way may refer to changing a value of the parameter in a desired way. Changing the value of the parameter in the desired way may refer to increasing or decreasing the value of the parameter. Accordingly, a self-improving AI engine 140 is disclosed that increasingly generates better candidate drug components over time by recursively updating the creator module 151 based on baselines. In some embodiments, "change the parameter" means change a value of the parameter as desired (e.g., either increase or decrease).

In some embodiments, the processing device may generate, via a reinforcer module 154 based on the candidate drug compound and the description, experiments that produce desired data for the candidate drug compound. The experiments may be generated in response to the candidate drug compound and the description being similar to a real drug compound and another description of the real drug compound. For example, the reinforce module 154 may determine that certain experiments for the real drug compound elicited desired data and may select those experiments to perform for the candidate drug compound. The processing device may perform the experiments (e.g., by running simulations) to collect data pertaining to the candidate drug compound. The processing device may determine, based on the data, an effectiveness of the candidate drug compound.

Figure 12:
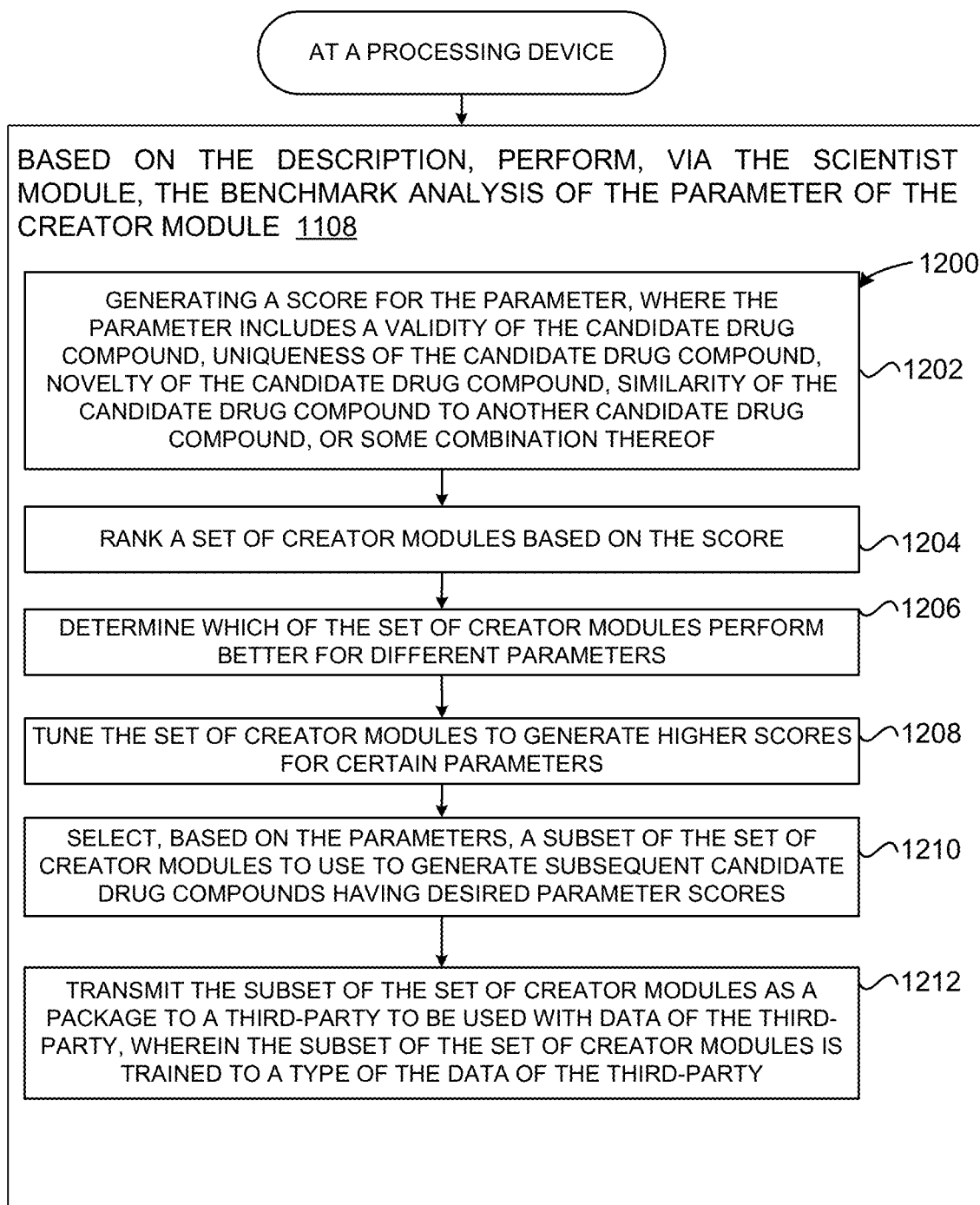
FIG. 12 illustrates example operations of a method for performing a benchmark analysis according to certain embodiments of this disclosure.

FIG. 12 illustrates example operations of a method 1200 for performing a benchmark analysis according to certain embodiments of this disclosure. Method 1200 includes operations performed by processors of a computing device (e.g., any component of FIG. 1, such as server 128 executing the artificial intelligence engine 140). In some embodiments, one or more operations of the method 1200 are implemented in computer instructions that are stored on a memory device and executed by a processing device. The method 1200 may be performed in the same or a similar manner as described above in regard to method 400. The operations of the method 1200 may be performed in some combination with any of the operations of any of the methods described herein.

The method 1200 includes additional operations included in block 1108 of FIG. 11. At block 1202, the processing device generates, via the scientist module 143, a score for a parameter of the creator module 151 that generated the candidate drug compound. The parameter may include a validity of the candidate drug compound, uniqueness of the candidate drug compound, novelty of the candidate drug compound, similarity of the candidate drug compound to another candidate drug compound, or some combination thereof.

At block 1204, the processing device may rank a set of creator modules 151 based on the score, where the set of creator modules comprises the creator module. For example, other creator modules in the set of creator modules may be scored based on the candidate drug compounds they generated. The set of creator modules may be ranked for each respective category from highest scoring to lowest scoring or vice versa.

At block 1206, the processing device may determine which creator module 151 of the set of creator modules performs better for each respective parameter. The scores of the parameters for each of the set of creator modules 151 may be presented on a display screen of a computing device. The best performing creator modules for each parameter may also be presented on the display screen.

At block 1208, the processing device may tune the set of creator modules 151 to cause the set of creator modules 151 to receive higher scores for certain parameters during subsequent benchmark analysis. The tuning may optimize certain weights, activation functions, hidden layer number, loss, and the like of one or more generative modules included in the creator modules.

At block 1210, the processing device may select, based on the parameters, a subset of the set of creator modules 151 to use to generate subsequent candidate drug compounds having desired parameter scores. For example, it may be desired to generate drug candidate compounds that result in a high uniqueness score. The creator module(s) 151 associated with high uniqueness scores may be selected in the subset of creator modules 151.

At block 1212, the processing device may transmit the subset of the set of creator modules as a package to a third-party to be used with data of the third-party. The subset of the set of creator modules may be trained to process a type of the data of the third-party. Other modules, such as the reinforce module, the descriptor module, the scientist module, and the conductor module may be included in the package delivered to the third-party. Also, a knowledge graph including data pertaining to the third-party may be included in the package. In such a way, the disclosed techniques may provide custom tailored packages that may be used by the third party to perform the embodiments disclosed herein.

Figure 13:
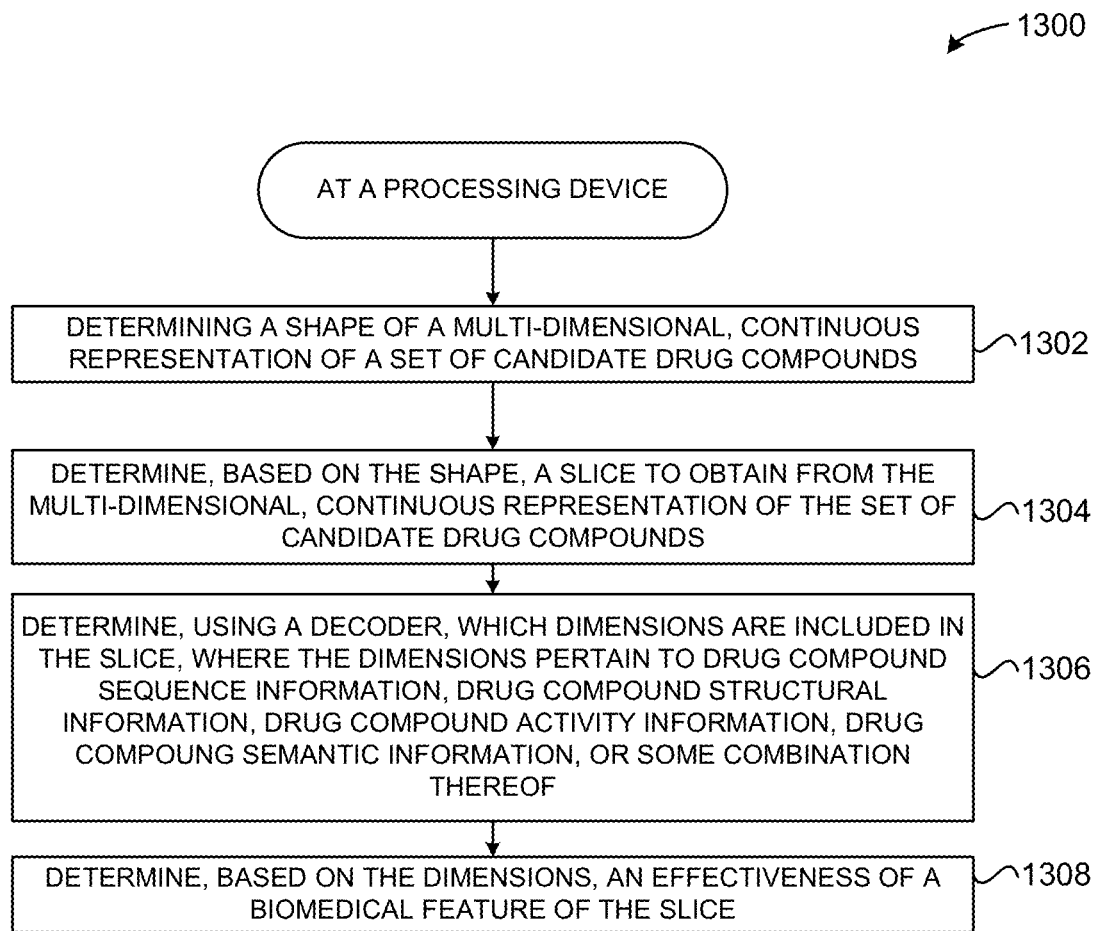
FIG. 13 illustrates example operations of a method for slicing a latent representation based on a shape of the latent representation according to certain embodiments of this disclosure.

FIG. 13 illustrates example operations of a method 1300 for slicing a latent representation based on a shape of the latent representation according to certain embodiments of this disclosure. Method 1300 includes operations performed by processors of a computing device (e.g., any component of FIG. 1, such as server 128 executing the artificial intelligence engine 140). In some embodiments, one or more operations of the method 1300 are implemented in computer instructions stored on a memory device and executed by a processing device. The method 1300 may be performed in the same or a similar manner as described above in regard to method 400. The operations of the method 1300 may be performed in some combination with any of the operations of any of the methods described herein.

At block 1302, the processing device may determine a shape of the multi-dimensional, continuous representation of the set of candidates. At block 1304, the processing device may determine, based on the shape, a slice to obtain from the multi-dimensional, multi-dimensional, continuous representation of the set of candidates. At block 1306, the processing device may determine, using a decoder, which dimensions are included in the slice. The dimensions may pertain to peptide sequence information, peptide structural information, peptide activity information, peptide semantic information, or some combination thereof. At block 1308, the processing device may determine, based on the dimensions, an effectiveness of a biomedical feature of the slice.

Figure 14:
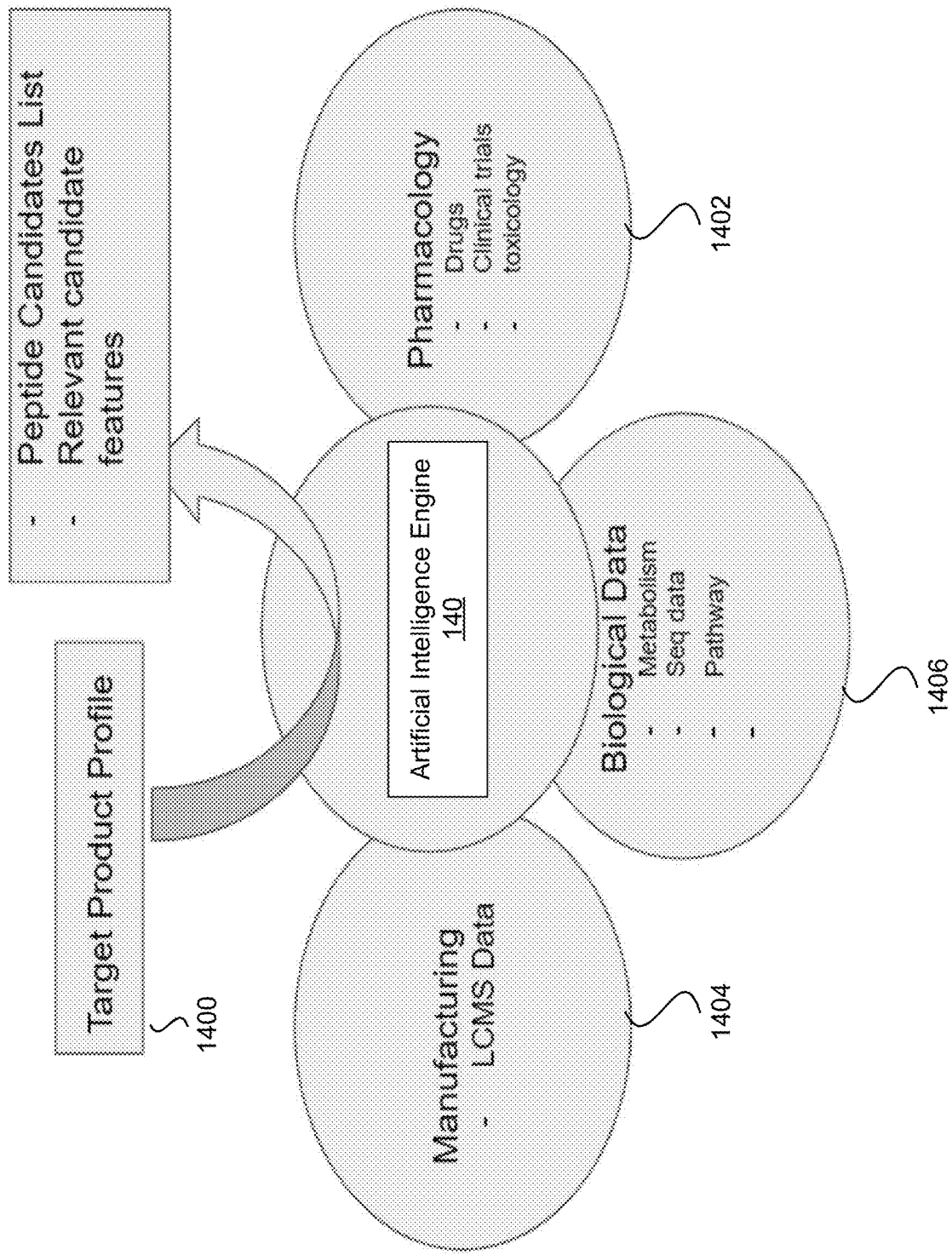
FIG. 14 illustrates a high-level flow diagram for a therapeutics tool implementing business intelligence according to certain embodiments of this disclosure.

FIG. 14 illustrates a high-level flow diagram for a therapeutics tool implementing, incorporating or using business intelligence according to certain embodiments of this disclosure. A business intelligence screen may be presented in a graphical user interface on the computing device 102. The computing device 102 may be operated by a person assigned to a development team, business intelligence team, or the like. The user interface may include various graphical elements (e.g., buttons, slider bars, radio buttons, input boxes, etc.) that enable the user to enter, select, configure, etc. a desired target product profile 1400 for sequences (e.g., peptide). The target product profile may include pharmacology data 1402 (e.g., drug brand name (if applicable), drug generic name, drug dose, clinical trial information and results, toxicology, stability, safety, efficacy, dose cost, etc.), pharmacokinetic data, pharmacodynamic data, activity data, manufacturing data 1404 (e.g., liquid chromatography mass spectrometry (LCMS) data, ability to be manufactured, scalability in production, etc.), compliance data, biological data 1406 (e.g., metabolic information (e.g., half-life, LD50, etc.), sequence data, pathway, interactions, indications, symptoms, genes, etc.), or some combination thereof. In some embodiments, while the user interface is presenting a design space for proteins, the target product profile may be entered, selected, configured, etc. via the user interface. The computing device 102 or the artificial intelligence engine 140 may select or filter the design space to present a solution space which includes sequences that match (e.g., partially or exactly) the target product profile.

The sequences may be selected, based on the target product profile, from a library of sequences. The library of sequences may be generated by one or more machine learning models 132 of the artificial intelligence engine 140 performing the techniques described herein. In some embodiments, if a certain number of sequences (e.g., 0, 5, 10, etc.) are found or not found to have a matching target product profile, then the artificial intelligence engine 140 may attempt to generate sequences having features pertinent to the target product profile. The dynamically generated sequences may be added to the library of sequences and may be presented on the user interface of the computing device 102.

The sequences that match the target product profile may include a list of candidate drug compounds (e.g., peptide candidates) or relevant candidate drug compound features. The features may include biomedical ontological relations, terms, characteristics, descriptors, or the like or non-biomedical ontological relations, terms, characteristics, descriptors, or the like. For example, the features may include levels of structural (e.g., physical, chemical, biological, etc.) information, semantic information, activity, classes of activity, indications (e.g., clinical outcomes), genes, indications, symptoms, interactions, folding properties, wave properties, stabilities of modification, sequence information (e.g., location or number of amino acids in a strand), and so forth. The user may use one or more graphical elements presented on the graphical user interface to select one or more of the sequences. Selecting the one or more sequences may cause another user interface, such as a candidate dashboard screen, to present additional data pertaining to the one or more selected sequences. In some embodiments, selecting the one or more sequences may cause the one or more sequences to be manufactured, produced, synthesized, or the like.

Figure 15:
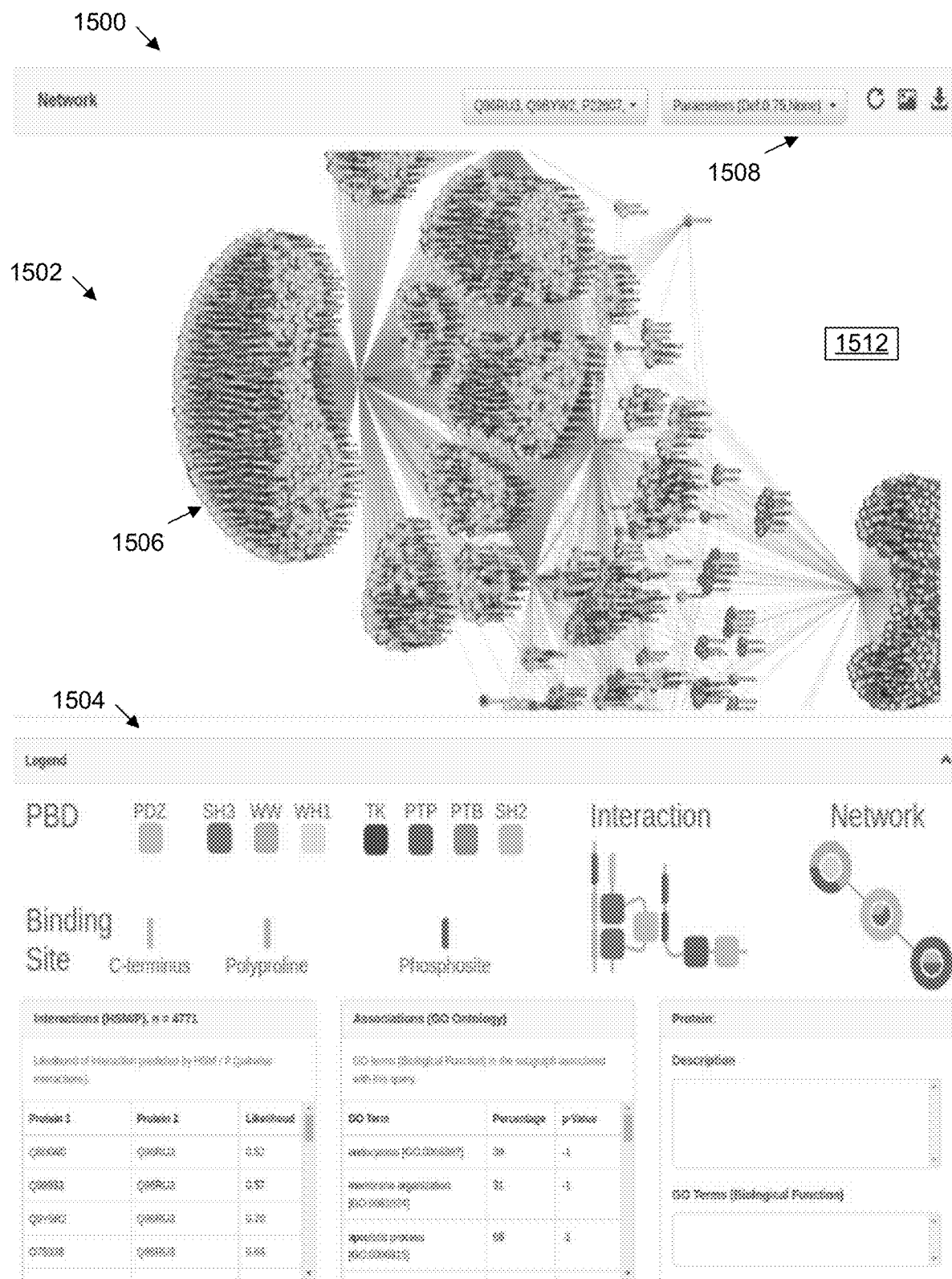
FIG. 15 illustrates an example user interface for using query parameters to generate a solution space that includes protein sequences according to certain embodiments of this disclosure.

FIG. 15 illustrates an example user interface 1500 for using query parameters to generate a solution space including protein sequences according to certain embodiments of this disclosure. The user interface 1500 includes a first portion 1502 and a second portion 1504. The first portion includes a landscape view of a solution space 1506 within a design space. Various color-coded clusters may be represented the sequences included in the solution space. The sequences are visualized as interacting with each other via connections in a network. Information pertaining to the sequences may be stored in eigenvectors and presented in any number of applicable dimensions.

The first portion 1502 includes various graphical elements to enable a user to select certain information, features, identifiers, query parameters, etc. that may be used to filter, constrain, build, generate, etc. the solution space within a design space for proteins for particular applications. The design space may include up to every conceivable or known (e.g., facts) configuration of sequences of proteins (e.g., peptides) in certain biochemical or biomedical applications (e.g., antimicrobial, anti-cancer, anti-viral, anti-fungal, anti-prion, etc.). The design space may be created based on the knowledge graph that includes ontological data pertaining to sequences of proteins for up to every conceivable or known configuration of sequences of proteins. A resolution of the design space may be modified by identifying, as a first order, features or activities pertaining to the sequences. The term "resolution" may refer to the process of reducing, partitioning or separating something into its components (e.g., features or activities pertaining to the sequences).

For example, one graphical element 1508 may include a dropdown box that enables entering, selecting, configuring, etc. one or more query parameters. Although a dropdown box is shown, any suitable graphical element may be used. The query parameters may include desirable sequence parameters associated with features, activities, properties, biomedically-related ontological relations, terms, characteristics, descriptors, or the like or non-biomedically-related ontological relations, terms, characteristics, descriptors, or the like. The query parameters may be used in any combination to generate different visualizations of solution spaces having sequences. If just one query parameter is of interest to a user (e.g., protein engineer, protein designer, peptide engineer, peptide designer, etc.), then a one-dimensional visualization of sequences related to that one query parameter may be presented in the first portion 1502. If "n" (where "n" is a positive integer) query parameters are of interest to a user, then an n-dimensional visualization of the sequences can be related to the n query parameters. The solution spaces that are generated or presented may be saved in the database 150. The artificial intelligence engine 140 may distill, based on the selected query parameters, the design space into the solution space 1506. For example, the distillation process may include selecting sequences as candidate drug compounds that produce activities (e.g., query parameters) exceeding a certain threshold level. The solution space 1506 may be generated to include those candidate drug compounds.

The user interface 1500 enables a user to modify the query parameters to essentially tune the solution space presented such that desired sequences having particular features pertaining to the query parameters are depicted at least one of efficiently, accurately, and in a condensed visual format. Such a technique is beneficial because it distills a large (typically, very large) amount of data in the knowledge graph down into a visually appealing and comprehensible format, thereby increasing explain ability and understandability. Due to the improved user interface 1500, a user's experience using the computing device may be enhanced because the user may not have to switch between or among multiple user interfaces or to perform multiple queries to find different solution spaces. The enhanced user interface 1500 may save computing resources by using the query parameters to enable data reduction from a large protein design space to salient sequences in the solution space 1506. Further, the disclosed machine learning models may be trained to generate results (e.g., solution space 1506) superior to those results produced by conventional techniques. Additionally, the results produced using the disclosed techniques may have been previously computationally infeasible using conventional techniques.

The second portion 1504 may include more granularly detailed data pertaining to the solution space 1506 and the sequences included therein. For example, the second portion 1504 includes a legend and various windows pertaining to interactions, associations, and proteins. The legend includes information pertaining to polo-box domain (e.g., the PDZ domain, SH3 domain, WW domain, WH1 domain, TK domain, PTP domain, PTB domain, SH2 domain, etc.), binding site (e.g., C-terminus, polyproline, phosphosite, etc.), interaction information, and network information. The various information is color-coded and correlated with the color-coded clusters presented in the first portion. Additionally, some of the information (e.g., polo-box domain and binding sites) in the legend is associated with different shapes to differentiate each type of information's graphics. The interaction information in the legend depicts how the various selections of polo-box domain information interact with each other, and the network information in the legend depicts how various clusters are connected in a network. Depicting the solution space using these techniques may provide an enhanced user interface by distilling a large amount of complex biochemical information about candidate drug compounds into a format easily understandable to a target user (e.g., peptide designer, business intelligence user). To make decisions pertaining to selecting candidate drug compounds without drilling down into additional screens, the user may view the user interface 1500, thereby saving computing resources and enhancing the user's experience in using the computing device 102. The window, including interactions, depicts a likelihood of pairwise interactions between two proteins. For example, "Protein 1" Q8IXWO and "Protein 2" Q96RU3 have a probability of 0.52 of interacting. The window, including associations, includes certain information pertaining to ontological terms concerning biological functions in subgraphs associated with the query that caused the solution space to be generated. The window, including protein information, includes various graphical elements (e.g., input boxes) to enable the entering of information pertaining to descriptions of the protein or ontological terms related to the protein.

The user interface 1500 may include one or more graphical elements 1512 configured to enable selecting one or more of the sequences in the solution space. The user may use the graphical element 1512 to select a sequence to view additional information pertaining to the selected sequence, to cause the selected sequence to be manufactured, produced, synthesized, etc.. For example, if a sequence selected is in the solution space, a user may be shown the topographical heatmap depicted in FIGS. 8A-8C. The sequence 806 depicted in FIG. 8A has a particular path along a traversal or feature map, where the path is specific to the query parameter entered (e.g., number of alanine amino acids). Each point on the traversal may be associated with a particular level of activity measured by one or more trained machine learning models 132 that generate the sequence 806. In some embodiments, selecting a sequence in the solution space 1506 may cause another user interface 1800 to be presented, such as a candidate dashboard screen in FIG. 18.

Figure 16:
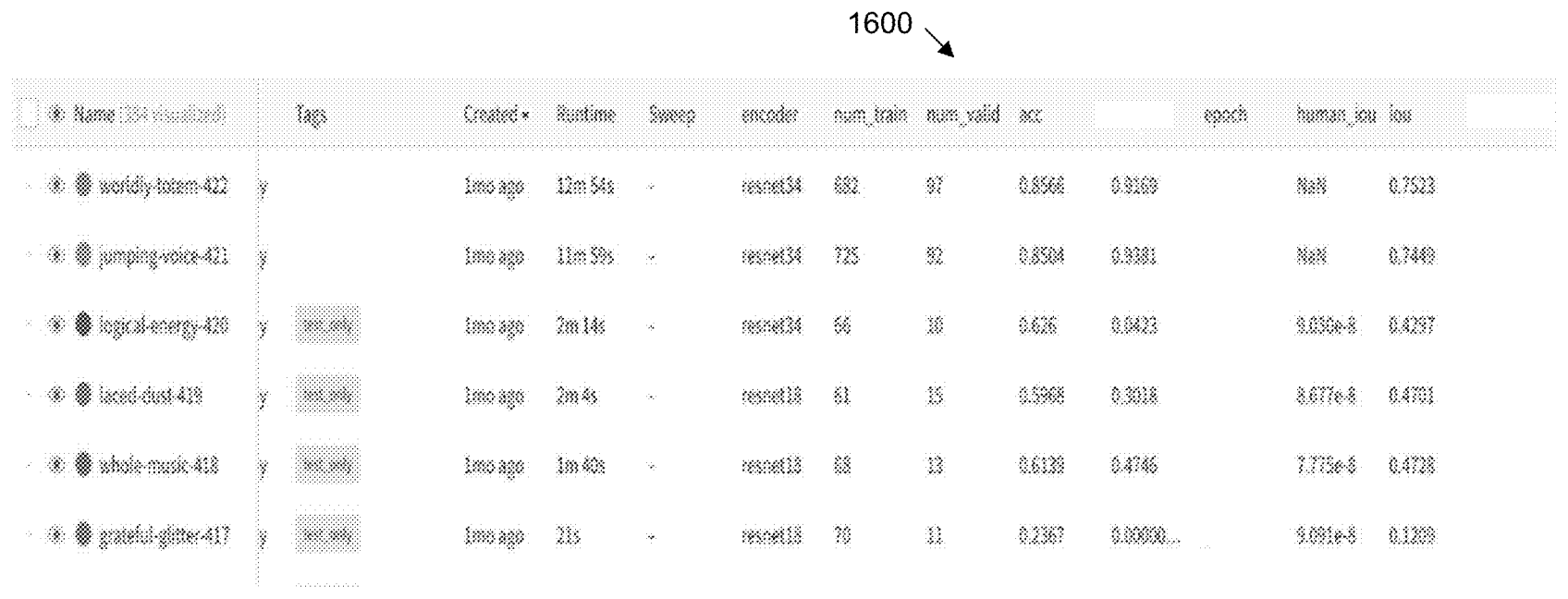

FIG. 16 illustrates an example user interface 1600 for tracking information pertaining to trials according to certain embodiments of this disclosure. The trial information includes columns for a name of the trial (computation run), a tag indicating whether the trial is a test only, a creation date (start time of execution), a runtime length, a sweep, an encoder identifier (architecture of machine learning model), a number of training data, a number of validation data, an accuracy, an epoch, a human_iou (human intersection over union), and an iou (intersection over union). Further, a feature classification metric may also be user defined. A feature may refer to a descriptor that a machine learning model 132 is learning to classify. For example, one such feature may be stability and a machine learning model 132 may classify if a peptide sequence is a stable sequence. The feature classification metric would be stability in that example. Other metrics may include accuracy, precision, intersection over union or the like. The trial information may be useful to a protein designer by enabling the protein designer to determine which trials are more successful than other trials, more accurate than other trials, and the like. Further, the trial information may enable the protein designer to generate new trials that include beneficial features of previous trials.

Figure 17:
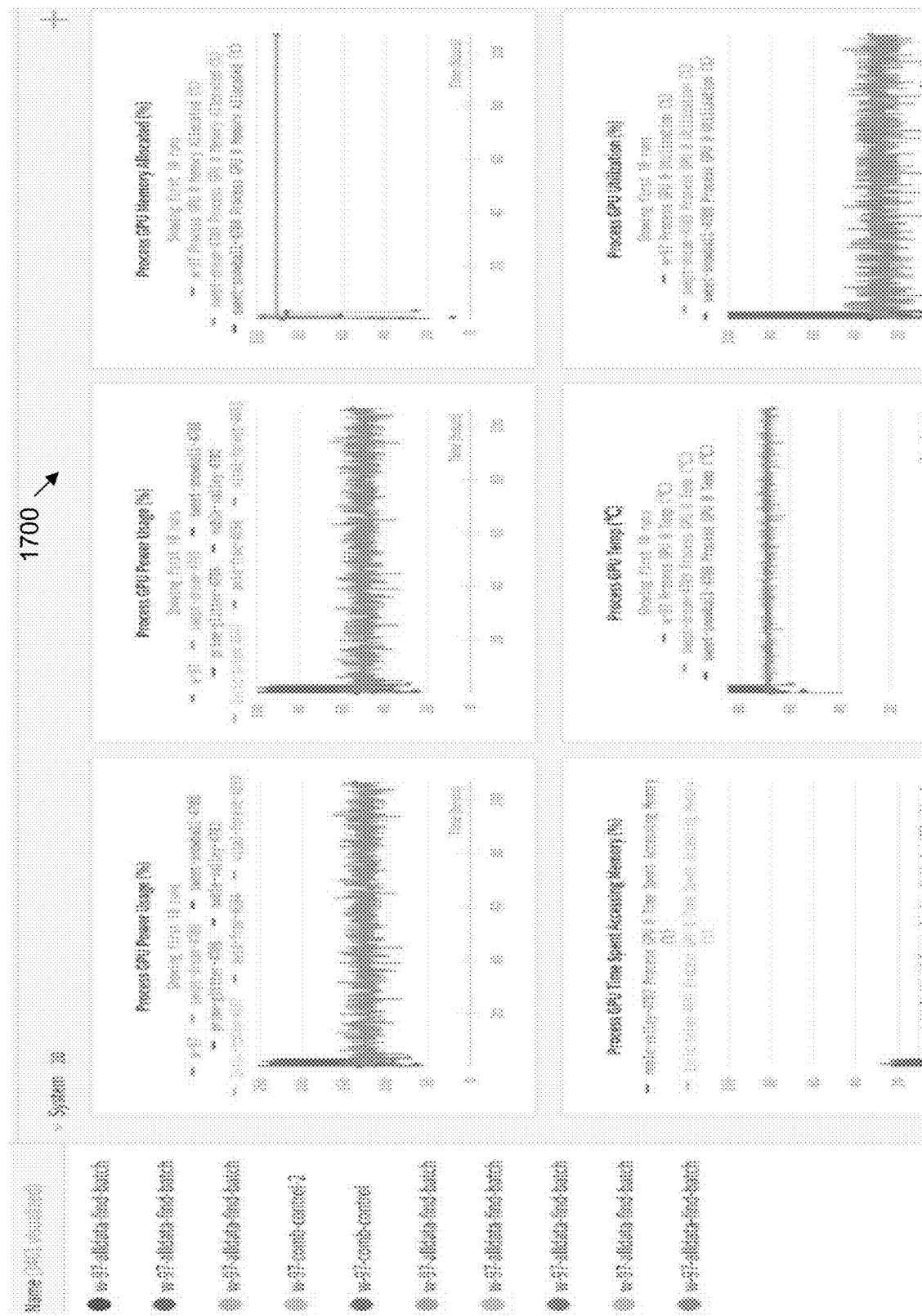
FIG. 17 illustrates an example user interface for presenting performance metrics of machine learning models that perform trials according to certain embodiments of this disclosure.

FIG. 17 illustrates an example user interface 1700 for presenting performance metrics of machine learning models that perform trials according to certain embodiments of this disclosure. As depicted, the performance metrics may include process graphic processing unit (GPU) usage (%), process GPU power usage (%), process GPU memory allocated (%), process GPU time spent accessing memory (%), and process GPU temperature (degrees, e.g., Celsius). Each metric may include a graph that includes representations (e.g., lines) associated with respective machine learning models. The graph may include an X axis corresponding to the time or time elapsed or other time measure, and a Y axis corresponding to a value amount (e.g., a cost value). The representations for each machine learning model may be overlaid on the graph to enable a comparison of how each machine learning model performed for a particular metric.

The performance metrics may be used to assign a cost value to each of the machine learning models. The cost may refer to how many resources (processor, memory, network, etc.) are used by the machine learning model during performance of trials, temperatures of components caused by the machine learning model during performance of trials, energy utilization, memory utilization, processor utilization, and other direct and indirect measures of money and non-money cost, among others. Assigning a cost (e.g., a weighted value or average as the sum of nodes traversed on a graph or as the expected value or other mathematical or statistical measure related to such cost) to each of the machine learning models may enable generating sequences that traverse the solution space to a desired location in the cheapest way possible. Accordingly, the disclosed techniques may enable saving computing resources by evaluating and assigning costs to certain machine learning models that perform better than other machine learning models.

Figure 18:
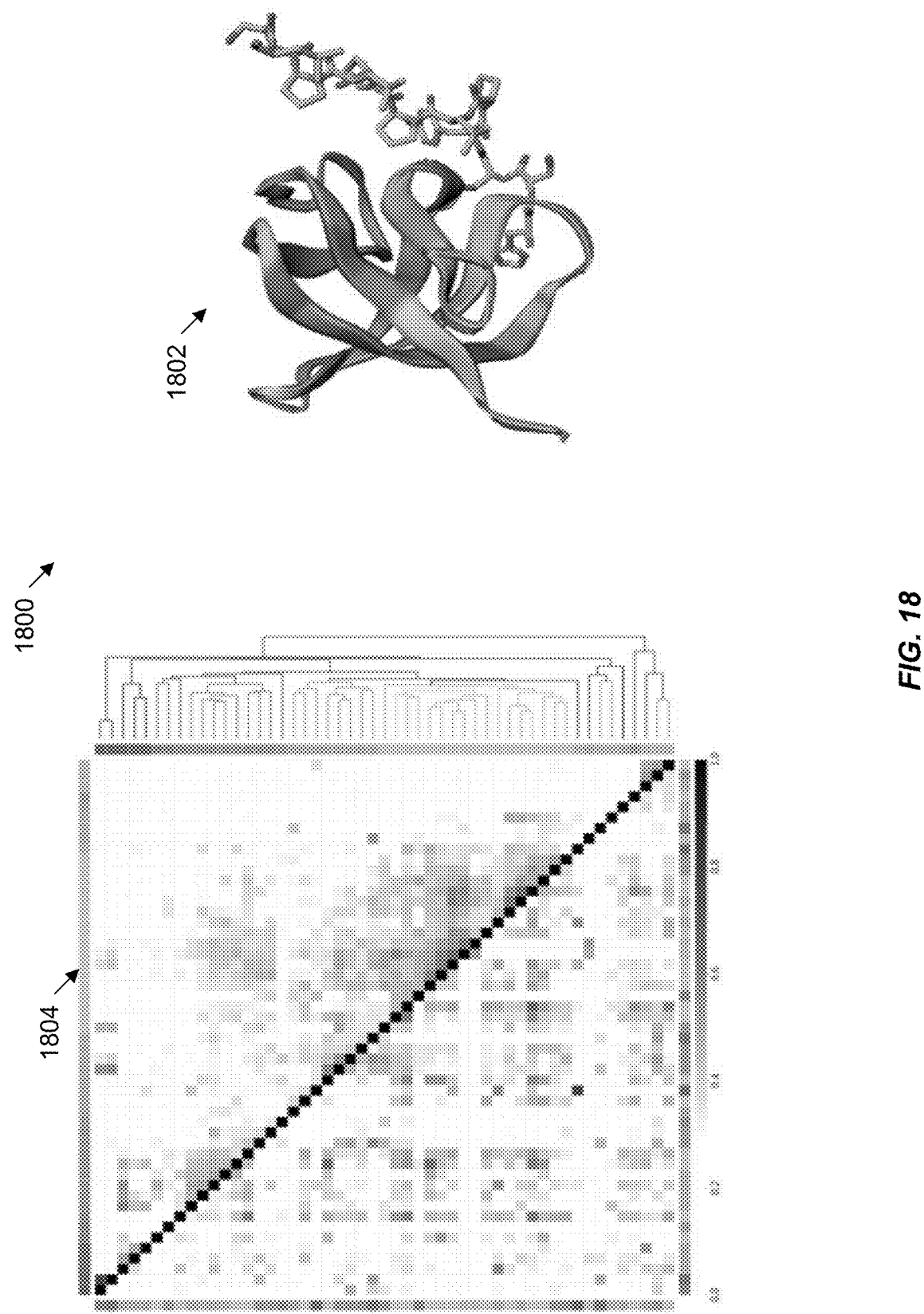
FIG. 18 illustrates an example user interface for a candidate dashboard screen according to certain embodiments of this disclosure.

FIG. 18 illustrates an example user interface 1800 for a candidate dashboard screen according to certain embodiments of this disclosure. The candidate dashboard screen includes selected information (e.g., chemical, physical, structural, chemical, semantic, etc.) about a candidate drug compound and, preferably, all of the available information thereabout. The user interface 1800 may enable a user to see a snapshot of all data (e.g., structure, correlation heatmap, related trials, trial result data, external references (aliases, synonyms, etc.)) related to a particular candidate drug compound. The user interface 1800 may be presented when a user selects a sequence in the solution space 1506 presented in FIG. 15.

The user interface 1800 includes two-dimensional 1804 and three-dimensional 1802 energy correlations. The energy correlations may correspond to energy functions associated with each position in a domain. A given energy correlation represents a correlation between each position of a protein in relation to all the other positions in the protein. The energy correlation may represent indications (e.g., color coded sections) pertaining to stability as the stability affects a specific function. An amino acid in context with the adjacent amino acids may affect the local folding properties of the peptide. Energy correlation values are inversely related (although the degree of relation may vary) to the strength of a specific amino acid (or amino acid modification) at a specific position in a peptide chain for a peptide designed for a specific function.

Figure 19:
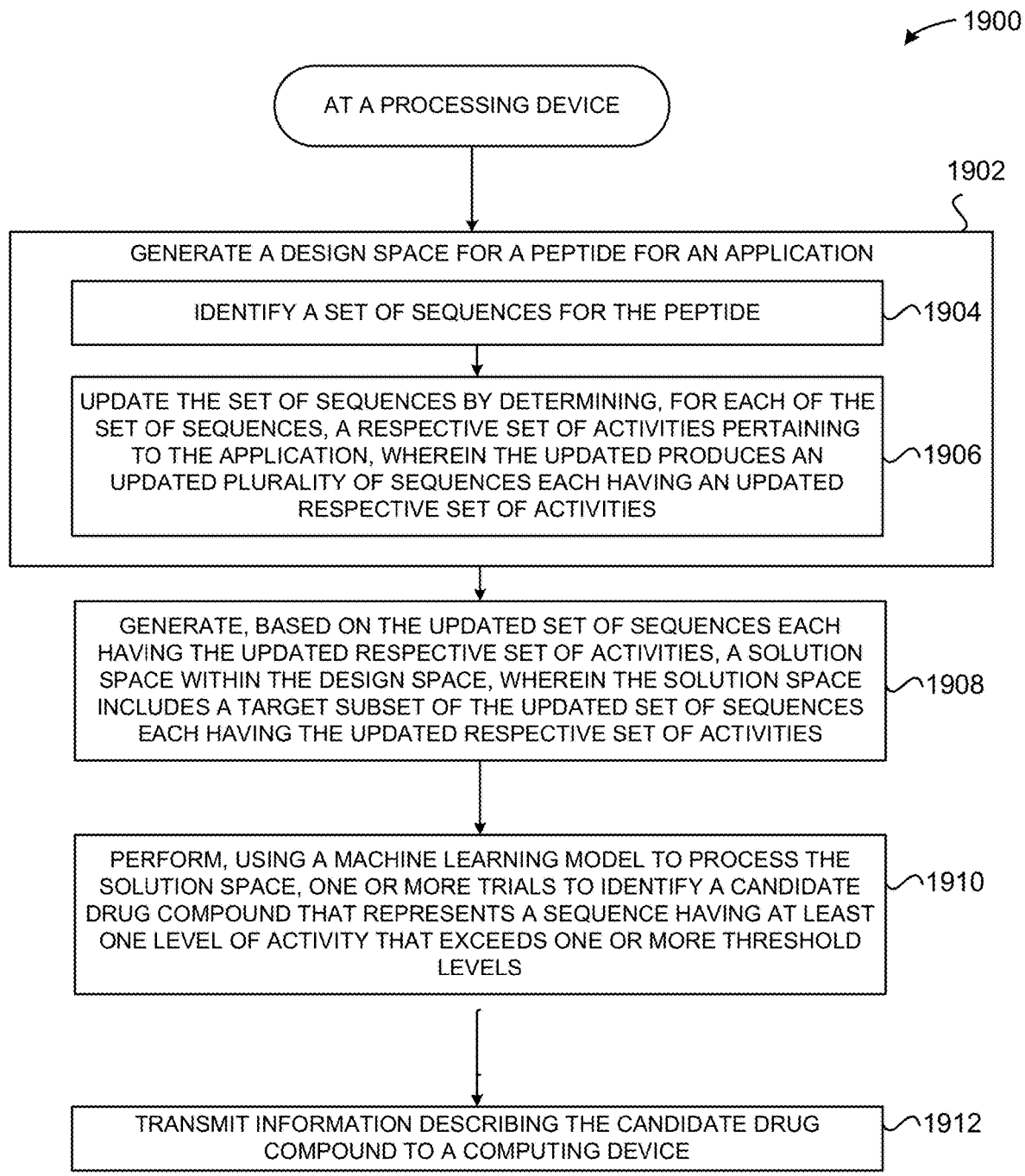
FIG. 19 illustrates example operations of a method for generating a design space for a peptide for an application according to certain embodiments of this disclosure.

FIG. 19 illustrates example operations of a method 1900 for generating a design space for a peptide for an application according to certain embodiments of this disclosure. Method 1900 includes operations performed by processors of a computing device (e.g., any component of FIG. 1, such as computing device 102, server 128 executing the artificial intelligence engine 140, etc.). In some embodiments, one or more operations of the method 1900 are implemented in computer instructions stored on a memory device and executed by a processing device. The method 1900 may be performed in the same or a similar manner as described above in regard to method 400. The operations of the method 1900 may be performed in some combination with any of the operations of any of the methods described herein.

At block 1902, the processing device may generate a design space for a peptide for an application. The application may include at least one of the following functional biomaterials (e.g., adhesives, sealants, binders, chelates, diagnostic reporters, or some combination thereof), structural biomaterials (e.g., biopolymers, encapsulation films, flocculants, desiccants, or some combination thereof), anti-infective, anti-cancer, antimicrobial, anti-viral, anti-fungal, anti-inflammatory, anti-cholinergic, anti-dopaminergic, anti-serotonergic, anti-noradrenergic, anti-prionic, and anti-fungal. The processing device may generate the design space by (i) identifying 1904 a set of sequences for the peptide, and (ii) updating 1906, the set of sequences, by determining, for each of the set of sequences, a respective set of activities (e.g., immunomodulatory activity, receptor binding activity, self-aggregation, cell-penetrating activity, anti-viral activity, peptidergic activity, cell-permeating, or the like) pertaining to the application. Updating the set of sequences may produce an updated set of sequences, wherein each updated set of sequences has an updated respective set of activities.

At block 1908, the processing device may generate, based on the updated set of sequences each having the updated respective set of activities, a solution space within the design space. The solution space may include a target subset of the updated set of sequences, wherein each updated set of sequences has the updated respective set of activities.

In some embodiments, the processing device may receive a query parameter selected, generated or transmitted from a user interface presented on the computing device 102. The processing device may use the query parameter to generate the solution space. For example, using a machine learning model trained to measure, based on the query parameter, a level of the updated respective set of activities, the processing device may generate the solution space within the design space. One or more query parameters may be selected as constraints to be used to generate the solution space. Essentially, the query parameters may be used to create bounds of the solution space within the design space. The query parameters may be selected, generated, or transmitted from a user interface presented on the computing device 102 and transmitted to the artificial intelligence engine 140. Based on the query parameters, the artificial intelligence engine 140 may use one or more machine learning models to generate the solution space within the design space.

The query parameter may include sequence parameters pertaining to biomedically-related ontological relations, terms, characteristics, descriptors, or the like or non-biomedically-related ontological relations, terms, characteristics, descriptors, or the like. For example, the biomedical ontology terms may include indications, genes, symptoms, alanine properties, etc. The non-biomedical ontology terms may include physical descriptors and characteristics, such as interactions (e.g., adhesive), folding properties (e.g., aggregating versus loose), wave properties (e.g., fluorescent, luminescent, iridescent), stability of modification (e.g., glycopeptides, lipid peptides, chelates, lasso peptides), etc.

In some embodiments, in addition to the query parameter, the processing device may receive a desired threshold level of a target activity for the query parameter, with such threshold level configured such that the target subset of sequences must exceed the threshold level in order to be included in the solution space. The desired threshold level may be any suitable value, percentage, measurement, quantity, etc. For example, a user may select a number of alanines (e.g., 5) as the query parameter and specify the desired threshold level of a target activity (e.g., immunomodulatory activity). Accordingly, the processing device may return a target subset of sequences having 5 alanines that exceed the desired threshold level of immunomodulatory activity.

In some embodiments, the processing device may perform dimension reduction to identify the target subset. Said reduction may be performed via a machine learning model using the query parameter and the updated set of sequences, using an algorithm such as uniform manifold approximation and projection (UMAP). UMAP, a nonlinear dimensionality reduction technique, may scale well on sparse data. A UMAP-based technique may use a Riemannian manifold, which refers to a real, smooth manifold M equipped with a positive-definite inner product $g_p$ on the tangent space $T_pM$ at each point p. The family $g_p$ of inner products is called a Riemannian metric. A Riemannian metric enables defining several geometric notions on the Riemannian manifold, such as an angle at an intersection, length of a curve, area of a surface and higher-dimensional analogues (e.g., volume, etc.), extrinsic curvature of sub-manifolds, and intrinsic curvature of the manifold itself. UMAP may assume that data is uniformly distributed on a locally connected Riemannian manifold and that the Riemannian metric is locally constant or approximately locally constant.

The UMAP-based technique may involve certain initial assumptions such as: (i) there exists a manifold on which the data (e.g., candidate drug compounds) would be uniformly distributed; (ii) the underlying manifold of interest is locally connected; (ii) preserving the topological structure of this manifold is the primary goal. Based on the assumptions, the UMAP-based technique may construct a graph by: (i) construct a weighted k-neighbor graph; (ii) apply some transform on the edges to ambient local distances; (iii) deal with the inherent asymmetry of the k-neighbor graph. The UMAP-based technique may perform graph layout procedures including: (i) defining an objective function that preserves desired characteristics of this k-neighbor graph; (ii) finding a low dimensional representation which optimizes this objective function.

In some embodiments, the processing device may receive a selection of a sequence from the target subset of sequences in the solution space. The selection may be made using a graphical element of a user interface presented on the computing device 102, and the selection may be transmitted from the computing device 102 to the artificial intelligence engine 140. In response to receiving the selection of the sequence, the processing device may provide information pertaining to the sequence for presentation in a user interface on the computing device 102. The information may include at least classes of proteins, protein-to-protein interactions, protein-ligand interactions, protein homology and phylogeny, sequence and structure motifs, chemical and physical stability measures, pharmacological associations, systems biology attributes, protein folding descriptors or constraints, or some combination thereof.

At block 1910, the processing device, using a machine learning model 132 to process the solution space, may perform one or more trials. The one or more trials are configured to identify a candidate drug compound that represents a sequence having at least one level of activity that exceeds one or more threshold levels. The one or more threshold levels may be predetermined or configured by a user (e.g., peptide designer). For example, the one or more threshold levels may be a value, percentage, amount, etc. that the candidate drug compound exhibits with respect to antiviral activity.

At block 1912, the processing device may transmit information describing the candidate drug compound to a computing device 102. The computing device 102 may be operated by a drug candidate designer (e.g., protein, peptide, etc.) interested in sequences that exhibit certain activity for an application. The computing device 102 may also be operated by a business user interested in sequences that have certain target product profiles (e.g., pertaining to manufacturing, pharmacology, etc.).

In some embodiments, the processing device may provide the solution space to the computing device 102 for presentation as a topographical map in a user interface of the computing device 102. The topographical map may include a set of indications that, for a sequence, each represent a level of activity at a given point on the topographical map. FIGS. 8A-8C depict examples of topographical heatmaps that may be presented on the user interface of the computing device 102. As depicted, FIG. 8A illustrates a view 800 including antimicrobial activity, FIG. 8B illustrates a view 802 including immunomodulatory activity, and FIG. 8C illustrates a view 804 including cytotoxic activity. Each view presents a topographical heatmap where one axis is for sequence parameter y and the other axis is for sequence parameter x. Each view includes an indicator (e.g., color code) ranging from a least active property to a most active property. Further, each view includes an optimized sequence 806 for a selected candidate drug compound classified by the classifier (machine learning model 132). These views may be presented to the user on a computing device 102. Further, an optimized sequence may be selected, generated or transmitted in or via the user interface using a graphical element (e.g., button, mouse cursor, etc.). The selected sequence may cause another user interface (e.g., candidate dashboard in FIG. 18) that provides additional information pertaining to the sequence to be presented. In some embodiments, selecting the sequence may cause the sequence to be formulated, generated, created, manufactured, developed, or tested.

Figure 20:
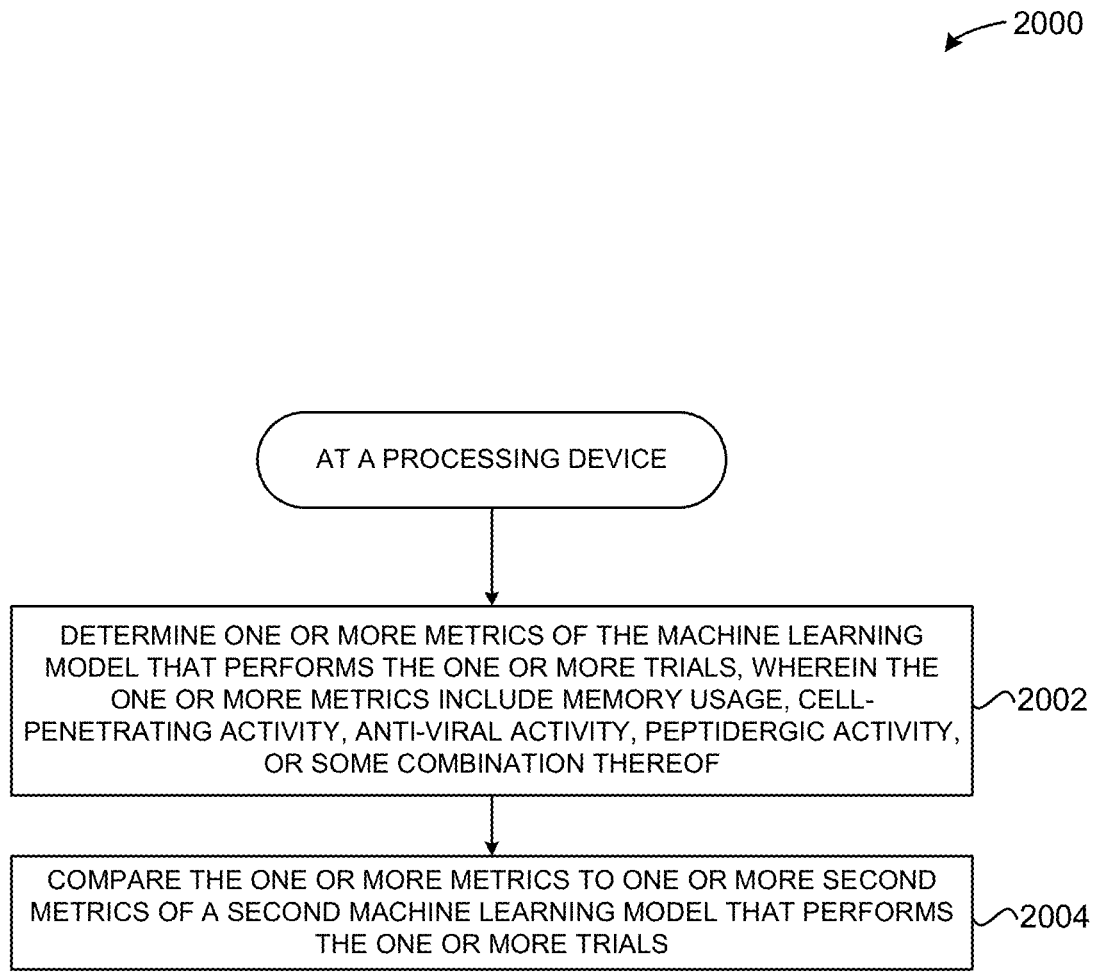
FIG. 20 illustrates example operations of a method for comparing performance metrics of machine learning models according to certain embodiments of this disclosure.

FIG. 20 illustrates example operations of a method 2000 for comparing performance metrics of machine learning models according to certain embodiments of this disclosure. Method 2000 includes operations performed by processors of a computing device (e.g., any component of FIG. 1, such as computing device 102, server 128 executing the artificial intelligence engine 140, etc.). In some embodiments, one or more operations of the method 2000 are implemented in computer instructions stored on a memory device and executed by a processing device. The method 2000 may be performed in the same or a similar manner as described above in regard to method 400. The operations of the method 2000 may be performed in some combination with any of the operations of any of the methods described herein.

At block 2002, the processing device may determine one or more metrics of the machine learning model that performs one or more trials. The one or more metrics may include memory usage, graphic processing unit temperature, power usage, processor usage, central processing usage, or some combination thereof. FIG. 17 presents examples of the one or more metrics used to analyze the machine learning model that performs the one or more trials.

At block 2004, the processing device compares the one or more metrics to one or more second metrics of a second machine learning model that performs the one or more trials. The comparison may illuminate which of the machine learning model or the second machine learning model performs better than the other. For example, the machine learning model may perform the same trials but consume less processor resources or memory resources. Accordingly, the machine learning model may be used to subsequently perform those trials and the second machine learning model may be pruned from being selected or tuned (e.g., adjusting weights, bias, levels of hidden nodes, etc.) to improve its metrics. As a result, the disclosed techniques provide a technical benefit of enabling the continuous or continual monitoring of the performance of the machine learning models and, preferably, further optimizing which machine learning models perform trials to improve metrics (e.g., processor usage, power usage, graphic processing unit temperature, etc.).

Figure 21:
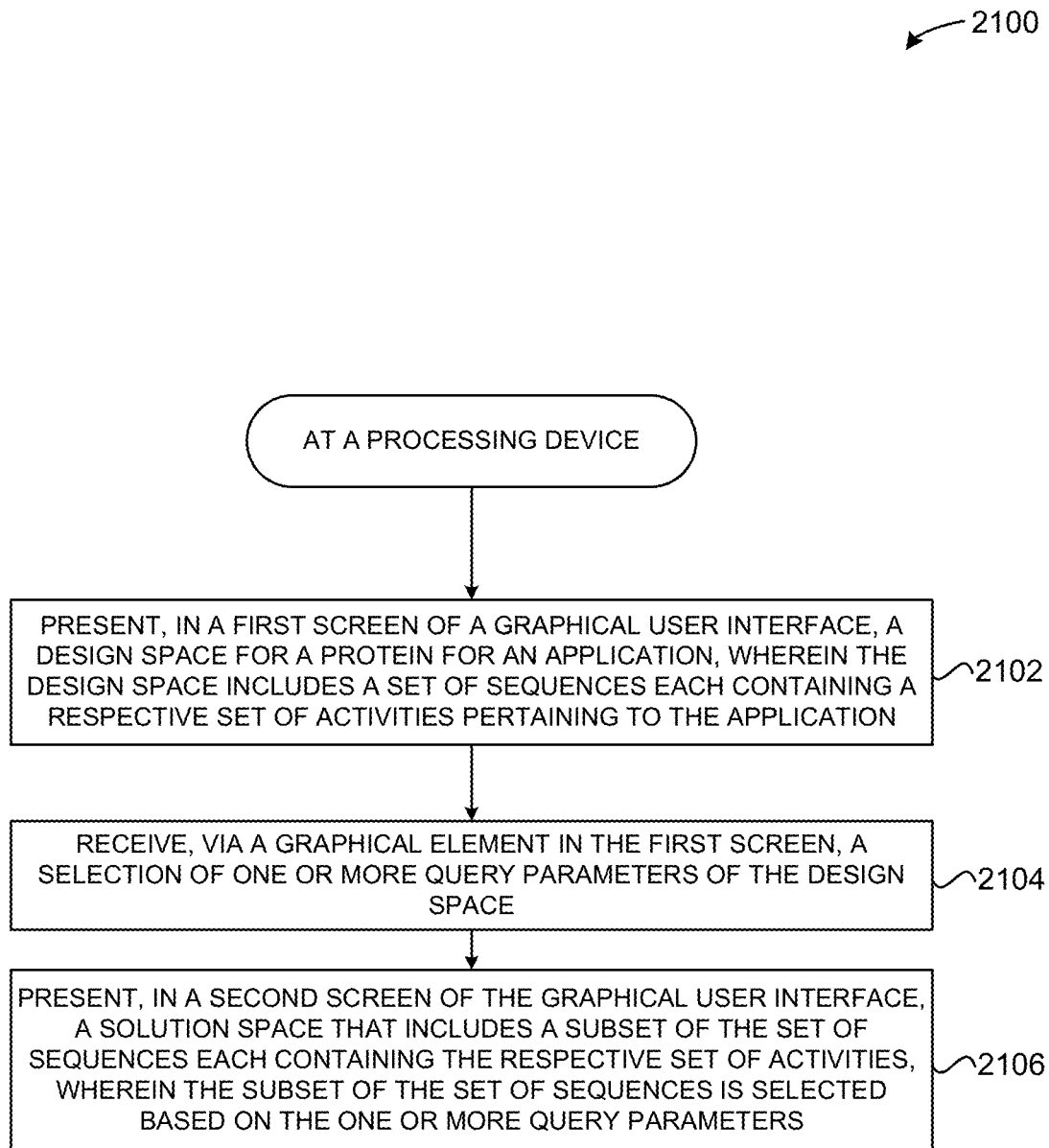
FIG. 21 illustrates example operations of a method for presenting a design space and a solution space within a graphical user interface of a therapeutics tool according to certain embodiments of this disclosure.

FIG. 21 illustrates example operations of a method 2100 for presenting a design space and a solution space within a graphical user interface of a therapeutics tool according to certain embodiments of this disclosure. Method 2100 includes operations performed by processors of a computing device (e.g., any component of FIG. 1, such as computing device 102, server 128 executing the artificial intelligence engine 140, etc.). In some embodiments, one or more operations of the method 2100 are implemented in computer instructions stored on a memory device and executed by a processing device. The method 2100 may be performed in the same or a similar manner as described above in regard to method 400. The operations of the method 2100 may be performed in some combination with any of the operations of any of the methods described herein.

At block 2102, the processing device may present, in a first screen of a graphical user interface (GUI) of a therapeutic tool, a design space for a protein for an application. In some embodiments, the therapeutic tool is a peptide therapeutic design tool, a peptide business intelligence tool, or both. In some embodiments, the protein is a peptide. The design space may include a set of sequences each containing a respective set of activities pertaining to the application. As described herein, the design space may be generated based on a knowledge graph pertaining to peptides. The design space may be presented as a two-dimensional (2D) elevation map, a three-dimensional (3D) shape, or an n-dimensional (nD) mathematical representation.

At block 2104, the processing device may receive, via a graphical element (e.g., button, input box, radio button, dropdown list, slider, etc.) in the first screen, a selection of one or more query parameters of the design space. The one or more query parameters may include a sequence parameter pertaining to biomedical ontology terms or non-biomedical ontology terms. The biomedically-related ontological relations, terms, characteristics, descriptors, etc. may pertain to indications, function (e.g., catalyze a chemical reaction (e.g., enzyme) or control a structure of water (antifreeze proteins)), activity (e.g., anti-viral, anti-microbial, anti-cancer, anti-fungal, anti-prionic, etc.), genes, symptoms, or some combination thereof. The non-biomedically-related ontological relations, terms, characteristics, descriptors, etc. may pertain to physical characteristics, descriptors, or some combination thereof. Example physical characteristics and descriptors may include information pertaining to interactions (e.g., adhesive properties), folding properties, (e.g., aggregating versus loose), wave properties (e.g., fluorescent, luminescent, iridescent, etc.), measures of stability of modification (e.g., with respect to glycopeptides, lipid peptides, chelates, lasso peptides, etc.), and the like.

At block 2106, the processing device may present, in a second screen of the GUI, a solution space that includes a subset of the set of sequences, each sequence containing the respective set of activities. The subset of the set of sequences is selected based on the one or more query parameters. In some embodiments, the solution space may be generated within the design space by one or more machine learning models 132 trained to measure, based on the one or more query parameters, a respective level of one or more of the respective set of activities of each of the set of sequences in the subset of sequences. The query parameters essentially create the bounds of the solution space within the design space. Generating the solution space may include grouping or binning, based on the query parameter, sequences as possible or not possible. "Possible," as used herein, means constructable in reality, economically feasible, chemically feasible, biologically feasible, or otherwise reasonably feasible. "Not possible," as used herein, means not able to be constructed in reality, economically infeasible, chemically infeasible, biologically infeasible, or otherwise reasonably infeasible. In some embodiments, the machine learning model 132 may be a variational autoencoder, as described herein. In some embodiments, the machine learning model 132 may be any suitable machine learning model capable of performing decomposition methods.

In some embodiments, the solution space is presented as a topographical map in the GUI. The topographical map may include a set of indications, wherein each set of indications represents a level of activity for a sequence associated with a given point on the topographical map. In some embodiments, the second screen may include a first portion presenting one or more clusters (e.g., color-coded) representing the subset of the set of sequences. As shown in FIG. 15, the first portion may depict how, in a network, the clusters are organized and interact with each other.

In some embodiments, the one or more color coded clusters may represent, using an energy correlation, each sequence in the subset. The energy correlation may include a correlation between each position of each sequence in the subset and other positions of other sequences in the subset. The term "energy correlation" may refer to stability as it affects a specific function of the subset of sequences, or it may also refer to, e.g., a strength of an amino acid in a sequence relative to a strength of another amino acid at a different position in the sequence. For example, an amino acid in context with an adjacent amino acid affects the local folding properties of a peptide. Energy correlation values are, to some degree, inversely related to a strength of a specific amino acid (or amino acid modification), where the amino acid is located at a specific position in the peptide chain.

Thus, the first portion visually represents high-level general information pertaining to the set of sequences in the solution space. The visual representation of the solution space may provide an enhanced user interface to a protein designer. For example, by visually depicting the interactions of the clusters representing the set of sequences in a network, a protein designer may be provided with a vast amount of information cognitively understandable by a user in a single user interface without the user's having to view numerous user interfaces to perform additional queries as to how sequences interact with other sequences in a network.

The second screen may include a second portion presenting data pertaining to the subset of the set of sequences represented by the one or more clusters. The data presented in the second portion may be more granular and detailed than the data in the clusters presented in the first portion of the second screen. The second portion may include a legend and various windows, including detailed data, as described above with reference to FIG. 15. The detailed data may enable a protein designer to drill-down to understand very specific information about the clusters presented in the solution space. The specific information may pertain to polo-box domains (PBD), binding sites, interactions, network, associations, biological functions, and the like. The detailed data may describe one or more objects associated with the subset of the set of sequences. The one or more objects may include a candidate drug compound, an activity, a drug, a gene, a pathway, a physical descriptor, an interaction (e.g., adhesive, etc.), a folding property (e.g., aggregating versus loose), a wave property (e.g., fluorescent, luminescent, iridescent, etc.), a stability of modification (e.g., glycopeptides, lipid peptides, chelates, lasso peptides, etc.), or some combination thereof.

In some embodiments, the processing device may receive, using a graphical element (e.g., button, mouse cursor, input box, dropdown list, slider, radio button, etc.) of the second screen, a selection of a sequence from the subset of the set of sequences. The selection may be based on the sequence being previously untraversed. To that end, the processing device may store each sequence included in the subset presented in the solution space and may track whether the sequence has been generated or traversed before. The processing device may store an indicator (e.g., flag) with each sequence in the database 150, and the indicator may represent whether the respective sequence has been traversed or is or remains untraversed. In some embodiments, the sequence traversed may be presented in a first manner (e.g., with a particular color) while the sequence untraversed may be presented in a second manner (e.g., with a different color than the first manner). In some embodiments, the second screen may provide a graphical element that enables filtering to view only the sequences traversed or, alternatively, untraversed. Responsive to the selection of the sequence, the processing device may present, in the second screen, additional information pertaining to the sequence. The additional information may include a candidate drug compound, an interaction, an activity, a drug, a gene, a pathway, or some combination thereof.

In some embodiments, the processing device may receive, using a graphical element of the second screen, a selection of a sequence from the subset of the set of sequences. The processing device may present, in a third screen, a candidate dashboard (e.g., candidate dashboard screen of FIG. 18) including information pertaining to the selected sequence. The information may pertain to a structure of the sequence, a correlation heatmap, experimental data, a list of probabilistic scores generated by one or more inference models, external data related to the sequence (e.g., all related external data to a specific peptide, such as database IDs, aliases, synonyms, etc.), or some combination thereof. In some embodiments, the list of probabilistic scores may be represented as violin plots detailing a success probability of the sequence in a specific function (e.g., activity such as anti-viral, anti-microbial, anti-fungal, anti-prionic, etc.) across a set of conditions (e.g., query parameters).

In some embodiments, the processing device may receive, in the GUI, one or more parameters pertaining to one or more machine learning models 132 of the artificial intelligence engine 140. The one or more parameters may refer to hyper parameters and may pertain to one or more constraints (e.g., epochs, batch sizes, attention, processor usage, memory usage, execution time, etc.) for the one or more machine learning models to implement when using the solution space to perform one or more trials.

In some embodiments, the processing device may receive, using a graphical element of the second screen, a selection of a sequence from the subset of the set of sequences. The processing device may cause the sequence to be manufactured, synthesized, or produced.

Figure 22:
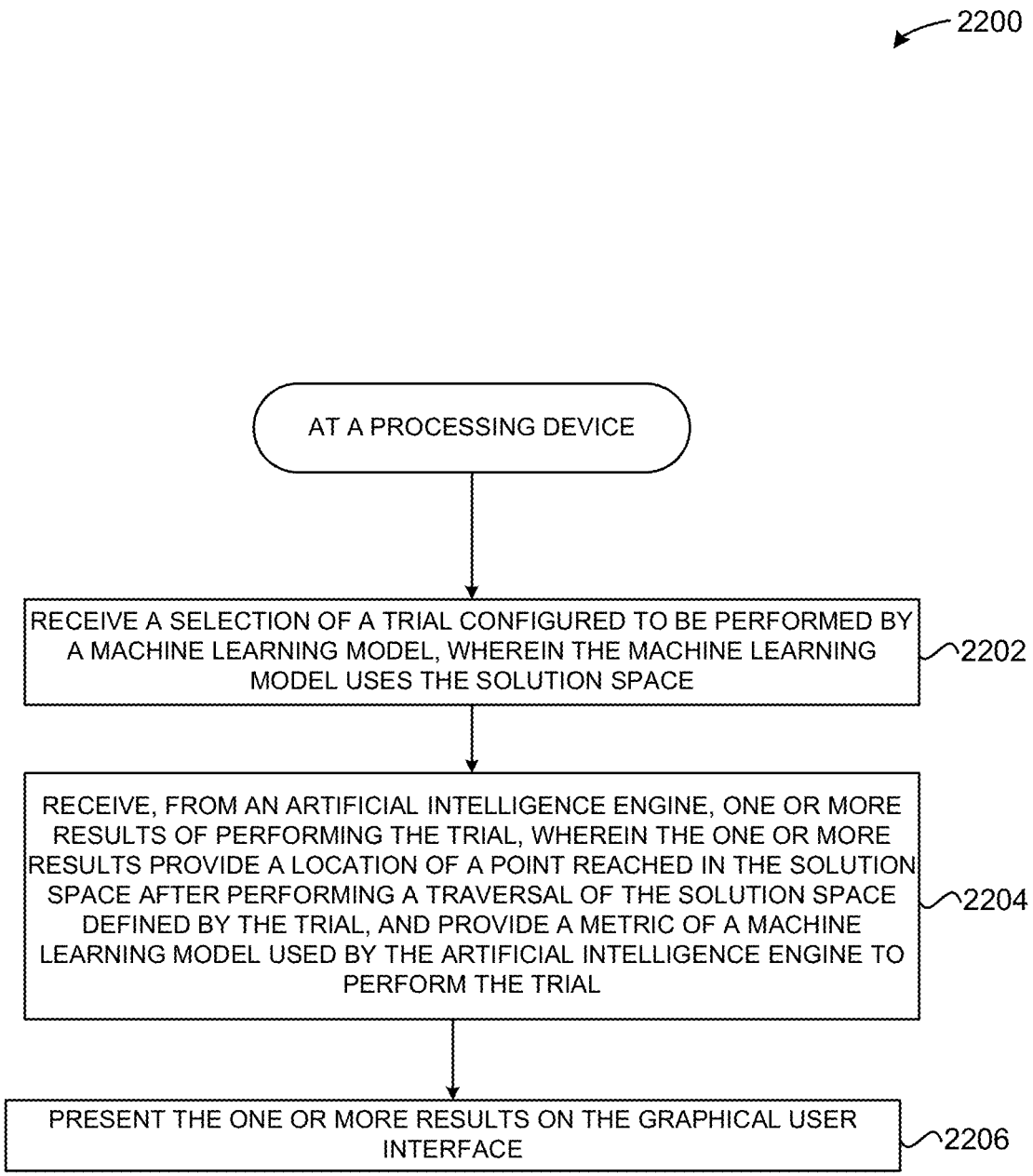
FIG. 22 illustrates example operations of a method for receiving and presenting of one or more results of performing a selected trial using a machine learning model according to certain embodiments of this disclosure.

FIG. 22 illustrates example operations of a method 2200 for receiving and presenting of one or more results of performing a selected trial using a machine learning model according to certain embodiments of this disclosure. Method 2200 includes operations performed by processors of a computing device (e.g., any component of FIG. 1, such as computing device 102, server 128 executing the artificial intelligence engine 140, etc.). In some embodiments, one or more operations of the method 2200 are implemented in computer instructions stored on a memory device and executed by a processing device. The method 2200 may be performed in the same or a similar manner as described above in regard to method 400. The operations of the method 2200 may be performed in some combination with any of the operations of any of the methods described herein.

At block 2202, the processing device may receive a selection of a trial configured to be performed by a machine learning model 132. The machine learning model may use the solution space generated, as described with reference to FIG. 23. The trial may include traversing the solution space according to a specific route, a random route, or a combination of a specific route and a random route. The traversal may result in points having different activities in the solution space. The points may represent a sequence and may be referred to as a candidate drug compound herein. The traversal may specify a particular location of a point as a starting point or a particular location of a destination point. The traversal may or may not specify the route to traverse to get from the starting point to the destination point. In some embodiments, the traversal may just specify a starting point or a destination point and the machine learning model 132 may randomly traverse the solution space to generate different sequences having different activities. While traversing the surface of the solution space, the one or more machine learning models 132 may be trained to perform maximization functions or minimization functions. For example, the machine learning model may measure level of activity at some or all of the points on the surface of the solution space and perform a maximization function by traversing the points having the maximum level of activity relative to other points in proximity. In some embodiments, the machine learning model may measure level of activity at some or all of the points on the surface of the solution space and perform a minimization function by traversing the points having the minimum level of activity relative to other proximate points.

In some embodiments, the machine learning model may be trained to perform a combination of minimization and maximization functions while performing the traversals.

The selection of the trial may be transmitted to the artificial intelligence engine 140. The artificial intelligence engine 140 may use the one or more machine learning models 132 to perform the selected trial using the solution space. At block 2204, the processing device of the computing device 102 may receive, from the artificial intelligence engine 140, one or more results of performing the trial. The one or more results may (i) provide a location of a point reached in the solution space after performing a traversal of the solution space defined by the trial, or (ii) provide a metric of one or more of the machine learning models 132 used by the artificial intelligence engine 140 to perform the trial. The metric may pertain to the process graphic processing unit (GPU) usage (%), the process GPU power usage (%), the process GPU memory allocated (%), the process GPU time spent accessing memory (%), and the process GPU temperature (degrees, e.g., Celsius) (as shown in FIG. 17). The one or more results may be presented on a user interface of the computing device 102. The one or more results may be compared to select the one or more machine learning models that reached or came closest to a desired point in the solution space, took a desired route (or as close to the desire route as possible) during traversal to the point, generated a desired sequence having desired activity levels, consumed the least or a lesser amount of processor resources, generated the lowest or a lower temperature for the graphic processing unit, consumed the least or a lesser amount of memory resources, or some combination thereof. The machine learning models not selected may be subsequently tuned to attempt to improve their results when subsequently performing the same or different trials.

Figure 23:
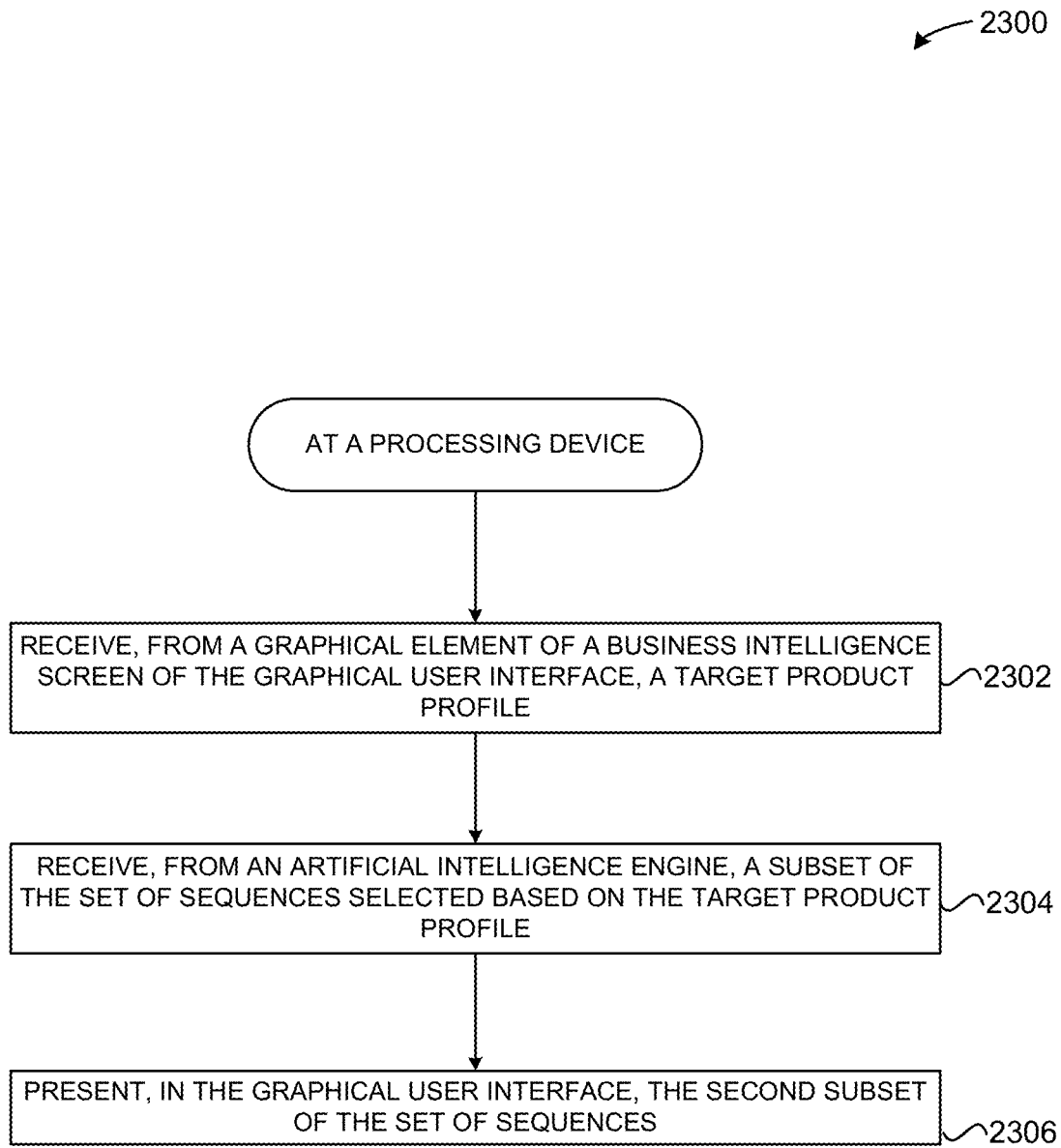
FIG. 23 illustrates example operations of a method for using a business intelligence screen to select a desired target product profile for sequences according to certain embodiments of this disclosure.

FIG. 23 illustrates example operations of a method 2300 for using a business intelligence screen to select a desired target product profile for sequences according to certain embodiments of this disclosure. Method 2300 includes operations performed by processors of a computing device (e.g., any component of FIG. 1, such as computing device 102, server 128 executing the artificial intelligence engine 140, etc.). In some embodiments, one or more operations of the method 2300 are implemented in computer instructions stored on a memory device and executed by a processing device. The method 2300 may be performed in the same or a similar manner as described above in regard to method 400. The operations of the method 2300 may be performed in some combination with any of the operations of any of the methods described herein.

At block 2302, the processing device may receive, from a graphical element of a business intelligence screen of the graphical user interface (GUI), a target product profile. The target product profile may include pharmacology data, pharmacokinetic data, activity data, manufacturing data (e.g., cost to manufacture, requirements for manufacturing, etc.), compliance data, clinical trial data, or some combination thereof. The target product profile may be transmitted to the artificial intelligence engine 140. The artificial intelligence engine 140 may execute one or more machine learning models 132 trained to generate or search for sequences that match the target product profile to within a certain threshold level (e.g., percentage, partial, exact, etc.).

At block 2304, the processing device may receive, from the artificial intelligence engine 140, a second subset of the set of sequences. The second subset of the set of sequences may be selected based on the target product profile.

At block 2306, the processing device may present, in the GUI, the second subset of the set of sequences. The GUI may include one or more graphical elements that enable the user to drill-down to view detailed data pertaining to one or more of the sequences matching (partially or exactly) the target product profile. The GUI may include a graphical element that enables selecting one or more sequences to manufacture, produce, synthesize, or the like.

Figure 24A:
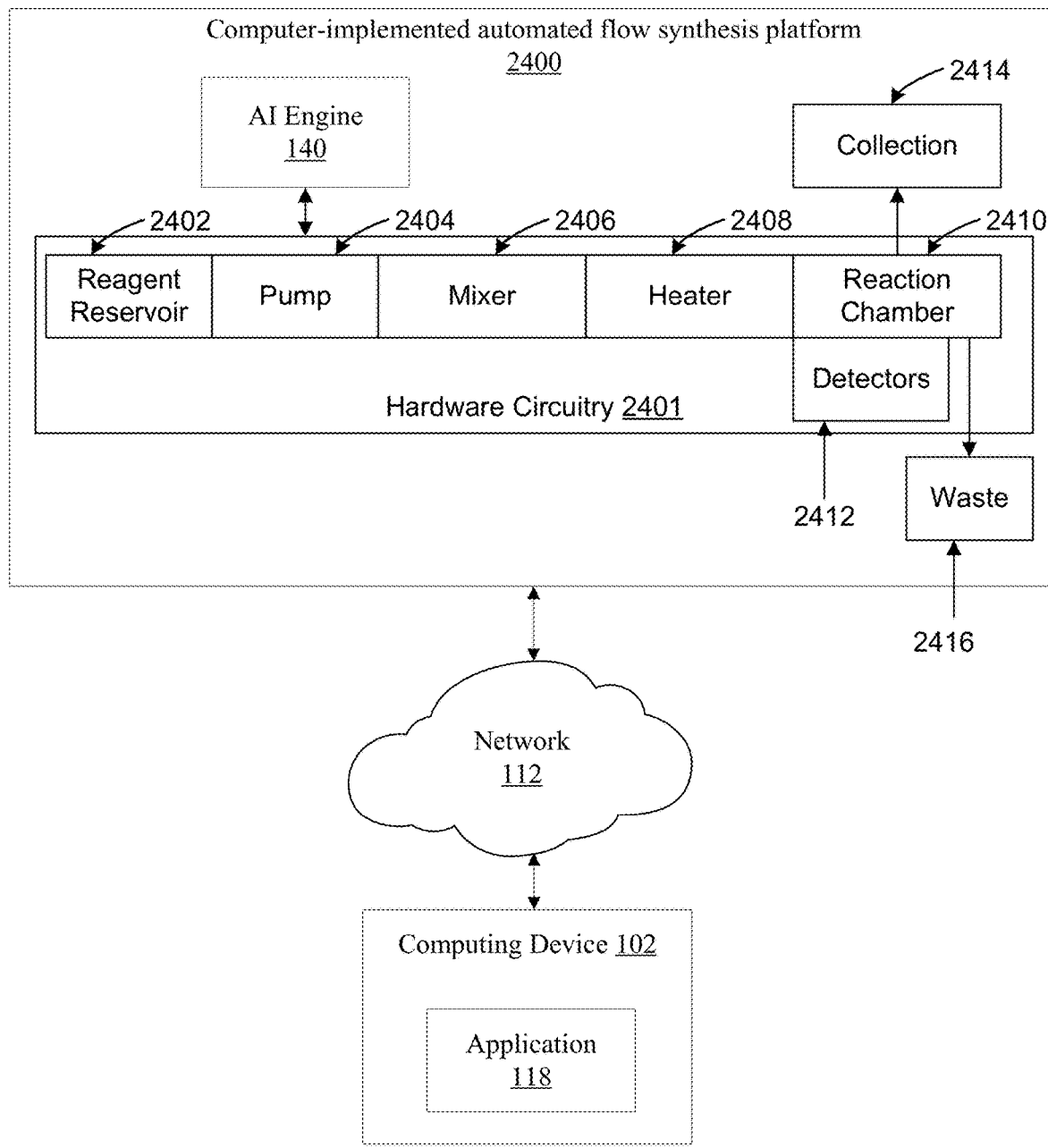
FIG. 24A illustrates another high-level component diagram of an illustrative system architecture according to certain embodiments of this disclosure.

FIG. 24A illustrates another high-level component diagram of an illustrative system architecture according to certain embodiments of this disclosure. As depicted, a computer-implemented automated flow synthesis platform (AFSP) 2400 is presented. The AF SP 2400 is communicatively coupled, via the network 112, to the computing device 102. The AF SP 2400 uses the artificial intelligence engine 140 as described herein. The AF SP 2400 includes various hardware components 2401, such as one or more reagent reservoirs 2402, pumps 2404, mixers 2406, heaters 2408, reaction chambers 2410, or detectors 2412. In some embodiments, the hardware components 2401 may each be communicatively coupled, via the network 112, to the cloud-based computing system 116 executing the artificial intelligence engine 140. In some embodiments, the hardware components 2401 may be communicatively coupled via a wired connection (e.g., Ethernet) to the server 128 executing the artificial intelligence engine 140.

The AFSP 2400 may use the hardware components 2401 to perform an automated flow process to synthesize candidate drug compounds (e.g., sequences representing proteins (peptides, peptidomimetics, etc.)) generated by the artificial intelligence engine 140. The artificial intelligence engine 140 may also generate a synthesizing recipe that includes one or more attributes of parameters. The one or more attributes of parameters may be used by the artificial intelligence engine 140 to control the hardware components performing the automated flow process on the sequence.

Figure 24B:
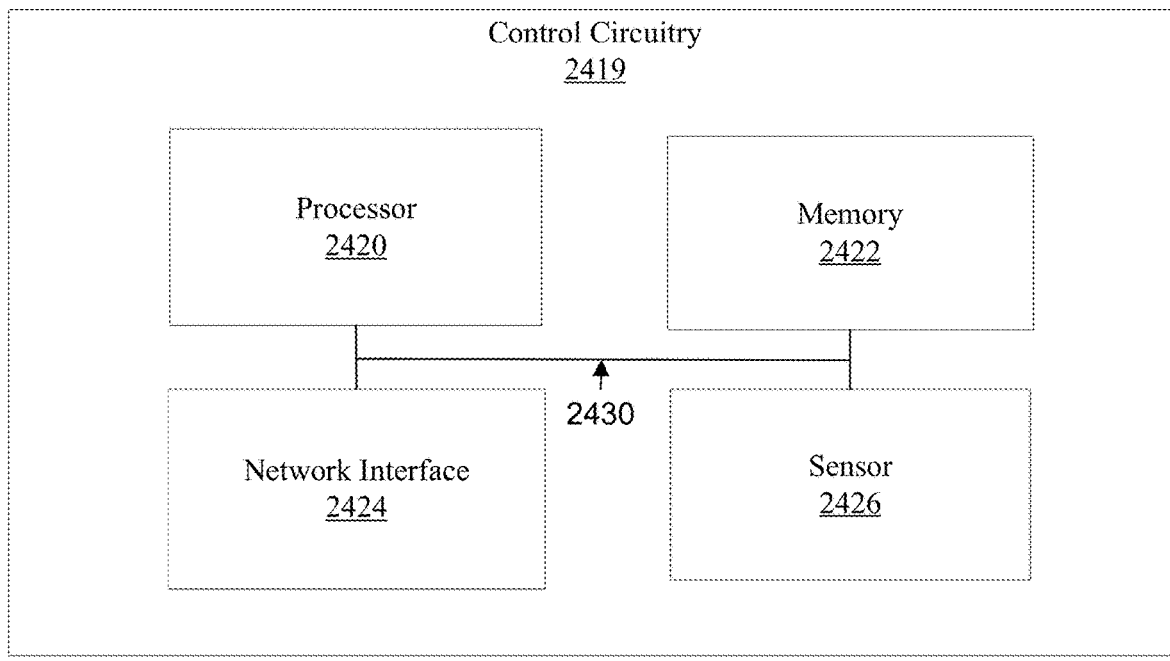
FIG. 24B illustrates a high-level component diagram of illustrative control circuitry according to certain embodiments of this disclosure.

Each of the hardware components 2401 may include respective control circuitry 2419, as depicted in FIG. 24B. The control circuitry 2419 for each of the hardware components 2401 may include all of the electronic components depicted in the control circuitry 2419, a subset of the electronic components depicted in the control circuitry 2419, or additional electronic components not depicted in the control circuitry 2419. The electronic components of the control circuitry 2419 may include a processor 2420, a memory 2422, a network interface 2424, or a sensor 2426, which communicate with each other via a bus 2430.

The processor 2420 represents one or more general-purpose processing devices such as microprocessors, central processing units, or the like. More particularly, the processing device 3002 may be a complex instruction set computing (CISC) microprocessor, reduced instruction set computing (RISC) microprocessor, very long instruction word (VLIW) microprocessor, quantum computer, or a processor implementing other instruction sets or processors implementing a combination of instruction sets. The processing device 3002 may also be one or more special-purpose processing devices such as an application specific integrated circuit (ASIC), a system on a chip, a field programmable gate array (FPGA), a digital signal processor (DSP), a network processor, or the like. The processing device 3002 may be configured to execute instructions for performing any of the operations and steps discussed herein.

The memory 2422 represents read-only memory (ROM), flash memory, solid state drives (SSDs), dynamic random access memory (DRAM) (such as synchronous DRAM (SDRAM)), a static memory 3006 (e.g., flash memory, solid state drives (SSDs), or static random access memory (SRAM)), or the like), or the like.

The network interface device 2424 may include circuitry configured to communicate data via wired or wireless protocols (e.g., via the network 120). In some embodiments, the network interface device 2424 may receive control signals including instructions from the cloud-based computing system 116 (e.g., artificial intelligence engine 140). The instructions may include the one or more attributes of parameters specified in the synthesizing recipes generated by the artificial intelligence engine 140. The network interface device 2424 may transmit the receive control signals to the processor 2420, and to modify the operating parameters of the respective hardware component 2401 associated with the control circuitry 2419, the processor 2420 may execute the instructions included in the controls signal. For example, the instructions may cause the heater 2408 to modify an attribute of a parameter related to a temperature setting, the instructions may cause the reagent reservoir 2402 to modify an attribute of a parameter related to how much of a particular solvent to dispense, etc.

The sensor 2426 may be any suitable sensor, such as those described with reference to the detectors 2412 herein. The measurements obtained by the sensors 2426 may be transmitted, via the network interface device 2424, to the cloud-based computing system 116 in real-time or near real-time as the measurements are received prior to, during, or after the automated flow process. In some embodiments, the real-time or near real-time transmission of measurements may enable the artificial intelligence engine 140, while the automated flow process of a sequence is being performed, to adjust the synthesizing parameters, such that the chemical reactions during synthesis are altered in a desirable manner.

In FIG. 24A, the reagent reservoir 2402 may include separate reservoirs for amino acids and peptide synthesis solvents and reagents. The amino acids and peptide synthesis solvents and reagents may be connected through a controllable valve coupled to the pump 2404. The attributes of parameters of the synthesizing recipe may determine which peptide synthesis solvents and reagents are selected for the automated flow process. The candidate drug compound (e.g., sequence) may determine which amino acids are selected for synthesis via the automated flow process. The pump 2404 may provide a mechanism (e.g., pressurized source of helium or other inert gas) for transferring the amino acids, reagents, and solvents to the mixer 2406. The mixer 2406 may be a static mixer and may provide continuous mixing of fluid materials, gas streams, or the like. The mixer 2406 may mix the amino acids and peptide synthesis solvents and reagents, which are transferred to the heater 2408. The heater 2408 may preheat the mixed amino acids and peptide synthesis solvents and reagents for injection into the reaction chamber 2410. The temperature of the heater 2408 may be set by the attributes of parameters of the synthesizing recipe. To synthesize the sequence, the amino acids and peptide synthesis solvents and reagents may be sequentially transferred into the reaction chamber 2410 in a continuous flow.

During the automated flow process, the detectors 2412 may monitor in real-time or near real-time reaction points (e.g., amide couplings) in the reaction chamber 2410. The detectors 2412 may include various spectral devices, such as an ultra violet (UV)-vis spectrometer, a fluorescence spectrometer, a calorimeter (e.g., heat flow measurement of a chemical reaction or physical change), an infrared spectrometer, a flow cytometry protein interaction assay (FCPIA), a circular dichroism (CD) spectrophotometer (e.g., ultraviolet, visible, and infrared radiation, an electromagnetic spectrometer (e.g., x-ray, ultraviolet, visible, infrared, or microwave wavelengths, a nuclear magnetic resonance (NMR) spectrometer, a high-performance liquid chromatographer (HPLC), etc. configured to obtain measurements to include in a spectral profile describing the characteristics of the chemical reaction at the particular reaction point (e.g., amide coupling). The detectors 2412 may also include a thermal detector configured to measure the temperature within the reaction chamber.

The measurements obtained may include a spectral profile of each chemical reaction that occurs at each reaction point. To train one or more machine learning models 132, the measurements may be transmitted to the artificial intelligence engine 140. The machine learning models 132 may associate the spectral profile for the chemical reaction that occurs at each amide coupling, and further may associate the synthesizing recipe that resulted in the chemical reaction at the amide coupling during synthesis of the sequence. For example, the characteristics of the chemical reaction may indicate an undesired side reaction occurred at the reaction point. The machine learning model 132 may be trained to generate sequences or synthesizing recipes that do not result in the side reactions during subsequently performed automated flow processes.

In some embodiments, after the amide couplings are complete, a deprotection step may be performed and the detectors 2412 may monitor the deprotection step and transmit data pertaining to the deprotection step to the artificial intelligence engine 140. Further, the detectors 2412 may monitor purification and post-purification of the synthesized sequence. A collection 2414 portion of AFSP 2400 may store the synthesized sequence that is cleaved from a resin and a waste 2416 portion may store any byproducts or waste materials discarded during purification or cleavage of the synthesized sequence.

Figure 25:
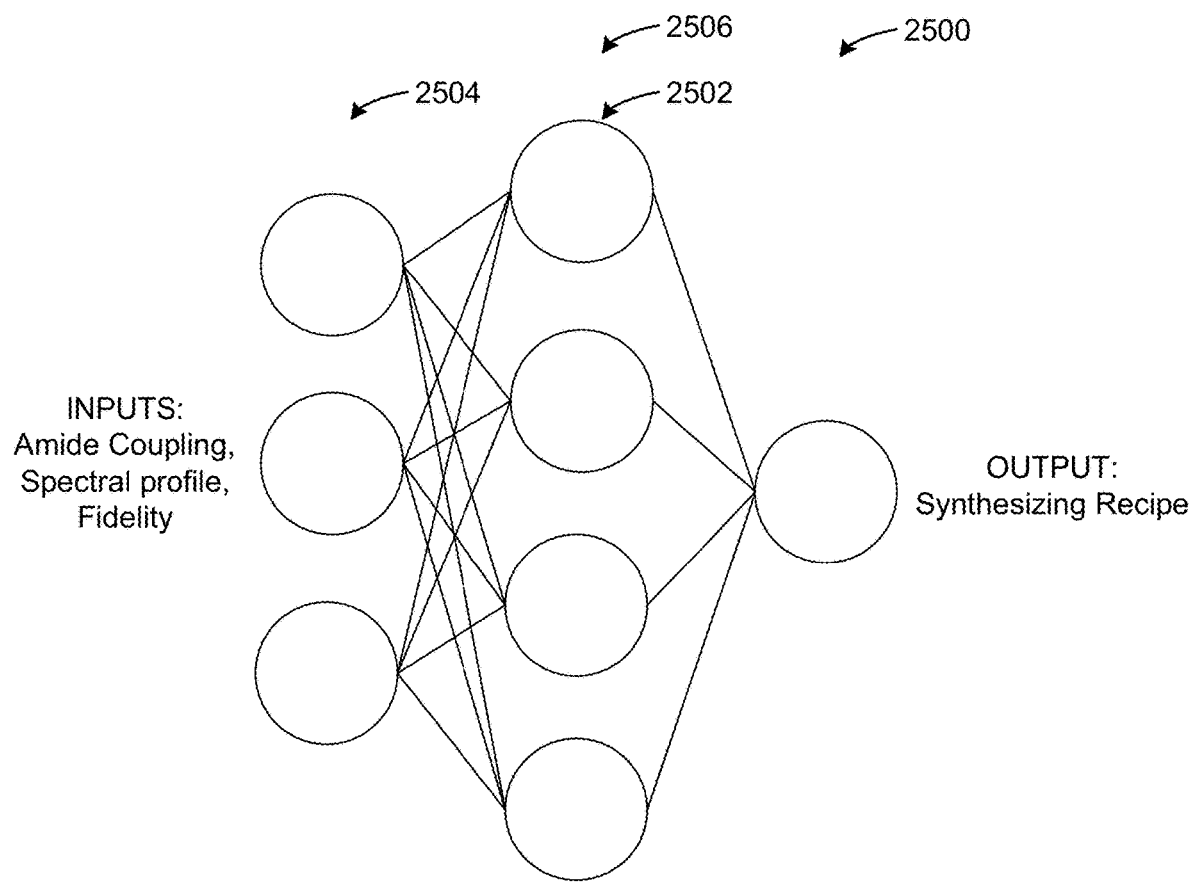
FIG. 25 illustrates an example neural network for determining a synthesizing recipe for canonical or non-canonical amino acids according to certain embodiments of this disclosure.

FIG. 25 illustrates an example neural network 2500 (e.g., machine learning model 132) for determining a synthesizing recipe for canonical or non-canonical amino acids according to certain embodiments of this disclosure. The neural network 2500 may be any suitable neural network as described herein, such as generative adversarial networks, convolutional neural networks, recurrent neural networks with one or more hidden layers, and fully connected neural networks (e.g., each neuron may transmit its output signal to the input of the remaining neurons, as well as to itself). For example, the neural network 2500 may include numerous layers or hidden layers that perform calculations (e.g., dot products) using various neurons. The neural network 2500 includes three layers of nodes 2502 and each of the nodes 2502 may be assigned a respective weight that is configurable based on an importance of an output being determined by the respective node 2502.

The depicted neural network 2500 may be trained, using training data, to match patterns between inputs and outputs. For example, the training data may include input data representing various amide couplings between two amino acids, the spectral profiles associated with the amide couplings, or fidelity data associated with the amide couplings. The spectral profiles may represent a signature of the amide coupling and the fidelity data may provide indications of a characteristic of the amide coupling (e.g., strong coupling, weak coupling, successful coupling, unsuccessful coupling, etc.). The training data may also include output data mapped to the input data, where the output data includes the synthesizing recipes that produce the associated amide coupling, spectral profile, and fidelity data during an automated flow process. Such a technique may be particularly beneficial for non-canonical amino acids where the chemical reactions during amide couplings are more difficult to predict than for canonical amino acids. However, the disclosed techniques may enable generating optimized synthesizing recipes for canonical amino acids, as well.

In some embodiments, the neural network 250 may include a first layer 2504 that may include first nodes trained to receive, as first input, an amide coupling of the sequence, a fidelity of the amide coupling, and the spectral profile, and the first nodes may generate, as an output, at least a subset of the one or more attributes of parameters used during the automated flow process to synthesize the sequence. In some embodiments, the neural network 2500 may include a second layer 2506, where said second layer 2506 may include second nodes trained to receive, as input, the output of the first nodes, and a set of amide couplings. The second nodes may be trained to generate, as a second output, at least another subset of the one or more attributes of parameters used during the automated flow process to synthesize the sequence, and the synthesizing recipe may include the first subset and the second subset of the one or more attributes of parameters. In some embodiments, the first nodes may be a first machine learning model and the second nodes may be a second machine learning model, and the output of the first machine learning model may be input to the second machine learning model. Such techniques may enhance processing time by dividing workload between different machine learning models.

Figure 26A:
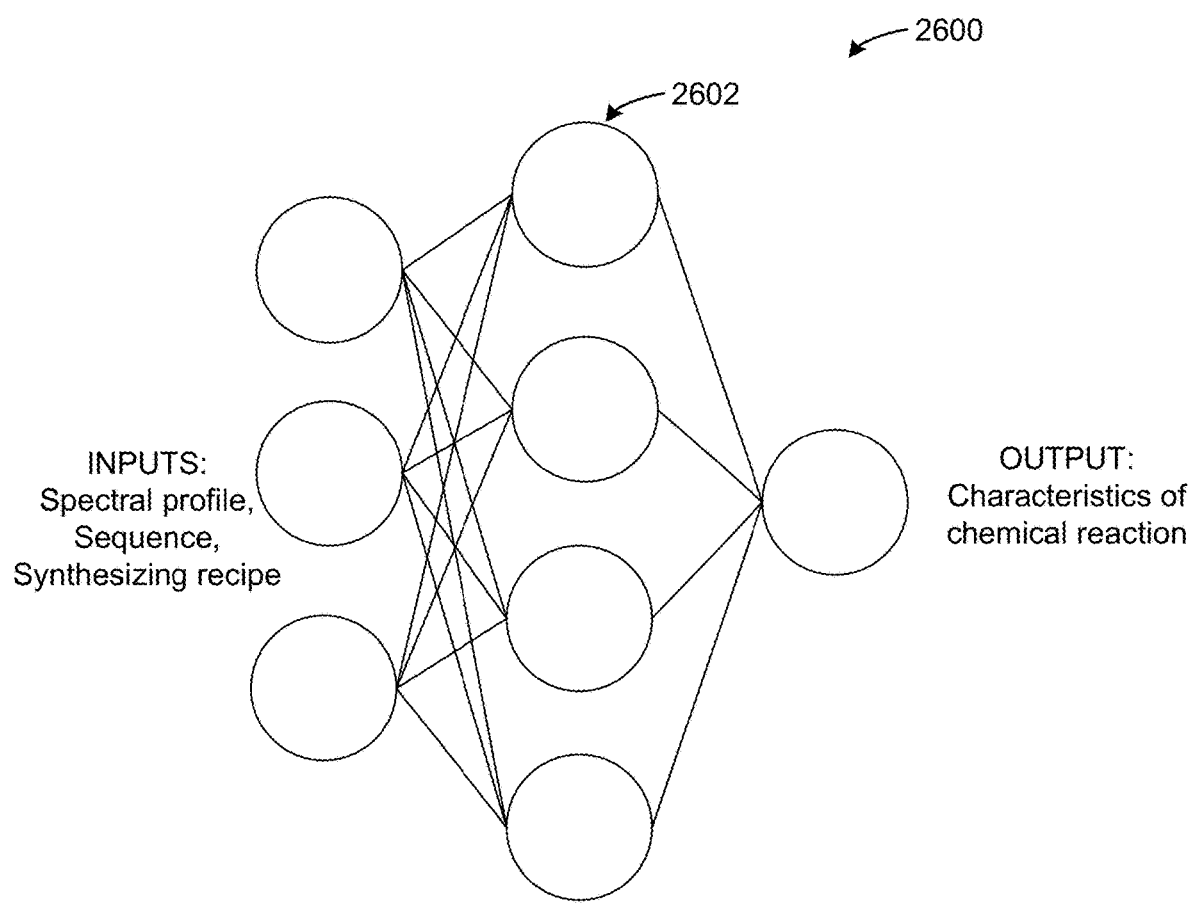
FIG. 26A illustrates an example neural network for determining characteristics of a chemical reaction according to certain embodiments of this disclosure.

FIG. 26A illustrates an example neural network 2600 for determining characteristics of a chemical reaction according to certain embodiments of this disclosure. The neural network 2600 includes three layers of nodes 2602 and each of the nodes 2602 may be assigned a respective weight, wherein the weight is determined by or derived or computed based on the relative importance of an output being determined by the respective node 2602 (as opposed to the output being determined by a different node or nodes). An output may consist of a determination of a received value or computed value (e.g., expected value, probabilistic value, stochastic value, predicted value, unmodified value, non-computed value, etc.) that is modified by the weight based on the relative importance. Any suitable number of layers of nodes 2602 may be used. The depicted neural network 2600 may be trained, using training data, to match patterns between inputs and outputs. For example, the training data may include input data representing various spectral profiles, sequences of amino acids, and synthetizing recipes for controlling the automated flow process. The training data may include output data mapped to the input data, where the output data includes characteristics of chemical reactions associated with the spectral profiles, the sequences, and the synthesizing recipes. In some embodiments, the characteristics of the chemical reactions may indicate undesirable side reactions (e.g., aggregation). Thus, the artificial intelligence engine 140 may use the trained neural network 2600 to determine which characteristics of chemical reactions may occur if certain sequences, synthesizing recipes, or spectral profiles are present. The artificial intelligence engine 140 may use the trained neural network 2600 to run simulations to identify combinations of sequences or synthesizing recipes that do not result in any undesired side reactions. The identified sequences or synthesizing recipes may be used by the AFSP 2400 to implement an automated flow process.

Figure 26B:
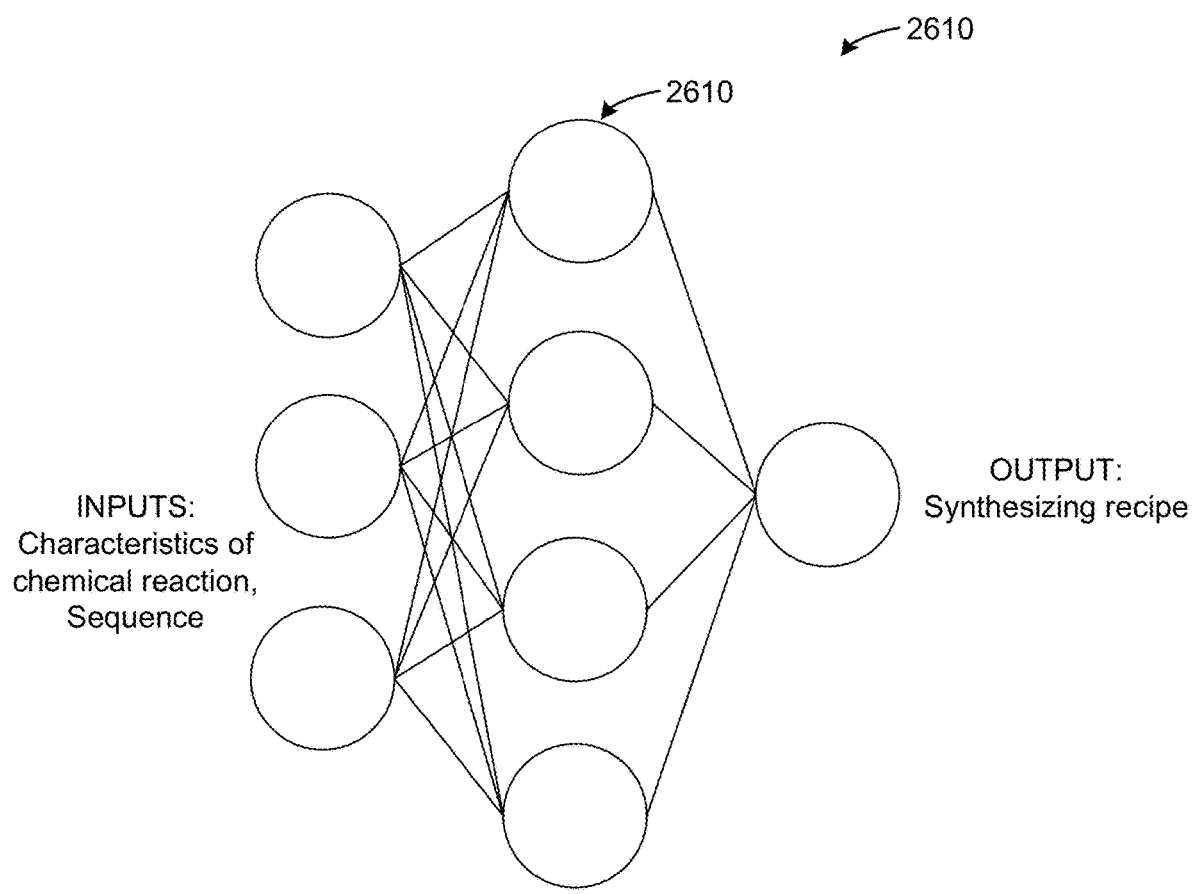
FIG. 26B illustrates an example neural network for determining, based on characteristics of a chemical reaction, a synthesizing recipe, according to certain embodiments of this disclosure.

FIG. 26B illustrates an example neural network 2610 for determining, based on characteristics of a chemical reaction, a synthesizing recipe according to certain embodiments of this disclosure. The neural network 2610 is similar to the neural network 2600 of FIG. 26A except that the neural network 2610 is trained in an opposite manner. That is, the neural network 2610 is trained to receive input data comprising sequences and characteristics of chemical reactions, and to output corresponding synthesizing recipes that produce the characteristics of the chemical reactions for the sequences. Such techniques may enable the artificial intelligence engine 140 to use the trained neural network 2610 to run simulations. The simulations may iteratively select a desired chemical reaction or sequence and the trained neural network 2610 may generate output, wherein such output may include the synthesizing recipe to implement.

Figure 27:
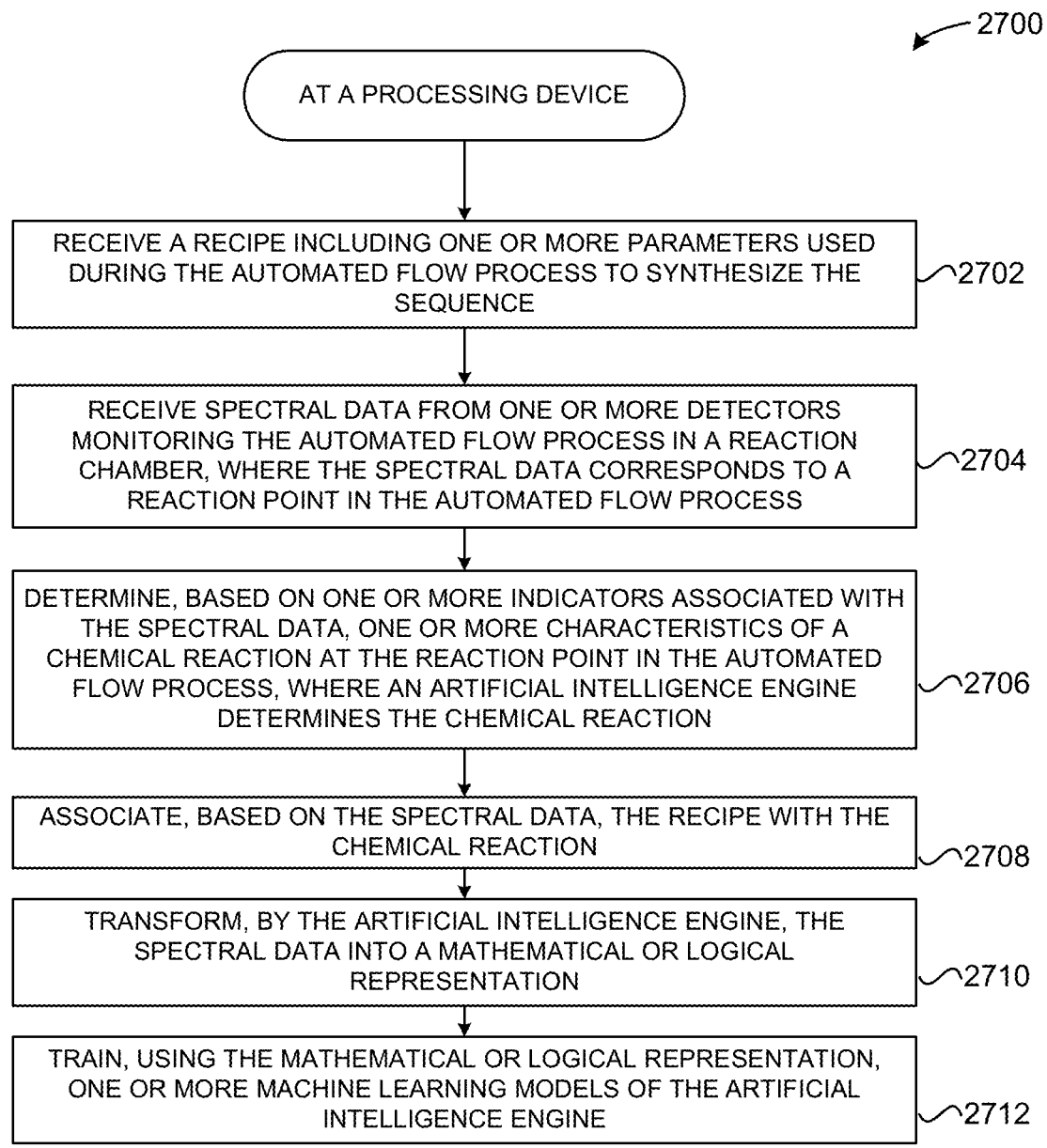
FIG. 27 illustrates example operations of a method for an artificial-intelligence-enabled automated flow synthesis platform configured to generate optimized synthesizing recipes which enable a sequence to be synthesized using an automated flow process, according to certain embodiments of this disclosure.

FIG. 27 illustrates example operations of a method 2700 for an artificial-intelligence enabled automated flow synthesis platform configured to generate optimized synthesizing recipes which enable a sequence to be synthesized using an automated flow process according to certain embodiments of this disclosure. Method 2700 includes operations performed by processors of a computing device (e.g., any component of FIG. 1 or FIG. 24, such as computing device 102, server 128 executing the artificial intelligence engine 140, etc.). In some embodiments, one or more operations of the method 2700 are implemented in computer instructions stored on a memory device and executed by a processing device. The method 2700 may be performed in the same or a similar manner as described above in regard to method 400. The operations of the method 2700 may be performed in some combination with any of the operations of any of the methods described herein.

The method 2700 may pertain to the computer-implemented automated flow synthesis platform (AFSP) 2400 configured to generate optimized synthesizing recipes that may enable a sequence to be synthesized using an automated flow process. In some embodiments, the sequence may be generated by the AI engine 140 as described further herein. The sequence may be a peptide sequence or a peptidomimetic sequence. The AI engine 140 may generate the sequence based on a desired activity level in a therapeutic domain (e.g., anti-infective, anti-cancer, antimicrobial, antiviral, anti-fungal, anti-inflammatory, anti-cholinergic, anti-dopaminergic, anti-serotonergic, anti-noradrenergic, anti-prionic, anti-fungal functional biomaterials (e.g., adhesives, sealants, binders, chelates, diagnostic reporters, or some combination thereof), and structural biomaterials (e.g., biopolymers, encapsulation films, flocculants, desiccants, or some combination thereof), etc.). At block 2702, the processing device may receive a synthesizing recipe, wherein the synthesizing recipe may include one or more attributes of parameters used during an automated flow process to synthesize the sequence. In automated flow processes, two or more reagents are mixed in a continual or continuous manner through the reaction chamber 2410 with flow, temperature, or pressure controlled such that the desired chemical reaction can take place most efficiently. Accordingly, in some embodiments, the one or more attributes of parameters may include one or more temperatures, solvents, protection groups, resin anchors, pressures, or some combination thereof. For example, certain of the attributes of parameters may indicate or specify how to control operation of the reagent reservoir 2402, the pump 2404, the mixer 2406, the heater 2408, or the reaction chamber 2410.

At block 2704, the processing device may receive spectral data from one or more detectors 2412 monitoring the automated flow process in a reaction chamber. The spectral data may correspond to a reaction point in the automated flow process. The spectral data may include ultraviolet light, infrared light, ultraviolet rays, infrared radiation, thermal radiation, thermal light, fluorescent light, visible light, or some combination thereof. The spectral data may include information pertaining to one or more quality control measurements of the sequence configured to be synthesized using the automated flow process, and the one or more quality control measurements may include structural information of the sequence, functional information of the sequence, or some combination thereof. In some embodiments, the automated flow synthesis may include bonding one or more amino acids of the sequence to a resin anchor. The resin anchor may include at least two linkers, and each of the two linkers may be configured to bond with a different respective type of amino acid.

In some embodiments, the artificial intelligence engine 140 may transform the spectral data into a mathematical or logical representation. The artificial intelligence engine 140 may use the mathematical or logical representation to train the one or more machine learning models 132. The mathematical or logical representation may be a vector or eigenvector. The artificial intelligence engine 140 may encode the spectral data in the eigenvector at a lower dimension than the received spectral data, and the lower-dimensional eigenvector representing the spectral data may be input into machine learning model trained to process lower-dimensional encodings. Such techniques may reduce computing resources and provide a technical solution to processing spectral data to determine characteristics of chemical reactions, desired sequences, or desired synthesizing recipes.

At block 2706, the processing device may determine, based on one or more indicators associated with the spectral data, one or more characteristics of a chemical reaction at the reaction point in the automated flow process. The reaction point may be associated with an amide coupling of an amino acid at a terminus of another amino acid currently bonded in a polypeptide within the reaction chamber 2410. The artificial intelligence engine 140 may determine characteristics of the chemical reaction. For example, the characteristics of the chemical reaction may indicate that one or more side reactions have occurred. The side reactions may be undesirable and the artificial intelligence engine 140 may train one or more machine learning models 132 to output sequences or synthesizing recipes not associated with the side reactions represented by the spectral data. As such, optimized sequences or synthesized recipes may be produced that enable more efficient discovery of unique sequences that exhibit desired biochemical properties in certain therapeutic domains. Also, the disclosed techniques may enable economic benefits by reducing the amount of reagents used, as well as reducing the synthesis time, thereby reducing wear and tear on the hardware used to synthesize the sequence.

At block 2708, the processing device may control, using the synthesizing recipe, the synthesis of a sequence in the reaction chamber 2410. In some embodiments, the sequence may include an amino acid, wherein the amino acid may be canonical or non-canonical.

In some embodiments, the processing device may receive second spectral data from the one or more detectors 2412 monitoring the automated flow process in the reaction chamber 2410. The second spectral data may correspond to a second reaction point in the automated flow process. In some embodiments, the processing device may determine, based on one or more indicators associated with the second spectral data, one or more second characteristics of a second chemical reaction at the second reaction point in the automated flow process. The artificial intelligence engine 140 may determine the second chemical reaction. In some embodiments, the processing device may, based on the second spectral data, associate the synthesizing recipe with the second chemical reaction. In some embodiments, the processing device may, based on the second spectral data, associate the synthesizing recipe with the second chemical reaction.

In some embodiments, the processing device may determine, based on the correlation between the synthesizing recipe and the chemical reaction, a subsequent recipe to implement in the automated flow process of the sequence. The artificial intelligence engine 140 may determine the subsequent synthesizing recipe. In some embodiments, the processing device may implement the subsequent synthesizing recipe in the automated flow process.

Figure 28:
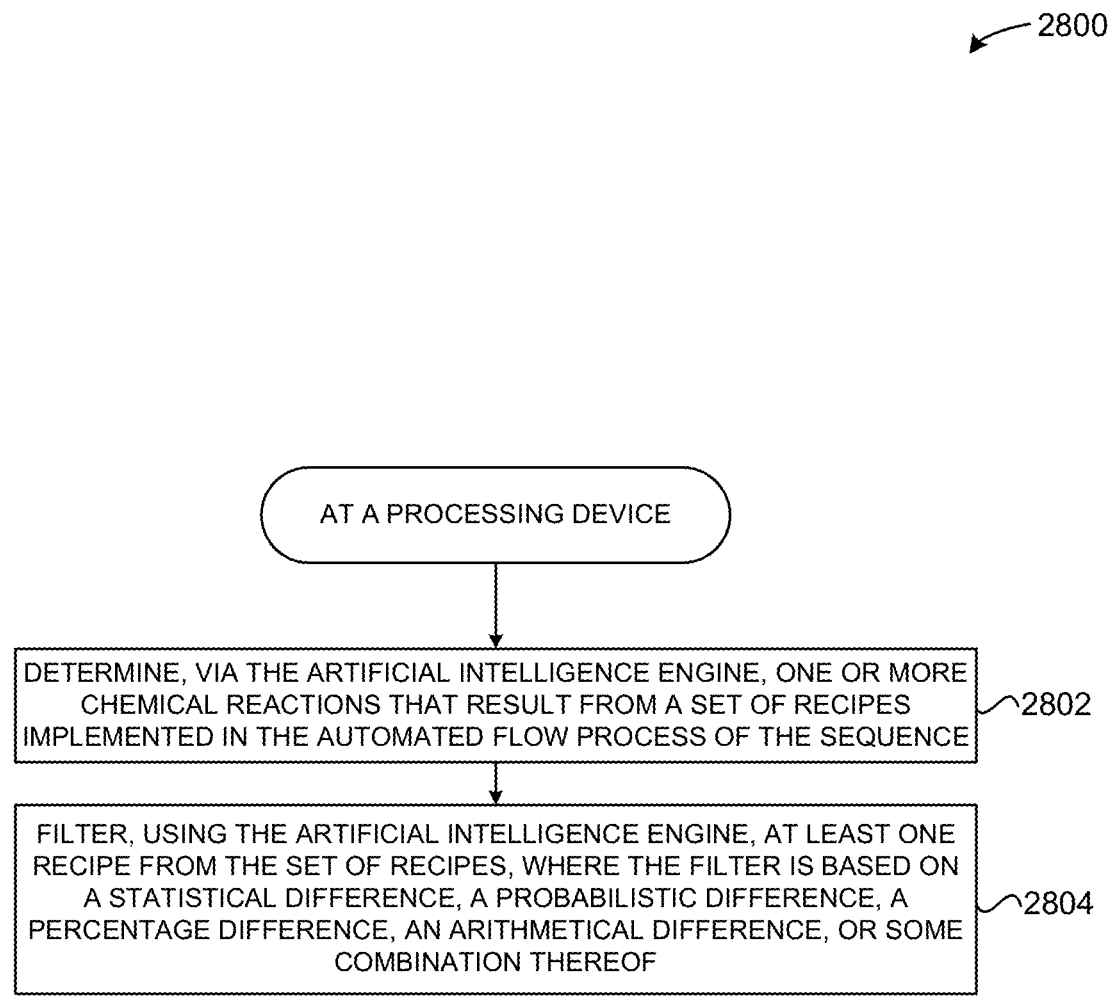
FIG. 28 illustrates example operations of a method for filtering recipes based on a statistical difference, a percentage difference, an arithmetical difference, or some combination thereof, according to certain embodiments of this disclosure.

FIG. 28 illustrates example operations of a method 2800 for filtering recipes based on a statistical difference, a percentage difference, an arithmetical difference, or some combination thereof according to certain embodiments of this disclosure. Method 2800 includes operations performed by processors of a computing device (e.g., any component of FIG. 1 or FIG. 24, such as computing device 102, server 128 executing the artificial intelligence engine 140, etc.). In some embodiments, one or more operations of the method 2800 are implemented in computer instructions stored on a memory device and executed by a processing device. The method 2800 may be performed in the same or a similar manner as described above in regard to method 400. The operations of the method 2800 may be performed in some combination with any of the operations of any of the methods described herein.

At block 2802, the processing device may determine, via the artificial intelligence engine 140, one or more characteristics of chemical reactions that result from a set of synthesizing recipes being implemented in automated flow processes of the sequence. At block 2804, the processing device may use the artificial intelligence engine 140 to filter the set of synthesizing recipes, where the filtering is based on a statistical difference, a probabilistic difference, a percentage difference, an arithmetical difference, or some combination thereof. For example, if two synthesizing recipes applied to a sequence result in characteristics of a chemical reaction that are statistically insignificant (e.g., less than 10% difference), then one of the synthesizing recipes may be filtered out from the set of synthesizing recipes. Such a technique may reduce the number of synthesizing recipes from which the machine learning models can generate or choose from, thereby increasing the speed at which the machine learning model operates. Also, reducing the number of possible synthesizing recipes that can be selected or generated may reduce processing resources (e.g., computing cycles) when the machine learning model is able to make a synthesizing recipe determination more quickly.

Figure 29:
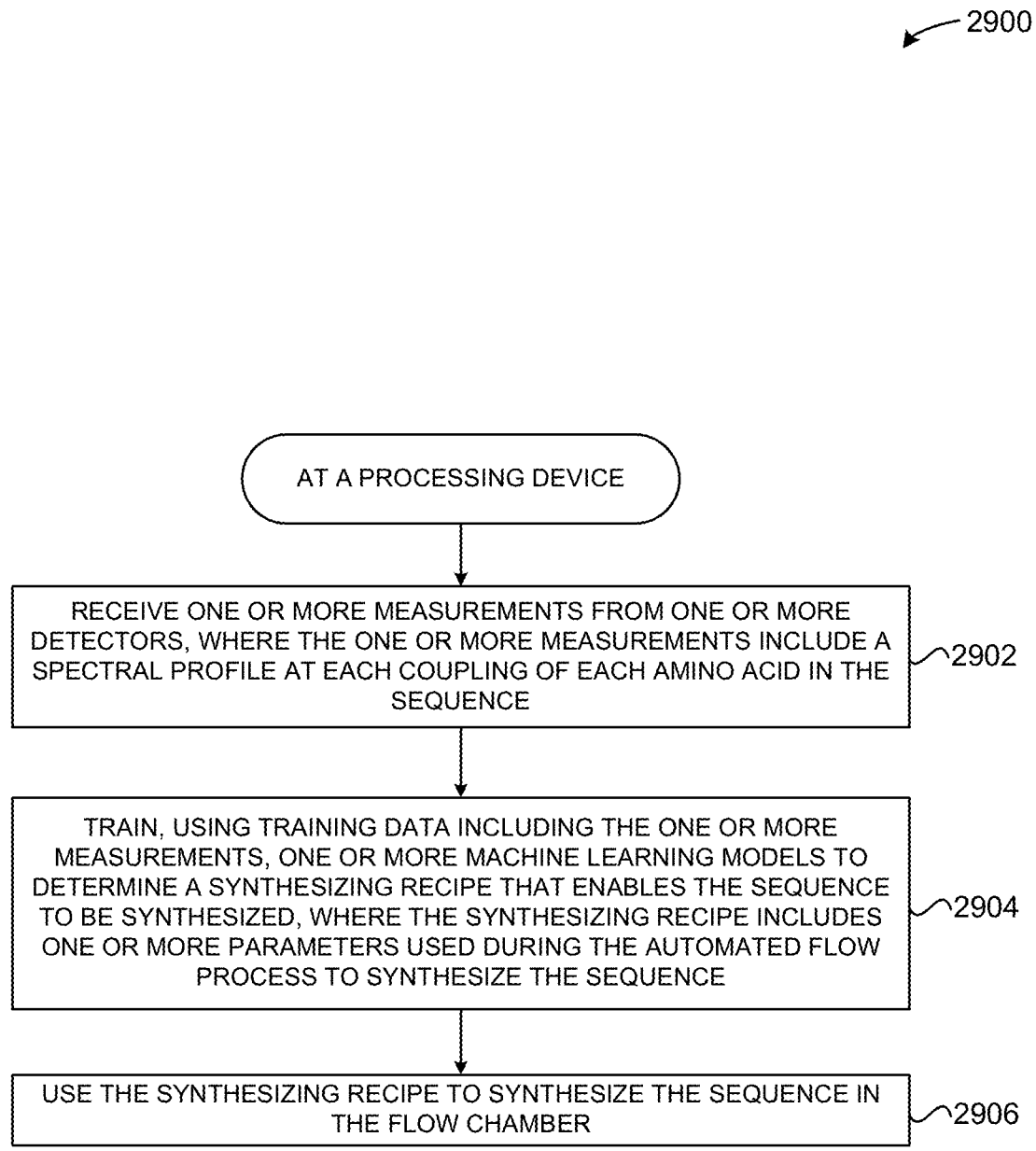
FIG. 29 illustrates example operations of a method for a computer-implemented automated flow synthesis platform for training machine learning models using spectral profiles of couplings of amino acids in a polypeptide, according to certain embodiments of this disclosure.

FIG. 29 illustrates example operations of a method 2900 for a computer-implemented automated flow synthesis platform for training machine learning models using spectral profiles of couplings of amino acids in a polypeptide according to certain embodiments of this disclosure. Method 2900 includes operations performed by processors of a computing device (e.g., any component of FIG. 1 or FIG. 24, such as computing device 102, server 128 executing the artificial intelligence engine 140, etc.). In some embodiments, one or more operations of the method 2900 are implemented in computer instructions stored on a memory device and executed by a processing device. The method 2900 may be performed in the same or a similar manner as described above in regard to method 400. The operations of the method 2900 may be performed in some combination with any of the operations of any of the methods described herein.

Method 2900 may be performed using the processing device communicatively coupled to the one or more detectors 2412 monitoring in the reaction chamber 2410 the synthesis of a sequence. The synthesis may use an automated flow process. The sequence may include one or more amino acids that are canonical or non-canonical. In some embodiments, the sequence may be a protein, and the protein may be a peptide or a peptidomimetic. As described further herein, the sequence may be generated using one or more machine learning models 132 based on a desired drug activity level in a therapeutic domain. At block 2902, the processing device may receive one or more measurements from one or more detectors 2412. The one or more measurements may include a spectral profile at each coupling of each amino acid in the sequence in the reaction chamber 2410. In some embodiments, the spectral profile may include ultraviolet light, infrared light, ultraviolet rays, infrared radiation, thermal radiation, thermal light, fluorescent light, visible light, or some combination thereof.

In some embodiments, the detectors may obtain measurements in real-time or near real-time as the amino acids couple in the reaction chamber 2410 and the measurements (spectral data) may be transmitted to the artificial intelligence engine 140 to enable retraining of the machine learning models 132. For example, the spectral profile of a particular amide coupling may indicate characteristics of an undesirable side reaction. Accordingly, the machine learning models 132 may be retrained to determine that the sequence being synthesized according to the synthesizing recipe results in an undesirable side reaction at that amide coupling. In subsequent iterations, by generating a new synthesizing recipe for the sequence or selecting a different sequence for the synthesizing recipe, the machine learning models 132 may avoid the undesirable side reaction. Further, the detectors 2412 may obtain data during the deprotection step to determine if any side reactions occur during the automated flow process that uses the synthesizing recipe.

At block 2904, to determine a synthesizing recipe that enables the sequence to be synthesized, the processing device may train, using training data including the one or more measurements, one or more machine learning models 132. The synthesizing recipe may include one or more attributes of parameters used during the automated flow process to synthesize the sequence. The one or more attributes of parameters may, inter alia, include one or more temperatures, solvents, protection groups, resin linkers or anchors, or some combination thereof The training data may include one or more inputs associated with one or more outputs, where the one or more inputs comprise an amide coupling, a spectral profile for a chemical reaction associated with the amide coupling, a fidelity of the amide coupling, or some combination thereof. In some embodiments, the fidelity of the coupling may comprise one of a first indication that an expected chemical reaction occurred at the coupling or a second indication that an unexpected chemical reaction (e.g., a side reaction) occurred at the coupling.

In some embodiments, the one or more machine learning models 132 may include a first layer including at least a first machine learning model 132, where the first machine learning model 132 receives, as a first input, an amide coupling of the sequence, a fidelity of the amide coupling, and the spectral profile, and the first machine learning model 132 generates, as an output, at least a subset of the one or more attributes of parameters used during the automated flow process to synthesize the sequence. The one or more machine learning models 132 may include a second layer including at least a second machine learning model 132, where the second machine learning model 132 receives, as input, the output of the first machine learning model 132, and a set of amide couplings. The second machine learning model 132 may generate, as a second output, at least another subset of the one or more attributes of parameters used during the automated flow process to synthesize the sequence, and the synthesizing recipe may include the first subset and the second subset of the one or more attributes of parameters. In some embodiments, the sequence may be a peptide chain sequence, wherein the peptide chain sequence may include the amide coupling and the set of amide couplings.

At block 2906, the processing device may control, using the synthesizing recipe, the synthesis of the sequence in the reaction chamber 2410. For example, during an automated flow process used to synthesize the sequence, the one or more attributes of parameters may indicate or specify how to control operation of various hardware components (e.g., reagent reservoir 2402, pump 2404, mixer 2406, heater 2408, reaction chamber 2410, detectors 2412, etc.) of the computer-implemented automated flow synthesis platform (AF SP) 2400.

Figure 30:
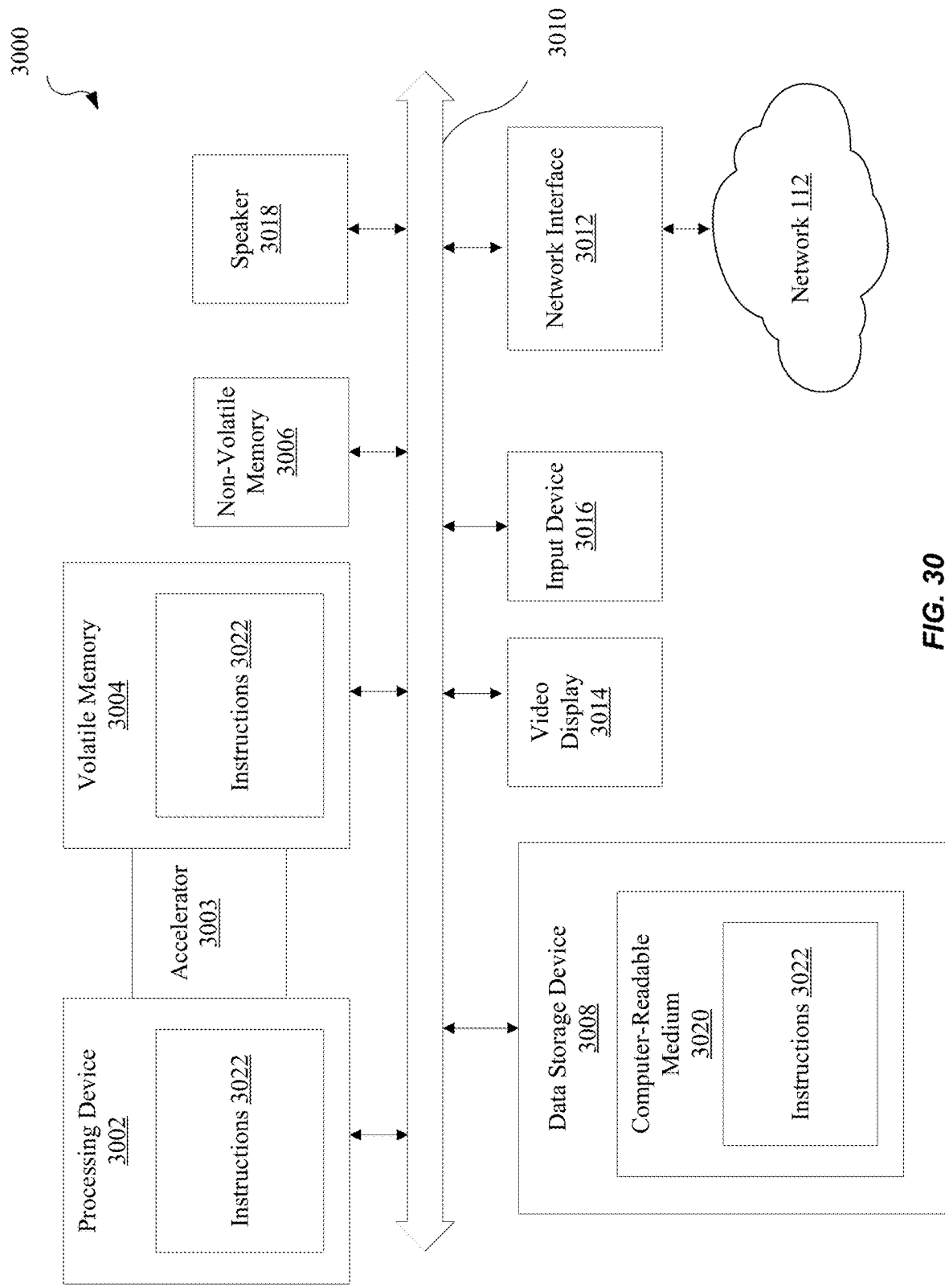
FIG. 30 illustrates an example computer system according to certain embodiments of this disclosure.

FIG. 30 illustrates example computer system 3000 which can perform any one or more of the methods described herein, in accordance with one or more aspects of the present disclosure. In one example, computer system 3000 may correspond to the computing device 102 (e.g., user computing device), one or more servers 128 of the computing system 116, the training engine 130, or any suitable component of FIG. 1. The computer system 3000 may correspond to any component of FIG. 24, such as the computer-implemented automated flow synthesis platform 2400 (e.g., any of the hardware components 2401). The computer system 3000 may be capable of executing application 118 or the one or more machine learning models 132 of FIG. 1. The computer system may be connected (e.g., networked) to other computer systems in a LAN, an intranet, an extranet, or the Internet. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 3000 includes a processing device 3002, a volatile memory 3004 (e.g., random access memory (RAM)), a non-volatile memory 3006 (e.g., read-only memory (ROM), flash memory, solid state drives (SSDs), and a data storage device 3008, the foregoing of which are enabled to communicate with each other via a bus 3010.

Processing device 3002 represents one or more general-purpose processing devices such as a microprocessor, central processing unit, or the like. More particularly, the processing device 3002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 3002 may also be one or more special-purpose processing devices such as an application specific integrated circuit (ASIC), a system on a chip, a field programmable gate array (FPGA), a digital signal processor (DSP), network processor, or the like. The processing device 3002 may include more than one processing device, and each of the processing devices may be the same or different types. The processing device 3002 may include or be communicatively coupled to one or more accelerators 3003 configured to offload various data-processing tasks from the processing device 3002. The processing device 3002 is configured to execute instructions for performing any of the operations and steps discussed herein.

The computer system 3000 may further include a network interface device 3012. The network interface device 3012 may be configured to communicate data via any suitable communication protocol. In some embodiments, the network interface devices 3012 may enable wireless (e.g., WiFi, Bluetooth, ZigBee, etc.) or wired (e.g., Ethernet, etc.) communications. The computer system 3000 also may include a video display 3014 (e.g., a liquid crystal display (LCD), a light-emitting diode (LED), an organic light-emitting diode (OLED), a quantum LED, a cathode ray tube (CRT), a shadow mask CRT, an aperture grille CRT, or a monochrome CRT), one or more input devices 3016 (e.g., a keyboard or a mouse), and one or more speakers 3018 (e.g., a speaker). In one illustrative example, the video display 3014 and the input device(s) 3016 may be combined into a single component or device (e.g., an LCD touch screen).

The data storage device 3016 may include a computer-readable medium 3020 on which the instructions 3022 embodying any one or more of the methods, operations, or functions described herein is stored. The instructions 3022 may also reside, completely or at least partially, within the volatile memory 3004 or within the processing device 3002 during execution thereof by the computer system 3000. As such, the volatile memory 3004 and the processing device 3002 also constitute computer-readable media. The instructions 3022 may further be transmitted or received over a network via the network interface device 3012.

While the computer-readable storage medium 3020 is shown in the illustrative examples to be a single medium, the term "computer-readable storage medium" should be taken to include a single medium or multiple media (e.g., a centralized or distributed database, or associated caches and servers) that store the one or more sets of instructions. The term "computer-readable storage medium" shall also be taken to include any medium capable of storing, encoding, or carrying a set of instructions for execution by the machine, where such set of instructions cause the machine to perform any one or more of the methodologies of the present disclosure. The term "computer-readable storage medium" shall accordingly be taken to include, but not be limited to, solid-state memories, optical media, and magnetic media.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

Consistent with the above disclosure, the examples of systems and method enumerated in the following clauses are specifically contemplated and are intended as a non-limiting set of examples.

Clause 1. A method wherein an artificial intelligence (AI) enabled automated flow synthesis platform is configured to generate optimized synthesizing recipes which enable a sequence to be synthesized using an automated flow process, the method comprising:

receiving a synthesizing recipe comprising one or more attributes of parameters used during the automated flow process to synthesize the sequence;

receiving spectral data from one or more detectors monitoring the automated flow process in a reaction chamber, wherein the spectral data corresponds to a reaction point in the automated flow process;

determining, based on one or more indicators associated with the spectral data, one or more characteristics of a chemical reaction at the reaction point in the automated flow process, wherein an artificial intelligence engine determines the chemical reaction; and associating, based on the spectral data, the synthesizing recipe with the chemical reaction.

Clause 2. The method of any clause herein, further comprising:

receiving second spectral data from the one or more detectors monitoring the automated flow process in the reaction chamber, wherein the second spectral data corresponds to a second reaction point in the automated flow process;

determining, based on one or more indicators associated with the second spectral data, one or more second characteristics of a second chemical reaction at the second reaction point in the automated flow process, wherein the artificial intelligence engine determines the second chemical reaction; and associating, based on the second spectral data, the synthesizing recipe with the second chemical reaction.

Clause 3. The method of any clause herein, further comprising:

generating, based on the first and second spectral data and the first and second chemical reaction, a spectral profile associated with the synthesizing recipe implemented by the automated flow process of the sequence.

Clause 4. The method of any clause herein, further comprising:

determining, based on the correlation between the synthesizing recipe and the chemical reaction, a subsequent synthesizing recipe to implement in the automated flow process of the sequence, wherein the artificial intelligence engine determines the subsequent synthesizing recipe.

Clause 5. The method of any clause herein, further comprising:

implementing the subsequent synthesizing recipe in the automated flow process of the sequence.

Clause 6. The method of any clause herein, further comprising:

determining, via the artificial intelligence engine, one or more chemical reactions that result from a plurality of synthesizing recipes being implemented in the automated flow process of the sequence;

filtering, using the artificial intelligence engine, at least one synthesizing recipe from the plurality of synthesizing recipes, wherein the filtering is based on a statistical difference, a probabilistic difference, a percentage difference, an arithmetical difference or some combination thereof.

Clause 7. The method of any clause herein, wherein:

the synthesizing recipe of parameters comprises one or more temperatures, solvents, protection groups, resin anchors, or some combination thereof.

Clause 8. The method of any clause herein, further comprising:

generating, using the AI engine, the sequence based on a desired activity level in a therapeutic domain.

Clause 9. The method of any clause herein, wherein the spectral data comprises ultraviolet light, infrared light, ultraviolet rays, infrared radiation, thermal radiation, thermal light, fluorescent light, visible light, or some combination thereof.

Clause 10. The method of any clause herein, further comprising:

transforming, by the artificial intelligence engine, the spectral data into a mathematical or logical representation; and training, using the mathematical or logical representation, one or more machine learning models of the artificial intelligence engine.

Clause 11. The method of any clause herein, wherein the mathematical or logical representation comprises a vector or eigenvector.

Clause 12. The method of any clause herein, wherein the automated flow synthesis comprises bonding one or more amino acids of the sequence to a resin anchor, wherein the resin anchor comprises at least two linkers, and each of the two linkers is configured to bond with a different respective type of amino acid.

Clause 13. The method of any clause herein, wherein the spectral data includes information pertaining to one or more quality control measurements of the sequence configured to be synthesized using the automated flow process, and the one or more quality control measurements comprise structural information of the sequence, functional information of the sequence, or some combination thereof.

Clause 14. The method of any clause herein, wherein the sequence is a peptide sequence.

Clause 15. The method of any clause herein, wherein the sequence is a peptidomimetic sequence.

Clause 16. A computer-implemented automated flow synthesis platform configured to use an artificial intelligence (AI) engine and comprising:

a reaction chamber configured to synthesize a sequence;

one or more detectors configured to monitor the synthesis of the sequence in the reaction chamber, wherein the synthesis uses an automated flow process; and a computing device communicatively coupled to the one or more detectors, wherein the computing device is configured to:

receive a synthesizing recipe comprising one or more attributes of parameters used during the automated flow process to synthesize the sequence;

receive spectral data from one or more detectors monitoring the automated flow process in the reaction chamber, wherein the spectral data corresponds to a reaction point in the automated flow process;

determine, based on one or more indicators associated with the spectral data, one or more characteristics of a chemical reaction at the reaction point in the automated flow process, wherein the artificial intelligence engine determines the chemical reaction; and associate, based on the spectral data, the synthesizing recipe with the chemical reaction.

Clause 17. The computer-implemented automated flow synthesis platform of any clause herein, wherein the computing device is configured to:

receive second spectral data from the one or more detectors monitoring the automated flow process in the reaction chamber, wherein the second spectral data corresponds to a second reaction point in the automated flow process;

determine, based on one or more indicators associated with the second spectral data, one or more second characteristics of a second chemical reaction at the second reaction point in the automated flow process, wherein the artificial intelligence engine determines the second chemical reaction; and associate, based on the second spectral data, the synthesizing recipe with the second chemical reaction.

Clause 18. The computer-implemented automated flow synthesis platform of any clause herein, wherein the computing device is configured to:

generate, based on the first and second spectral data and the first and second chemical reaction, a spectral profile associated with the synthesizing recipe implemented by the automated flow process of the sequence.

Clause 19. The computer-implemented automated flow synthesis platform of any clause herein, wherein the computing device is further to:

determine, based on the correlation between the synthesizing recipe and the chemical reaction, a subsequent synthesizing recipe to implement in the automated flow process of the sequence, wherein the artificial intelligence engine determines the subsequent synthesizing recipe.

Clause 20. A tangible, non-transitory computer-readable medium storing instructions that, when executed, cause a processing device to:

receive a synthesizing recipe comprising one or more attributes of parameters used during the automated flow process to synthesize the sequence;

receive spectral data from one or more detectors monitoring the automated flow process in the reaction chamber, wherein the spectral data corresponds to a reaction point in the automated flow process;

determine, based on one or more indicators associated with the spectral data, one or more characteristics of a chemical reaction at the reaction point in the automated flow process, wherein the artificial intelligence engine determines the chemical reaction; and associate, based on the spectral data, the synthesizing recipe with the chemical reaction.

Clause 21. A computer-implemented automated flow synthesis platform configured to use an artificial intelligence (AI) engine and comprising:

a reaction chamber configured to synthesize a sequence;

one or more detectors configured to monitor the synthesis of the sequence in the reaction chamber, wherein the synthesis uses an automated flow process; and a computing device communicatively coupled to the one or more detectors, wherein the computing device is configured to:

receive one or more measurements from the one or more detectors, wherein the one or more measurements comprise a spectral profile at each coupling of each amino acid in the sequence;

train, using training data comprising the one or more measurements, one or more machine learning models to determine a synthesizing recipe that enables the sequence to be synthesized, wherein the synthesizing recipe comprises one or more attributes of parameters used during the automated flow process to synthesize the sequence; and control, using the synthesizing recipe, the synthesis of the sequence in the reaction chamber.

Clause 22. The computer-implemented automated flow synthesis platform of any clause herein, wherein the sequence comprises an amino acid.

Clause 23. The computer-implemented automated flow synthesis platform of any clause herein, wherein the amino acid is a non-canonical amino acid.

Clause 24. The computer-implemented automated flow synthesis platform of any clause herein, wherein the amino acid is a canonical amino acid.

Clause 25. The computer-implemented automated flow synthesis platform of any clause herein, wherein the training data comprises one or more inputs associated with one or more outputs, wherein the one or more inputs comprise an amide coupling, a spectral profile for a chemical reaction associated with the amide coupling, a fidelity of the amide coupling, or some combination thereof.

Clause 26. The computer-implemented automated flow synthesis platform of any clause herein, wherein the fidelity of the coupling comprises one of a first indication that an expected chemical reaction occurred at the coupling or a second indication that an unexpected chemical reaction occurred at the coupling.

Clause 27. The computer-implemented automated flow synthesis platform of claim 1, wherein the one or more machine learning models comprise:

a first layer comprising at least a first machine learning model, wherein:

the first machine learning model receives, as first input, an amide coupling of the sequence, a fidelity of the amide coupling, and the spectral profile, and the first machine learning model generates, as an output, at least a subset of the one or more attributes of parameters used during the automated flow process to synthesize the sequence.

Clause 28. The computer-implemented automated flow synthesis platform of any clause herein, wherein the one or more machine learning models comprise:

a second layer comprising at least a second machine learning model, wherein:

the second machine learning model receives, as input, the output of the first machine learning model, and a plurality of amide couplings, the second machine learning model generates, as a second output, at least another subset of the one or more attributes of parameters used during the automated flow process to synthesize the sequence, and the synthesizing recipe comprises the first subset and the second subset of the one or more attributes of parameters.

Clause 29. The computer-implemented automated flow synthesis platform of any clause herein, wherein the sequence is a peptide chain sequence comprising the amide coupling and the plurality of amide couplings.

Clause 30. The computer-implemented automated flow synthesis platform of any clause herein, wherein the synthesizing recipe of attributes of parameters comprises one or more temperatures, solvents, protection groups, resin anchors, or some combination thereof.

Clause 31. The computer-implemented automated flow synthesis platform of any clause herein, further comprising generating, using the one or more machine learning models, the sequence based on a desired drug activity level in a therapeutic domain.

Clause 32. The computer-implemented automated flow synthesis platform of any clause herein, wherein the spectral profile comprises ultraviolet light, infrared light, ultraviolet rays, infrared radiation, thermal radiation, thermal light, fluorescent light, visible light, or some combination thereof.

Clause 33. The computer-implemented automated flow synthesis platform of any clause herein, wherein the sequence is a protein.

Clause 34. The computer-implemented automated flow synthesis platform of any clause herein, wherein the protein is a peptide.

Clause 35. The computer-implemented automated flow synthesis platform of any clause herein, wherein the protein is a peptidomimetic.

Clause 36. A method wherein an artificial intelligence (AI) enabled automated flow synthesis platform, the method comprising:

receiving one or more measurements from one or more detectors, wherein the one or more measurements comprise a spectral profile at each coupling of each amino acid in the sequence, and the one or more detectors are monitoring a synthesis of the sequence in a reaction chamber;

training, using training data comprising the one or more measurements, one or more machine learning models to determine a synthesizing recipe that enables the sequence to be synthesized, wherein the synthesizing recipe comprises one or more attributes of parameters used during the automated flow process to synthesize the sequence; and controlling, using the synthesizing recipe, the synthesis of the sequence in the reaction chamber.

Clause 37. The method of any clause herein, wherein the sequence comprises an amino acid and the amino acid is a non-canonical amino acid.

Clause 38. The method of any clause herein, wherein the one or more machine learning models comprise:

a first layer comprising at least a first machine learning model, wherein:

the first machine learning model receives, as first input, an amide coupling of the sequence, a fidelity of the amide coupling, and the spectral profile, and the first machine learning model generates, as an output, at least a subset of the one or more attributes of parameters used during the automated flow process to synthesize the sequence.

Clause 39. The method of any clause herein, wherein the one or more machine learning models comprise:

a second layer comprising at least a second machine learning model, wherein:

the second machine learning model receives, as input, the output of the first machine learning model, and a plurality of amide couplings, the second machine learning model generates, as a second output, at least another subset of the one or more attributes of parameters used during the automated flow process to synthesize the sequence, and the synthesizing recipe comprises the first subset and the second subset of the one or more attributes of parameters.

Clause 40. A tangible, non-transitory computer-readable medium storing instructions that, when executed, cause a processing device to:

receive one or more measurements from one or more detectors monitoring synthesis of a sequence in a reaction chamber, wherein the one or more measurements comprise a spectral profile at each coupling of each amino acid in the sequence, and the synthesis is performed via an automate flow process;

train, using training data comprising the one or more measurements, one or more machine learning models to determine a synthesizing recipe that enables the sequence to be synthesized, wherein the synthesizing recipe comprises one or more attributes of parameters used during the automated flow process to synthesize the sequence; and control, using the synthesizing recipe, the synthesis of the sequence in the reaction chamber.

What is claimed is:

1. A method wherein an artificial intelligence (AI)-enabled automated flow synthesis platform is configured to generate synthesizing recipes which enable a protein sequence to be synthesized using an automated flow process, the method comprising:

training one or more machine learning models of an AI engine used by the AI-enabled automated flow synthesis platform, wherein:

the AI-enabled automated flow synthesis platform comprises a reaction chamber and one or more detectors used during synthesis, the AI engine comprises a creator module, wherein the creator module comprises the one or more machine learning models that are trained to receive a vector representation of a heterogeneous network of biological context representations and to generate, based on the vector representation and based on using causal inference comprising a counterfactual, the protein sequence, and the vector representation is compressed from a higher-order dimensional level to a lower-order dimensional level to reduce processing complexity;

generating, using the one or more machine learning models of the creator module, the protein sequence based on a desired drug activity level related to an effectiveness of the protein sequence;

when a threshold drug activity level is not satisfied, training the one or more machine learning models to remove the protein sequence from consideration;

when the threshold drug activity level is satisfied, selecting the protein sequence for synthesis;

receiving a synthesizing recipe comprising one or more attributes of parameters used during the automated flow process to synthesize the protein sequence;

initiating the automated flow process;

receiving spectral data from the one or more detectors of the AI-enabled automated flow synthesis platform;

monitoring the automated flow process in the reaction chamber of the AI enabled automated flow synthesis platform, wherein the spectral data corresponds to an amide coupling reaction point in the automated flow process;

determining, based on one or more indicators associated with the spectral data, one or more characteristics of a chemical reaction at the amide coupling reaction point in the automated flow process, wherein, using the one or more machine learning models, the AI engine determines the one or more characteristics of the chemical reaction; and associating, based on the spectral data, the synthesizing recipe with the chemical reaction.

2. The method of claim 1, further comprising:

receiving second spectral data from the one or more detectors monitoring the automated flow process in the reaction chamber, wherein the second spectral data corresponds to a second amide coupling reaction point in the automated flow process;

determining, based on one or more indicators associated with the second spectral data, one or more second characteristics of a second chemical reaction at the second amide coupling reaction point in the automated flow process, wherein, using the one or more machine learning models, the AI engine determines the second chemical reaction; and associating, based on the second spectral data, the synthesizing recipe with the second chemical reaction.

3. The method of claim 2, further comprising:
generating, based on the spectral data, the second spectral data, the chemical reaction, and the second chemical reaction, a spectral profile associated with the synthesizing recipe implemented by the automated flow process of the sequence.

4. The method of claim 1, further comprising:
determining, based on the correlation between the synthesizing recipe and the chemical reaction, a subsequent synthesizing recipe to implement in the automated flow process of the sequence.

5. The method of claim 4, wherein, using the one or more machine learning models, the AI engine determines the subsequent synthesizing recipe.

6. The method of claim 4, further comprising:
implementing the subsequent synthesizing recipe in the automated flow process of the protein sequence to synthesize the protein sequence.

7. The method of claim 1, further comprising:
determining, via the AI engine using the one or more machine learning models, one or more chemical reactions generated by the synthesizing recipes being implemented in the automated flow process of the protein sequence;
filtering, using the AI engine, at least one synthesizing recipe from the synthesizing recipes, wherein the filtering is based on a statistical difference, a probabilistic difference, a percentage difference, an arithmetical difference or some combination thereof.

8. The method of claim 1, wherein:
The one or more attributes of parameters comprise one or more temperatures, solvents, protection groups, resin anchors, pressure, linkers, reagents, catalysts, or some combination thereof.

9. The method of claim 1,
wherein the effectiveness pertains to at least one of an anti-infective effectiveness, anti-cancer effectiveness, antimicrobial effectiveness, anti-viral effectiveness, anti-fungal effectiveness, anti-inflammatory effectiveness, anti-cholinergic effectiveness, anti-dopaminergic effectiveness, anti-serotonergic effectiveness, anti-noradrenergic effectiveness, and anti-prionic effectiveness.

10. The method of claim 1, wherein the spectral data comprises ultraviolet light, infrared light, ultraviolet rays, infrared radiation, thermal radiation, thermal light, fluorescent light, visible light, or some combination thereof.

11. The method of claim 1, further comprising:
transforming, by the AI engine, the spectral data into a mathematical or logical representation; and
training, using the mathematical or logical representation, the one or more machine learning models of the AI engine.

12. The method of claim 11, wherein the mathematical or logical representation comprises a vector or eigenvector.

13. The method of claim 1, wherein the automated flow synthesis comprises bonding one or more amino acids of the protein sequence to a resin anchor, wherein the resin anchor comprises at least two linkers, and each of the two linkers is configured to bond with a different respective type of amino acid.

14. The method of claim 1, wherein the spectral data includes information pertaining to one or more quality control measurements of the protein sequence configured to be synthesized using the automated flow process, and the one or more quality control measurements comprise structural information of the protein sequence, functional information of the protein sequence, or some combination thereof.

15. The method of claim 1, wherein the protein sequence is a peptide sequence.

16. The method of claim 1, wherein the protein sequence is a peptidomimetic sequence.

17. A computer-implemented automated flow synthesis platform configured to use an artificial intelligence (AI) engine and comprising:
a reaction chamber configured to synthesize a protein sequence;
one or more detectors configured to monitor the synthesis of the protein sequence in the reaction chamber, wherein the synthesis uses an automated flow process; and
a computing device communicatively coupled to the one or more detectors, wherein the computing device is configured to execute instructions stored on the computing device, and the instructions are configured so that, when executed, they cause the computing device to:
train one or more machine learning models of an AI-engine used by the AI-enabled automated flow synthesis platform, wherein:
the AI-enabled automated flow synthesis platform comprises a reaction chamber and one or more detectors used during synthesis,
the AI engine comprises a creator module, wherein the creator module comprises the one or more machine learning models that are trained to receive a vector representation of a heterogeneous network of biological context representations and to generate, based on the vector representation and based on using causal inference comprising a counterfactual, the protein sequence, and
the vector representation is compressed from a higher-order dimensional level to a lower-order dimensional level to reduce processing complexity;
generate, using the one or more machine learning models of the creator module, the protein sequence based on a desired drug activity level related to effectiveness of the protein sequence;
when the threshold drug activity level is satisfied, selecting the protein sequence for synthesis;
when a threshold drug activity level is not satisfied, train the one or more machine learning models to remove the protein sequence from consideration;
receive a synthesizing recipe comprising one or more attributes of parameters used during the automated flow process to synthesize the protein sequence;
initiate the automated flow process;
receive spectral data from the one or more detectors;
monitor the automated flow process in the reaction chamber, wherein the spectral data corresponds to a reaction point in the automated flow process;
determine, based on one or more indicators associated with the spectral data, one or more characteristics of a chemical reaction at the reaction point in the automated flow process, wherein, using the one or more machine learning models, the AI engine determines the one or more characteristics of the chemical reaction; and
associate, based on the spectral data, the synthesizing recipe with the chemical reaction.

18. The computer-implemented automated flow synthesis platform of claim 17, wherein the computing device is configured to:

receive second spectral data from the one or more detectors monitoring the automated flow process in the reaction chamber, wherein the second spectral data corresponds to a second reaction point in the automated flow process;

determine, based on one or more indicators associated with the second spectral data, one or more second characteristics of a second chemical reaction at the second reaction point in the automated flow process, wherein, using the one or more machine learning models, the AI engine determines the one or more second characteristics of the second chemical reaction; and associate, based on the second spectral data, the synthesizing recipe with the second chemical reaction.

19. The computer-implemented automated flow synthesis platform of claim 17, wherein the computing device is further to:

determine, based on the correlation between the synthesizing recipe and the chemical reaction, a subsequent synthesizing recipe to implement in the automated flow process of the sequence, wherein the AI engine determines the subsequent synthesizing recipe.

20. A tangible, non-transitory computer-readable medium storing instructions that, when executed, cause a processing device to:

train one or more machine learning models of an AI-engine used by an AI-enabled automated flow synthesis platform, wherein:

the AI-enabled automated flow synthesis platform comprises a reaction chamber and one or more detectors used during synthesis, the AI engine comprises a creator module, wherein the creator module comprises the one or more machine learning models that are trained to receive a vector representation of a heterogeneous network of biological context representations and to generate, based on the vector representation and based on using causal inference comprising a counterfactual, the protein sequence, and the vector representation is compressed from a higher-order dimensional level to a lower-order dimensional level to reduce processing complexity;

generate, using the one or more machine learning models of the creator module, the protein sequence based on a desired drug activity level related to effectiveness of the protein sequence;

when a threshold drug activity level is not satisfied, train the one or more machine learning models to remove the protein sequence from consideration;

when the threshold drug activity level is satisfied, selecting the protein sequence for synthesis;

receive a synthesizing recipe comprising one or more attributes of parameters used during the automated flow process to synthesize a protein sequence;

initiate the automated flow process;

receive spectral data from the one or more detectors;

monitor the automated flow process in the reaction chamber, wherein the spectral data corresponds to an amide coupling reaction point in the automated flow process;

determine, based on one or more indicators associated with the spectral data, one or more characteristics of a chemical reaction at the amide coupling reaction point in the automated flow process, wherein, using the one or more machine learning models, the AI engine determines the one or more characteristics of the chemical reaction; and associate, based on the spectral data, the synthesizing recipe with the chemical reaction.

21. A system for using an artificial intelligence (AI) enabled automated flow synthesis platform configured to generate synthesizing recipes which enable a protein sequence to be synthesized using an automated flow process, the system comprising:

a memory device storing instructions;

a processing device communicatively coupled to the memory device, wherein the instructions are configured to:

train one or more machine learning models of an AI-engine used by an AI-enabled automated flow synthesis platform, wherein:

the AI-enabled automated flow synthesis platform comprises a reaction chamber and one or more detectors used during synthesis;

the AI engine comprises a creator module, wherein the creator module comprises the one or more machine learning models that are trained to receive a vector representation of a heterogeneous network of biological context representations and to generate, based on the vector representation and based on using causal inference comprising a counterfactual, the protein sequence, and the vector representation is compressed from a higher-order dimensional level to a lower-order dimensional level to reduce processing complexity;

generate, using the one or more machine learning models of the creator module, the protein sequence based on a desired drug activity level related to effectiveness of the protein sequence;

when a threshold drug activity level is not satisfied, train the one or more machine learning models to remove the protein sequence from consideration;

when the threshold drug activity level is satisfied, selecting the protein sequence for synthesis;

receive a synthesizing recipe comprising one or more attributes of parameters used during the automated flow process to synthesize the protein sequence;

initiate the automated flow process;

receive spectral data from the one or more detectors;

monitor the automated flow process in the reaction chamber, wherein the spectral data corresponds to an amide coupling reaction point in the automated flow process;

determine, based on one or more indicators associated with the spectral data, one or more characteristics of a chemical reaction at the amide coupling reaction point in the automated flow process, wherein, using the one or more machine learning models, the AI engine determines the one or more characteristics of the chemical reaction; and associate, based on the spectral data, the synthesizing recipe with the chemical reaction.

22. The system of claim 21, wherein the processing device is configured to:

generate, based on the spectral data and the chemical reaction, a spectral profile associated with the synthesizing recipe implemented by the automated flow process of the sequence.

23. The system of claim 21, wherein the processing device is configured to:

determine, based on the correlation between the synthesizing recipe and the chemical reaction, a subsequent synthesizing recipe to implement in the automated flow process of the protein sequence.

24. The system of claim 23, wherein, using the one or more machine learning models, the AI engine determines the subsequent synthesizing recipe.

25. The system of claim 23, further comprising:
implementing the subsequent synthesizing recipe in the automated flow process of the protein sequence to synthesize the protein sequence.

26. The system of claim 21, wherein the processing device is configured to:
determine, via the AI engine, one or more chemical reactions that result from the synthesizing recipes being implemented in the automated flow process of the protein sequence;
filter, using the AI engine, at least one synthesizing recipe from the synthesizing recipes, wherein the filtering is based on a statistical difference, a probabilistic difference, a percentage difference, an arithmetical difference or some combination thereof.

27. The system of claim 21, wherein:
The one or more attributes of parameters comprise one or more temperatures, solvents, protection groups, resin anchors, pressure, linkers, reagents, catalysts, or some combination thereof.

28. The system of claim 21,
wherein the effectiveness pertains to at least one of an anti-infective effectiveness, anti-cancer effectiveness, antimicrobial effectiveness, anti-viral effectiveness, anti-fungal effectiveness, anti-inflammatory effectiveness, anti-cholinergic effectiveness, anti-dopaminergic effectiveness, anti-serotonergic effectiveness, anti-noradrenergic effectiveness, and anti-prionic effectiveness.

29. The system of claim 21, wherein the spectral data comprises ultraviolet light, infrared light, ultraviolet rays, infrared radiation, thermal radiation, thermal light, fluorescent light, visible light, or some combination thereof.

30. The system of claim 21, wherein the processing device is configured to:
transform, by the AI engine, the spectral data into a mathematical or logical representation; and
train, using the mathematical or logical representation, one or more machine learning models of the artificial intelligence engine.

* * * * *